(12) United States Patent
Takikawa et al.

(10) Patent No.: US 7,919,284 B2
(45) Date of Patent: Apr. 5, 2011

(54) L-AMINO ACID PRODUCING MICROORGANISM AND A METHOD FOR PRODUCING AN L-AMINO ACID

(75) Inventors: Rie Takikawa, Kawasaki (JP); Yoshihiko Hara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/497,918

(22) Filed: Jul. 6, 2009

(65) Prior Publication Data

US 2010/0062496 A1 Mar. 11, 2010

Related U.S. Application Data

(63) Continuation of application No. PCT/JP2008/050246, filed on Jan. 11, 2008.

(30) Foreign Application Priority Data

Jan. 22, 2007 (JP) ................................. 2007-011392
May 17, 2007 (JP) ................................. 2007-131763

(51) Int. Cl.
| | |
|---|---|
| *C12P 13/04* | (2006.01) |
| *C12P 21/04* | (2006.01) |
| *C12N 1/20* | (2006.01) |
| *C12N 15/00* | (2006.01) |
| *C12N 9/00* | (2006.01) |
| *C12N 9/02* | (2006.01) |
| *C12N 9/10* | (2006.01) |
| *C12N 9/16* | (2006.01) |
| *C12Q 1/00* | (2006.01) |
| *C12Q 1/68* | (2006.01) |
| *C07H 21/04* | (2006.01) |
| *C07H 21/02* | (2006.01) |

(52) U.S. Cl. .................. 435/106; 435/252.3; 435/320.1; 435/4; 435/6; 435/440; 435/183; 435/189; 435/193; 435/195; 435/69.1; 536/23.2; 536/23.1

(58) Field of Classification Search ........................ None
See application file for complete search history.

(56) References Cited

U.S. PATENT DOCUMENTS

| | | | |
|---|---|---|---|
| 3,563,857 A | 2/1971 | Oki et al. | |
| 5,168,056 A | 12/1992 | Frost | |
| 5,378,616 A | 1/1995 | Tujimoto et al. | |
| 5,393,671 A | 2/1995 | Tujimoto et al. | |
| 5,776,736 A | 7/1998 | Frost et al. | |
| 5,906,925 A | 5/1999 | Liao | |
| 7,247,459 B1 | 7/2007 | Izui et al. | |
| 7,344,874 B2 | 3/2008 | Hara et al. | |
| 7,501,282 B2 | 3/2009 | Hara et al. | |
| 2004/0265956 A1 | 12/2004 | Takikawa et al. | |
| 2006/0019355 A1 | 1/2006 | Ueda et al. | |
| 2006/0040365 A1 | 2/2006 | Kozlov et al. | |
| 2006/0088919 A1 | 4/2006 | Rybak et al. | |

FOREIGN PATENT DOCUMENTS

| | | |
|---|---|---|
| EP | 1 038 970 | 9/2000 |
| JP | 32-9393 | 11/1932 |
| JP | 5-244970 | 9/1993 |
| JP | 2005-237379 | 9/2005 |
| JP | 2005-278643 | 10/2005 |

OTHER PUBLICATIONS

Branden et al. Introduction to Protein Structure, Garland Publishing Inc., New York, p. 247, 1991.*
Gowrishankar, J., et al., "Identification of Osmoresponsive Gene in *Escherichia coli*: Evidence for Participation of Potassium and Proline Transport Systems in Osmoregulation," J. Bacteriol. 1985;164(1):434-445.
Sugiura, A., et al., "Clarification of the structural and functional features of the osmoregulated *kdp* operon of *Escherichia coli*," Mol. Microbiol. 1992;6(13):1769-1776.
Supplementary European Search Report for EP Patent App. No. 08703110.0 (Mar. 30, 2010).
Laimins, L. A., et al., "Identification of the structural proteins of an ATP-driven potassium transport system in *Escherichia coil*," Proc. Natl. Acad. Sci. USA 1978;75(7):3216-3219.
International Search Report for PCT Patent App. No. PCT/JP2008/050246 (Feb. 12, 2008).
Kikuchi, M., et al., Biotechnology of Amino Acid Production, progress in industrial microbiology, vol. 24, pp. 101-116, Kodansha Ltd. Tokyo (corresponding to Kunihiko Akashi et al., "Amino acid fermentation", pp. 195-215, 1986, Japan Scientific Societies Press).
Laimins, L.A., et al., "Osmotic control of *kdp* operon expression in *Escherichia coli*," Proc. Natl. Acad. Sci. USA 1981;78(1):464-468.
Walderhaug, M. O., et al., "KdpD and KdpE, Proteins That Control Expression of the *kdpABC* Operon, Are Members of the Two-Component Sensor-Effector Class of Regulators," J. Bacterial. 1992;174(7);2152-2159.
International Preliminary Report on Patentability for PCT Patent App. No. PCT/JP2008/050246 (Aug. 6, 2009).

* cited by examiner

*Primary Examiner* — Yong D Pak
(74) *Attorney, Agent, or Firm* — Shelly Guest Cermak; Cermak Nakajima LLP

(57) ABSTRACT

A microorganism belonging to the family Enterobacteriaceae, which has an L-amino acid-producing ability and has been modified so that the kdp system is enhanced, is cultured in a medium to produce and accumulate an L-amino acid in the medium or cells of the microorganism, and the L-amino acid is collected from the medium or cells to produce the L-amino acid.

5 Claims, 10 Drawing Sheets

Fig. 6

```
                        1                                            50
KdpA_P.ananatis                                                              (1)
MAANAFLLIAVYLLLLMVMAQPLGRGLAALVADKPLFAR--AEALLWRFS
KdpA_E.coli                                                                  (1)
MAAQGFLLIATFLLVLMVLARPLGSGLARLINDIPLPGTTGVERVLFRAL
Consensus
MAAXXFLLIAXXLLXLMVXAXPLGXGLAXLXXDXPLXXXXXXXEXXLXRXX 51                                          100
KdpA_P.ananatis                                                             (49)
GVQEGGMRWQHYLLAILVFNLLGFVVLLAILMFQGALPLNPQHLPGLSWD
KdpA_E.coli                                                                 (51)
GVSDREMNWKQYLCAILGLNMLGLAVLFFMLLGQHYLPLNPQQLPGLSWD
Consensus
GVXXXXMXWXXYLXAILXXNXLGXXVLXXXLXXQXXLPLNPQXLPGLSWD 101                                         150
KdpA_P.ananatis                                                             (99)
LALNTAISFVTNTNWQSYAGESTLSYFSQMVGLTVQNFVSAATGIAVAFA
KdpA_E.coli                                                                (101)
LALNTAVSFVTNTNWQSYSGETTLSYFSQMAGLTVQNFLSAASGIAVIFA
Consensus
LALNTAXSFVTNTNWQSYXGEXTLSYFSQMXGLTVQNFXSAAXGIAVXFA 151                                         200
KdpA_P.ananatis                                                            (149)
LIRGFANRSVATLGNAWRDLTRITLYVLLPISLLMALFFVSQGSIQNFLP
KdpA_E.coli                                                                (151)
LIRAFTRQSMSTLGNAWVDLLRITLWVLVPVALLIALFFIQQGALQNFLP
Consensus
LIRXFXXXSXXTLGNAWXDLXRITLXVLXPXXLLXALFFXXQGXXQNFLP 201                                         250
KdpA_P.ananatis                                                            (199)
YHNVTSLEGAQQTLAMGPVASQEAIKMLGTNGGGFFNVNSAHPFENPTAL
KdpA_E.coli                                                                (201)
YQAVNTVEGAQQLLPMGPVASQEAIKMLGTNGGGFFNANSSHPFENPTAL
Consensus
YXXVXXXEGAQQXLXMGPVASQEAIKMLGTNGGGFFNXNSXHPFENPTAL 251                                         300
KdpA_P.ananatis                                                            (249)
SNFVQMLSIFLIPAALCFAFGESVKDRRQGSMLLWSMTLMFVVAAALVMW
KdpA_E.coli                                                                (251)
TNFVQMLAIFLIPTALCFAFGEVMGDRRQGRMLLWAMSVIFVICVGVVMW
Consensus
XNFVQMLXIFLIPXALCFAFGEXXXDRRQGXMLLWXMXXXFVXXXXXVMW 301                                         350
KdpA_P.ananatis                                                            (299)
AELRGNPHFLTLGADSAINMEGKETRFGILNSSLFAVITTAASCGAVNAM
KdpA_E.coli                                                                (301)
AEVQGNPHLLALGTDSSINMEGKESRFGVLVSSLFAVVTTAASCGAVIAM
Consensus
AEXXGNPHXLXLGXDSXINMEGKEXRFGXLXSSLFAVXTTAASCGAVXAM 351                                         400
KdpA_P.ananatis                                                            (349)
HDSFTALGGMVPMLLMQLGEVVFGGVGAGLYGMLLFVLLAVFIAGLMIGR
KdpA_E.coli                                                                (351)
HDSFTALGGMVPMWLMQIGEVVFGGVGSGLYGMMLFVLLAVFIAGLMIGR
```

Fig. 6 Continued

```
Consensus
HDSFTALGGMVPMXLMQXGEVVFGGVGXGLYGMXLFVLLAVFIAGLMIGR 401                                          450
KdpA_P.ananatis                                                    (399)
TPEFLGKKIDVWEMKMTALAILVTPALVLIGTAIAMMTDAGRAGMANPGT
KdpA_E.coli                                                        (401)
TPEYLGKKIDVREMKLTALAILVTPTLVLMGAALAMMTDAGRSAMLNPGP
Consensus
TPEXLGKKIDVXEMKXTALAILVTPXLVLXGXAXAMMTDAGRXXMXNPGX 451                                          500
KdpA_P.ananatis                                                    (449)
HGFSEVLYAVSSAANNNGSAFAGLNANTPFWNLLLAVCMFVGRFGIIIPV
KdpA_E.coli                                                        (451)
HGFSEVLYAVSSAANNNGSAFAGLSANSPFWNCLLAFCMFVGRFGVIIPV
Consensus
HGFSEVLYAVSSAANNNGSAFAGLXANXPFWNXLLAXCMFVGRFGXIIPV 501                                          550
KdpA_P.ananatis                                                    (499)
MAIAGAMAVKKVQPVGNGTLPTHGPLFIALLVGTVLLVGALTFIPALALG
KdpA_E.coli                                                        (501)
MAIAGSLVSKKSQAASSGTLPTHGPLFVGLLIGTVLLVGALTFIPALALG
Consensus
MAIAGXXXXKKXQXXXXGTLPTHGPLFXXLLXGTVLLVGALTFIPALALG 551        562
KdpA_P.ananatis  (549) PVAEHLQLIQGQ
KdpA_E.coli      (551) PVAEYLS
Consensus              PVAEXLX
```

Fig. 7

```
                          1                                        50
KdpB_P.ananatis
MSR-QQQVFDAALLRTSAIDAVKKLDPRVQFRNPVMFVVYLGSILTSILA                    (1)
KdpB_E.coli
MSRKQLALFEPTLVVQALKEAVKKLNPQAQWRNPVMFIVWIGSLLTTCIS                    (1)
Consensus
MSRXQXXXFXXXLXXXXXXXXAVKKLXPXXQXRNPVMFXVXXGSXLTXXXX 51                                       100
KdpB_P.ananatis
IMMFTGHQSGSASFTGAIALWLWFTVLFANMAEALAEGRSKAQANSLKGV                   (50)
KdpB_E.coli
IAMASGAMPGNALFSAAISGWLWITVLFANFAEALAEGRSKAQANSLKGV                   (51)
Consensus
IXMXXGXXXGXAXFXXAIXXWLWXTVLFANXAEALAEGRSKAQANSLKGV 101                                       150
KdpB_P.ananatis
KKTSFAKKLSAAHYGAAWQQVAADALRKGDAVLVEAGDVIPCDGEVVEGG                  (100)
KdpB_E.coli
KKTAFARKLREPKYGAAADKVPADQLRKGDIVLVEAGDIIPCDGEVIEGG                  (101)
Consensus
KKTXFAXKLXXXXYGAAXXXVXADXLRKGDXVLVEAGDXIPCDGEVXEGG 151                                       200
KdpB_P.ananatis
ASVDESAITGESAPVIRESGGDFASVTGGTRILSDWLVITCSANPGETFL                  (150)
KdpB_E.coli
ASVDESAITGESAPVIRESGGDFASVTGGTRILSDWLVIECSVNPGETFL                  (151)
Consensus
ASVDESAITGESAPVIRESGGDFASVTGGTRILSDWLVIXCSXNPGETFL 201                                       250
KdpB_P.ananatis
DRMIAMVEGAQRRKTPNEIALTILLVSLTIVFLLATVTLWPFSAWGGTPV                  (200)
KdpB_E.coli
DRMIAMVEGAQRRKTPNEIALTILLIALTIVFLLATATLWPFSAWGGNAV                  (201)
Consensus
DRMIAMVEGAQRRKTPNEIALTILLXXLTIVFLLATXTLWPFSAWGGXXV 251                                       300
KdpB_P.ananatis
TITVLVALLVCLIPTTIGGLLSAIGVAGMSRMLGANVIATSGRAVEAAGD                  (250)
KdpB_E.coli
SVTVLVALLVCLIPTTIGGLLSAIGVAGMSRMLGANVIATSGRAVEAAGD                  (251)
Consensus
XXTVLVALLVCLIPTTIGGLLSAIGVAGMSRMLGANVIATSGRAVEAAGD 301                                       350
KdpB_P.ananatis
VDVLMLDKTGTITLGNRQATQFLPAPGVTEEQLADAAQLASLADETPEGR                  (300)
KdpB_E.coli
VDVLLLDKTGTITLGNRQASEFIPAQGVDEKTLADAAQLASLADETPEGR                  (301)
Consensus
VDVLXLDKTGTITLGNRQAXXFXPAXGVXEXXLADAAQLASLADETPEGR 351                                       400
KdpB_P.ananatis
SIVVLAKQKFNLRERDLSSMGASFIPFSAQTRMSGVNVQDRLIRKGAVDA                  (350)
KdpB_E.coli
SIVILAKQRFNLRERDVQSLHATFVPFTAQSRMSGINIDNRMIRKGSVDA                  (351)
Consensus
SIVXLAKQXFNLRERDXXSXXAXFXPFXAQXRMSGXNXXXRXIRKGXVDA 401                                       450
KdpB_P.ananatis
VRRHIEASHGAFPAEVNARVEEVARAGGTPLVVAEGAKVLGVVALKDIVK                  (400)
KdpB_E.coli
IRRHVEANGGHFPTDVDQKVDQVARQGATPLVVVEGSRVLGVIALKDIVK                  (401)
Consensus
XRRHXEAXXGXFPXXVXXXVXXVARXGXTPLVVXEGXXVLGVXALKDIVK
```

Fig. 7 Continued

```
                    451                                        500
KdpB_P.ananatis                                                     (450)
GGIKERFAELRKMGIKTVMITGDNPLTAAAIAAEAGVDDFLSEATPEAKL
KdpB_E.coli                                                         (451)
GGIKERFAQLRKMGIKTVMITGDNRLTAAAIAAEAGVDDFLAEATPEAKL
Consensus
GGIKERFAXLRKMGIKTVMITGDNXLTAAAIAAEAGVDDFLXEATPEAKL 501                                        550
KdpB_P.ananatis                                                     (500)
ALIRQYQAEGRLVAMTGDGTNDAPALAQADVAVAMNSGTQAAKEAGNMVD
KdpB_E.coli                                                         (501)
ALIRQYQAEGRLVAMTGDGTNDAPALAQADVAVAMNSGTQAAKEAGNMVD
Consensus
ALIRQYQAEGRLVAMTGDGTNDAPALAQADVAVAMNSGTQAAKEAGNMVD 551                                        600
KdpB_P.ananatis                                                     (550)
LDSNPTKLLEVVHIGKQMLMTRGSLTTFSIANDVAKYFAIIPAAFAATYP
KdpB_E.coli                                                         (551)
LDSNPTKLIEVVHIGKQMLMTRGSLTTFSIANDVAKYFAIIPAAFAATYP
Consensus
LDSNPTKLXEVVHIGKQMLMTRGSLTTFSIANDVAKYFAIIPAAFAATYP 601                                        650
KdpB_P.ananatis                                                     (600)
QLNMLNVMQLHSPASAILSAVIFNALVIVFLIPLALKGVSYRPLSAASLL
KdpB_E.coli                                                         (601)
QLNALNIMCLHSPDSAILSAVIFNALIIVFLIPLALKGVSYKPLTASAML
Consensus
QLNXLNXMXLHSPXSAILSAVIFNALXIVFLIPLALKGVSYXPLXAXXXL 651                683
KdpB_P.ananatis    (650) RRNLLIYGLGGLLVPFVGIKAIDMLLVLSGMA
KdpB_E.coli        (651) RRNLWIYGLGGLLVPFIGIKVIDLLLTVCGLV
Consensus                RRNLXIYGLGGLLVPFXGIKXIDXLLXXXGX
```

Fig. 8

```
                         1                                                50
KdpC_P.ananatis                                                              (1)
MSQLRPAIFLLLLLTVVCGVVYPLLTTGLSQLLFPWQANGSVLNVDGEER
KdpC_E.coli                                                                  (1)
MSGLRPALSTFIFLLLITGGVYPLLTTVLGQWWFPWQANGSLIREGDTVR
Consensus
MSXLRPAXXXXXXLXXXXGXVYPLLTTXLQXXFPWQANGSXXXXXXXXXR 51                                               100
KdpC_P.ananatis                                                             (51)
GSALIGQNFSQPGYFWGRPSATGDKPYNPLASSGSNLAASNPALDKAVAE
KdpC_E.coli                                                                 (51)
GSALIGQNFTGNGYFHGRPSATAEMPYNPQASGGSNLAVSNPELDKLIAA
Consensus
GSALIGQNFXXXGYFXGRPSATXXXPYNPXASXGSNLAXSNPXLDKXXAX 101                                              150
KdpC_P.ananatis                                                            (101)
RVAALRTANPQANGAVPVELVTTSASGLDPEISPEAALWQAPRIAAARQL
KdpC_E.coli                                                                (101)
RVAALRAANPDASASVPVELVTASASGLDNNITPQAAAWQIPRVAKARNL
Consensus
RVAALRXANPXAXXXVPVELVTXSASGLDXXIXPXAAXWQXPRXAXARXL 151                      191
KdpC_P.ananatis   (151) PLAKVDALVDSMTQRPLLPFIGEPTVNVLQLNLALNDLK
KdpC_E.coli       (151) SVEQLTQLIAKYSQQPLVKYIGQPVVNIVELNLALDKLDE
Consensus               XXXXXXXLXXXXXQXPLXXXIGXPXVNXXXLNLALXXLX
```

L-AMINO ACID PRODUCING MICROORGANISM AND A METHOD FOR PRODUCING AN L-AMINO ACID

This application is a continuation of PCT/JP2008/050246, filed Jan. 11, 2008, which claims priorities under 35 U.S.C. §119 to Japanese Patent Application No. 2007-011392 filed on Jan. 22, 2007, and Japanese Patent Application No. 2007-131763 filed on May 17, 2007, and which are incorporated in its entirety by reference. The Sequence Listing in electronic format filed herewith is also hereby incorporated by reference in its entirety (File Name: US-399_Seq_List; File Size: 136 KB; Date Created: Jul. 6, 2009).

BACKGROUND OF THE INVENTION

1. Field of the Invention

The present invention relates to a method for producing an L-amino acid using a microorganism, and in particular, methods for producing an L-amino acid wherein the L-amino acid is L-glutamic acid, L-lysine, L-threonine, L-tryptophan or the like. These are industrially useful L-amino acids, for example, L-glutamic acid is useful as a seasoning, and L-lysine, L-threonine and L-tryptophan are useful as animal feed additives, health food ingredients, amino acid infusions, and so forth.

2. Brief Description of the Related Art

L-Amino acids are industrially produced by fermentation using various microorganisms. For example, L-glutamic acid is produced mainly by fermentation utilizing L-glutamic acid-producing bacteria of the so-called coryneform bacteria belonging to the genus *Brevibacterium, Corynebacterium* or *Microbacterium*, or mutant strains thereof (see, for example, Kunihiko Akashi et al., "Amino acid fermentation", pp. 195-215, 1986, Japan Scientific Societies Press). As methods for producing L-glutamic acid by fermentation using other bacterial strains, methods of using a microorganism belonging to the genus *Bacillus, Streptomyces, Penicillium* or the like (refer to, for example, Japanese Patent Laid-open (KOKAI) No. 5-244970), methods of using a microorganism belonging to the genus *Pseudomonas, Arthrobacter, Serratia, Candida* or the like (refer to, for example, U.S. Pat. No. 3,563,857), methods of using a microorganism belonging to the genus *Bacillus, Pseudomonas, Serratia, Aerobacter aerogenes* (currently referred to as *Enterobacter aerogenes*) or the like (refer to, for example, Japanese Patent Publication (KOKOKU) No. 32-9393), methods of using a mutant strain of *Escherichia coli* (refer to, for example, Patent document 1), and so forth are known. In addition, methods for producing L-glutamic acid using a microorganism belonging to the genus *Klebsiella, Erwinia, Pantoea* or *Enterobacter* have also been disclosed (refer to, for example, U.S. Pat. No. 3,563,857, Japanese Patent Publication (KOKOKU) No. 32-9393, Japanese Patent Laid-open No. 2000-189175).

Such methods for producing target substances such as L-amino acids by fermentation using a microorganism as described above include methods of using a wild-type microorganism (wild-type strain), methods of using an auxotrophic strain derived from a wild-type strain, methods of using a metabolic regulation mutant strain derived from a wild-type strain as a strain resistant to one or more various drugs, methods of using a strain which is both an auxotrophic strain and metabolic regulation mutant strain, and so forth.

In recent years, recombinant DNA techniques have been used in the production of target substances by fermentation. For example, L-amino acid productivity of a microorganism can be improved by enhancing expression of a gene encoding an L-amino acid biosynthetic enzyme (U.S. Pat. Nos. 5,168,056 and 5,776,736), or by enhancing the inflow of a carbon source into an L-amino acid biosynthesis system (U.S. Pat. No. 5,906,925).

The kdp system functions as a P-type ATPase and works to take up potassium ions (Laimonis A. Laimins, Proc. Natl. Acad. Sci. USA, 1978 July, 75(7):3216-19). The kdp system is encoded by the kdp operon, and expression thereof is induced when the potassium ion concentration in a medium is low, or when the culture is performed under hyperosmotic conditions (Laimonis A. Laimins, Proc. Natl. Acad. Sci. USA, 1981 January, 78(1):464-68). Furthermore, it is known that the expression is controlled by KdpD and KdpE which constitute one of several binary control systems (Mark O. Walderhaug, J. Bacteriol., 1992 April, 174 (7):2152-59). However, the relationship between the enhancement of the kdp system and L-amino acid production has not been previously investigated.

SUMMARY OF THE INVENTION

An aspect of the present invention is to provide a microorganism that belongs to the family Enterobacteriaceae and is capable of efficiently producing an L-amino acid, and also to provide a method of efficiently producing an L-amino acid using such a microorganism.

It was found that L-amino acids can be efficiently produced by using a microorganism in which kdp system is enhanced.

It is an aspect of the present invention to provide a microorganism belonging to the family Enterobacteriaceae, which has an L-amino acid-producing ability and has been modified so that the kdp system is enhanced.

It is a further aspect of the present invention to provide the aforementioned microorganism, wherein the kdp system is enhanced by a method selected from the group consisting of a) increasing expression of the kdp operon, b) increasing expression of one or more genes on the kdp operon, c) increasing translation of the kdp operon, d) increasing translation of one or more genes on the kdp operon, and combinations thereof.

It is a further aspect of the present invention to provide the aforementioned microorganism, wherein the kdp system is enhanced by a method selected from the group consisting of a) increasing copy number of the kdp operon, increasing the copy number of one or more genes on the kdp operon, and c) modifying an expression control sequence of the operon.

It is a further aspect of the present invention to provide the aforementioned microorganism, wherein the kdp operon comprises the kdpA, kdpB and kdpC genes.

It is a further aspect of the present invention to provide the aforementioned microorganism, wherein the kdpA gene encodes a protein having the amino acid sequence shown in SEQ ID NO: 2 or 8, wherein said protein can include substitutions, deletions, insertions or additions of one or several amino acid residues.

It is a further aspect of the present invention to provide the aforementioned microorganism, wherein the kdpB gene encodes a protein having the amino acid sequence shown in SEQ ID NO: 3 or 9, and wherein said protein can include substitutions, deletions, insertions, or additions of one or several amino acid residues.

It is a further aspect of the present invention to provide the aforementioned microorganism, wherein the kdpC gene encodes a protein having the amino acid sequence shown in SEQ ID NO: 4 or 10, wherein said protein can include substitutions, deletions, insertions or additions of one or several amino acid residues.

It is a further aspect of the present invention to provide the aforementioned microorganism, wherein the kdp operon is selected from the group consisting of:

(a) a DNA comprising the nucleotide sequence of numbers 546 to 4871 of SEQ ID NO: 1, (b) a DNA which hybridizes with the nucleotide sequence of the nucleotide numbers 546 to 4871 of SEQ ID NO: 1, or a probe prepared from the nucleotide sequence, under stringent conditions, wherein said DNA encodes the kdp system, (c) a DNA comprising the nucleotide sequence of numbers 543 to 4853 of SEQ ID NO: 7, (d) a DNA which hybridizes with the nucleotide sequence of numbers 543 to 4853 of SEQ ID NO: 7, or a probe prepared from the nucleotide sequence, under stringent conditions, wherein said DNA encodes the kdp system.

It is a further aspect of the present invention to provide the aforementioned microorganism, wherein the L-amino acid is selected from the group consisting of L-glutamic acid, L-lysine, L-threonine, L-arginine, L-histidine, L-isoleucine, L-valine, L-leucine, L-phenylalanine, L-tyrosine, L-tryptophan, L-cysteine, and combinations thereof.

It is a further aspect of the present invention to provide the aforementioned microorganism, wherein the microorganism is selected from the group consisting of an *Escherichia* bacterium, an *Enterobacter* bacterium, and a *Pantoea* bacterium.

It is a further aspect of the present invention to provide a method for producing an L-amino acid comprising culturing the aforementioned microorganism in a medium to produce and accumulate an L-amino acid in the medium or the microorganism, and collecting the L-amino acid from the medium or microorganism.

It is a further aspect of the present invention to provide the aforementioned method, wherein the L-amino acid is selected from the group consisting of L-glutamic acid, L-lysine, L-threonine, L-arginine, L-histidine, L-isoleucine, L-valine, L-leucine, L-phenylalanine, L-tyrosine, L-tryptophan, L-cysteine, and combinations thereof.

BRIEF DESCRIPTION OF THE DRAWINGS

FIG. 6 shows the alignment of the amino acid sequences of KdpA of *Pantoea ananatis* (SEQ ID NO: 8) and *Escherichia coli* (SEQ ID NO: 2), and the consensus sequence between them (SEQ ID NO: 57).

FIG. 7 shows the alignment of the amino acid sequences of KdpB of *Pantoea ananatis* (SEQ ID NO: 9) and *Escherichia coli* (SEQ ID NO: 3), and the consensus sequence between them (SEQ ID NO: 58).

FIG. 8 shows the alignment of the amino acid sequences of KdpC of *Pantoea ananatis* (SEQ ID NO: 10) and *Escherichia coli* (SEQ ID NO: 4), and the consensus sequence between them (SEQ ID NO: 59).

DETAILED DESCRIPTION OF EXEMPLARY EMBODIMENTS

Figure 1:
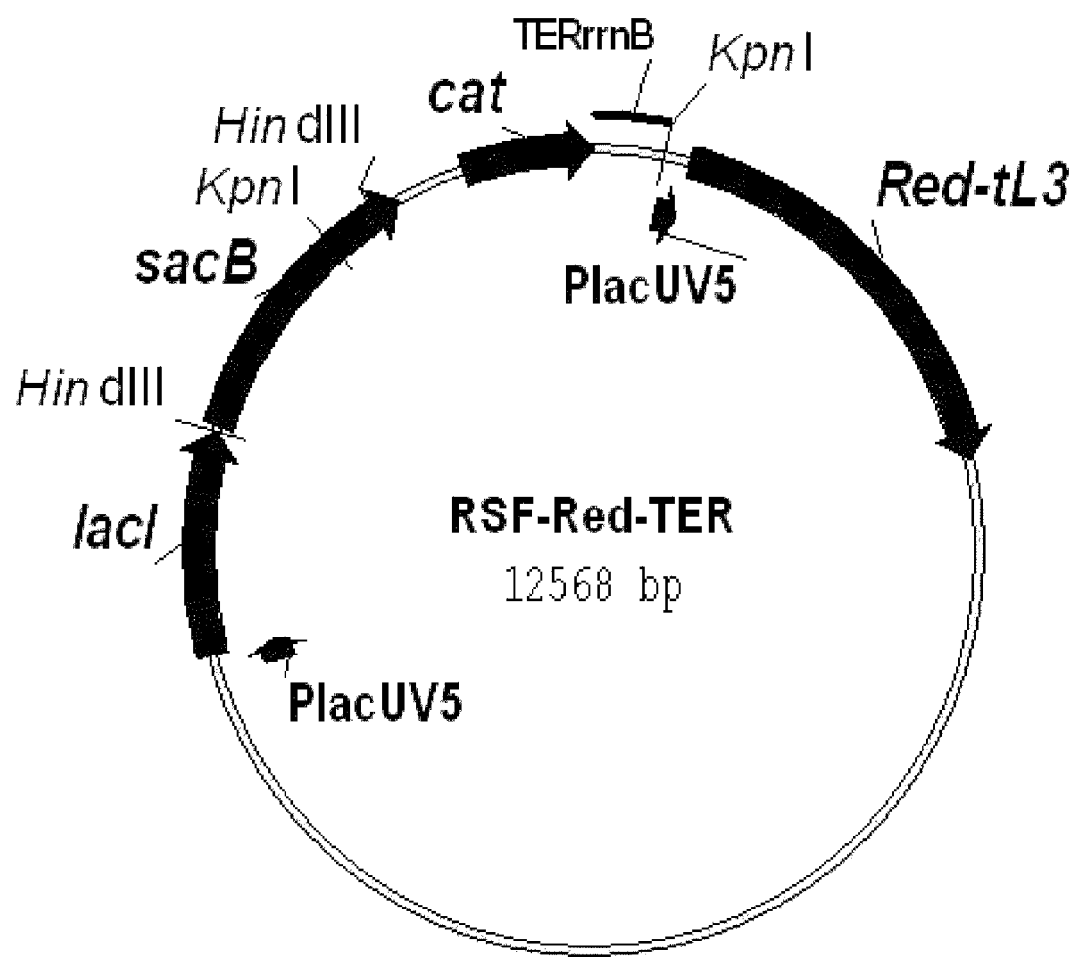
FIG. 1 shows the structure of the helper plasmid RSF-Red-TER.

Hereafter, the present invention will be explained in detail.

<1> Microorganism

An exemplary microorganism of the present invention belongs to the family Enterobacteriaceae, is able to produce an L-amino acid, and has been modified so that the kdp system is enhanced. The L-amino acid-producing ability means an ability of the microorganism to produce and accumulate an L-amino acid in a medium or cells of the microorganism in such an amount that the L-amino acid can be collected from the medium or cells, when the microorganism is cultured in the medium. The microorganism may be able to produce two or more kinds of L-amino acids. The microorganism may inherently be able to produce an L-amino acid, or a may be modified as described below so as to impart the ability to produce an L-amino acid using a mutation method or recombinant DNA techniques.

The type of the L-amino acid is not particularly limited, and examples include basic amino acids such as L-lysine, L-ornithine, L-arginine, L-histidine and L-citrulline, aliphatic amino acids such as L-isoleucine, L-alanine, L-valine, L-leucine and L-glycine, amino acids which are hydroxymonoaminocarboxylic acids such as L-threonine and L-serine, cyclic amino acids such as L-proline, aromatic amino acids such as L-phenylalanine, L-tyrosine and L-tryptophan, sulfur-containing amino acids such as L-cysteine, L-cystine and L-methionine, and acidic amino acids such as L-glutamic acid, L-aspartic acid, L-glutamine and L-asparagine. L-Glutamic acid, L-lysine, L-threonine and L-tryptophan are especially preferred. The microorganism may have the ability to produce two or more kinds of amino acids.

<1-1> Impartation of L-Amino Acid-Producing Ability

Examples of methods for imparting L-amino acid-producing ability and microorganisms to which L-amino acid-producing ability is imparted will be described below. However, the microorganism is not limited to these so long as the microorganism is able to produce an L-amino acid.

Exemplary microorganisms include microorganisms belonging to the genus *Escherichia, Enterobacter, Pantoea, Klebsiella, Serratia, Erwinia, Salmonella, Morganella*, or the like, so long as they belong to the family Enterobacteriaceae and are able to produce an L-amino acid. In particular, bacteria classified into the family Enterobacteriaceae according to the taxonomy used by the NCBI (National Center for Biotechnology Information) database (http://www.ncbi.nlm-.nih.gov/Taxonomy/Browser/wwwtax.cgi?id=91347) can be used. As parent strains of Enterobacteriaceae which can be modified, bacteria belonging to the genus *Escherichia, Enterobacter, Pantoea, Erwinia*, or *Klebsiella* may be used.

The parent strain of *Escherichia* bacteria which can be modified to obtain an exemplary *Escherichia* bacterium of the present invention is not particularly limited. Those described in the work of Neidhardt et al. (Backmann, B. J., 1996. Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.) can be utilized. Among them, for example, *Escherichia coli* is exemplified. Examples of *Escherichia coli* include the W3110 strain (ATCC No. 27325), MG1655 strain (ATCC No. 47076), and so forth, which are derivatives of a prototype wild-type strain, the K12 strain.

These strains are available from, for example, the American Type Culture Collection (ATCC) (Address: 12301

Parklawn Drive, Rockville, Md. 20852, P.O. Box 1549, Manassas, Va. 20108, United States of America). That is, each strain is given a unique registration number (http://www.atcc.org/). Strains can be ordered by using this registration number. The registration number of each strain is listed in the catalogue of the ATCC.

Examples of the *Enterobacter* bacteria include, *Enterobacter agglomerans, Enterobacter aerogenes*, and so forth. Examples of the *Pantoea* bacteria include *Pantoea ananatis*. In recent years, some bacteria of *Enterobacter agglomerans* were reclassified as *Pantoea agglomerans, Pantoea ananatis*, or *Pantoea stewartii*, on the basis of nucleotide sequence analysis of the 16S rRNA etc. The microorganism may belong to either the genus *Enterobacter* or *Pantoea* so long as the microorganism is classified into the family *Enterobacteriaceae*.

In particular, *Pantoea* bacteria, *Erwinia* bacteria, and *Enterobacter* bacteria are classified as γ-proteobacteria, and are taxonomically very close to one another (J. Gen. Appl. Microbiol., 1997, 43, 355-361; Int. J. Syst. Bacteriol., 1997, 43, 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39:337-345). Furthermore, some bacteria belonging to the genus *Erwinia* were reclassified as *Pantoea ananas* or *Pantoea stewartii* (refer to Int. J. Syst. Bacteriol., 1993, 43:162-173).

Examples of the *Enterobacter* bacteria include *Enterobacter agglomerans, Enterobacter aerogenes*, and so forth. Specifically, the strains exemplified in European Patent Laid-open No. 952221 can be used.

Exemplary strains of the genus *Enterobacter* include the *Enterobacter agglomeranses* ATCC 12287 strain.

Exemplary strains of the *Pantoea* bacteria include *Pantoea ananatis, Pantoea stewartii, Pantoea agglomerans*, and *Pantoea citrea*. Specific examples include the following strains:

*Pantoea ananatis* AJ13355 (FERM BP-6614, European Patent Laid-open No. 0952221)

*Pantoea ananatis* AJ13356 (FERM BP-6615, European Patent Laid-open No. 0952221)

*Pantoea ananatis* AJ13601 (FERM BP-7207, European Patent Laid-open No. 0952221)

Although these strains were identified and deposited as *Enterobacter agglomerans* when they were isolated, they are currently classified as *Pantoea ananatis* on the basis of nucleotide sequence analysis of the 16S rRNA etc., as described above.

Examples of the *Erwinia* bacteria include *Erwinia amylovora* and *Erwinia carotovora*, and examples of the *Klebsiella* bacteria include *Klebsiella planticola*. Specific examples include the following strains:

*Erwinia amylovora* ATCC 15580
*Erwinia carotovora* ATCC 15713
*Klebsiella planticola* AJ13399 (FERM BP-6600, European Patent Laid-open No. 955368)
*Klebsiella planticola* AJ13410 (FERM BP-6617, European Patent Laid-open No. 955368).

Hereafter, methods for imparting an L-amino acid-producing ability to bacteria of Enterobacteriaceae, or methods for enhancing an L-amino acid-producing ability of such bacteria are described.

To impart an ability to produce an L-amino acid, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include acquisition of an auxotrophic mutant, an analogue-resistant strain, or a metabolic regulation mutant, construction of a recombinant strain in which expression of an L-amino acid biosynthesis is enhanced, and so forth. Here, in the breeding of an L-amino acid-producing bacteria, the one or more properties such as an auxotrophic mutation, analogue resistance, or metabolic regulation mutation may be imparted. The expression of L-amino acid biosynthesis enzyme(s) can be enhanced alone or in combinations of two or more. Furthermore, the methods of imparting properties such as an auxotrophic mutation, analogue resistance, or metabolic regulation mutation may be combined with the methods of enhancing the biosynthesis enzymes.

An auxotrophic mutant strain, L-amino acid analogue-resistant strain, or metabolic regulation mutant strain with an ability to produce an L-amino acid can be obtained by subjecting a parent strain or wild-type strain to conventional mutatagenesis, such as exposure to X-rays or UV irradiation, or treatment with a mutagen such as N-methyl-N'-nitro-N-nitrosoguanidine (NTG), ethyl methanesulfonate (EMS), etc., then selecting those which exhibit autotrophy, analogue resistance, or a metabolic regulation mutation and which also have an ability to produce an L-amino acid.

L-amino acid-producing bacteria and methods for constructing these bacteria are exemplified below.

L-Glutamic Acid-Producing Bacteria

First, L-glutamic acid-producing bacteria are explained as L-amino acid-producing bacteria.

Examples of parent strains which can be used to derive L-glutamic acid-producing bacteria include, but are not limited to, strains belonging to the genus *Escherichia*, such as *E. coli* VL334thrC$^+$ (European Patent No. 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961) was obtained.

Examples of methods for imparting L-glutamic acid-producing ability to a bacterium or enhancing the ability of the bacterium include, for example, modifying a bacterium so that expression of a gene encoding an enzyme involved in L-glutamic acid biosynthesis is enhanced.

Examples of enzymes involved in L-glutamic acid biosynthesis include glutamate dehydrogenase (hereinafter also referred to as "GDH") (gdh), glutamine synthetase (glnA), glutamate synthetase (gltAB), isocitrate dehydrogenase (icdA), aconitate hydratase (acnA, acnB), citrate synthase (hereinafter also referred to as "CS") (gltA), methylcitrate synthase (hereinafter also referred to as "PRPC" (prpC), phosphoenolpyruvate carboxylase (hereinafter also referred to as "PEPC") (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi), and so forth. The abbreviations in parentheses are the gene names which correspond to the enzymes, and this convention is used throughout this specification. Among these enzymes, the use of one or more of CS or PRPC, PEPC and GDH is one example, and the use of all three enzymes is another example (refer to WO2006/051660).

Methods for modifying a bacterium to increase target gene expression will be explained below.

The first method is to increase the copy number of a target gene. For example, the copy number of a target gene can be increased by cloning the target gene on an appropriate plasmid and transforming a host bacterium with the obtained plasmid. For example, when the target gene is the gene encoding CS (gltA gene), the gene encoding PRPC (prpC gene), the gene encoding PEPC (ppc gene) or the gene encoding GDH (gdhA gene), the nucleotide sequences of these genes from *Escherichia* bacteria and *Corynebacterium* bacteria have already been elucidated (Biochemistry, vol. 22, pp. 5243-5249, 1983; J. Biochem., vol. 95, pp. 909-916, 1984; Gene, vol. 27, pp. 193-199, 1984; Microbiology, vol. 140, pp. 1817-1828, 1994; Mol. Gen. Genet., vol. 218, pp. 330-339, 1989; Molecular Microbiology, vol. 6, pp. 317-326, 1992), and therefore they can be obtained by synthesizing primers based on their respective nucleotide sequences, and performing PCR using chromosomal DNA of a bacterium belonging to the family Enterobacteriaceae as the template.

Examples of the plasmid which can be used for transformation include a plasmid which autonomously replicates in the host bacterium belonging to the family Enterobacteriaceae, such as pUC19, pUC18, pBR322, RSF1010, pHSG299, pHSG298, pHSG399, pHSG398, pSTV28, pSTV29 (pHSG and pSTV are available from Takara Bio Inc.), pMW119, pMW118, pMW219, pMW218 (pMW vectors are available from Nippon Gene Co., Ltd.), and so forth. Moreover, a phage DNA may also be used as the vector instead of a plasmid. Examples of plasmids which can be used to simultaneously enhance the activities of CS or PRPC, PEPC and GDH as described above include RSFCPG which has been incorporated with the gltA gene, ppc gene and gdhA gene (refer to European Patent Laid-open No. 0952221), and RSFPPG corresponding to RSFCPG in which the gltA gene is replaced with the prpC gene (refer to the examples).

Examples of transformation methods include treating recipient cells with calcium chloride so to increase permeability of the DNA, which has been reported for *Escherichia coli* K-12 (Mandel, M. and Higa, A., 1970, J. Mol. Biol., 53:159-162), and preparing competent cells from cells which are in the growth phase, followed by transformation with DNA, which has been reported for *Bacillus subtilis* (Duncan, C. H., Wilson, G. A. and Young, F. E. 1977, Gene, 1:153-167). Alternatively, a method of making DNA-recipient cells into protoplasts or spheroplasts, which can easily take up recombinant DNA, followed by introducing the recombinant DNA into the cells, which is known to be applicable to *Bacillus subtilis*, actinomycetes, and yeasts (Chang, S. and Choen, S. N., 1979, Mol. Gen. Genet., 168:111-115; Bibb, M. J. et al., 1978, Nature, 274:398-400; Hinnen, A., Hicks, J. B. and Fink, G. R. 1978, Proc. Natl. Sci., USA, 75:1929-1933) can also be employed. In addition, microorganisms can also be transformed by the electric pulse method (Japanese Patent Laid-open No. 2-207791).

The copy number of a gene can also be increased by introducing multiple copies of the gene into the chromosomal DNA of the microorganism, which can be performed by homologous recombination (MillerI, J. H. Experiments in Molecular Genetics, 1972, Cold Spring Harbor Laboratory) using multiple copies of a sequence as targets in the chromosomal DNA. Sequences present in multiple copies on the chromosomal DNA include repetitive DNAs, and inverted repeats present at the end of a transposable element. Also, as disclosed in Japanese Patent Laid-open No. 2-109985, it is possible to incorporate the target gene into a transposon, and allow it to be transferred to introduce multiple copies of the gene into the chromosomal DNA. The target gene can also be introduced into the bacterial chromosome by Mu phage (Japanese Patent Laid-open No. 2-109985), or the like.

The second method is to increase expression of the target gene by replacing an expression regulatory sequence of the target gene, such as promoter, on the chromosomal DNA or plasmid with a stronger promoter. For example, the lac promoter, trp promoter, trc promoter, PR promoter, lacUV5 promoter, etc. are known as strong promoters. Moreover, it is also possible to substitute several nucleotides in the promoter region of a gene, so that the promoter is stronger, as disclosed in International Patent Publication WO00/18935. Examples of strong promoters and methods for evaluating strength of promoters are described in an article of Goldstein et al. (Prokaryotic promoters in biotechnology. Biotechnol. Annu. Rev., 1995, 1, 105-128), etc.

Substitution of an expression regulatory sequence can be performed, for example, in the same manner as in gene substitution using a temperature-sensitive plasmid. Examples of vectors having a temperature-sensitive replication origin which functions in exemplary bacterium of the present invention belonging to the family Enterobacteriaceae include, for example the pMAN997 plasmid described in International Publication WO99/03988, and so forth.

Furthermore, it is known that substitutions of several nucleotides in the spacer region between the ribosome binding site (RBS) and the start codon, in particular, a sequence immediately upstream from the start codon, greatly affects translation efficiency of mRNA. By modifying these, translation can be improved.

Modification of an expression control sequence may be combined with the method of increasing the copy number of a gene described above.

Examples of the methods for gene substitution as described above include methods which employ linear DNA, such as "Red-driven integration" (Datsenko, K. A. and Wanner, B. L., Proc. Natl. Acad. Sci. USA., 97:6640-6645 (2000)), and Red-driven integration in combination with the λ phage excision system (Cho, E. H., Gumport, R. I., Gardner, J. F. 2002, J. Bacteriol., 184:5200-5203) (WO2005/010175), and so forth, methods using a plasmid containing a temperature-sensitive replication origin, methods using a plasmid capable of conjugative transfer, methods utilizing a suicide vector which does not have a replication origin which functions in the chosen host (U.S. Pat. No. 6,303,383, Japanese Patent Laid-open No. 05-007491) etc.

As shown in Reference Example 1, a strain resistant to a λ Red gene product, for example, the *Pantoea ananatis* SC17 (0) strain, can be suitably used for the Red driven integration. The SC17(0) strain was deposited at the Russian National Collection of Industrial Microorganisms (VKPM), GNII Genetika (Russia, 117545 Moscow 1, Dorozhny proezd. 1) on Sep. 21, 2005 under the accession number VKPM B-9246.

Examples of microorganisms which have been modified by the method described above so that expression of citrate synthase gene, methyl citrate synthase gene, phosphoenolpyruvate carboxylase gene and/or glutamate dehydrogenase gene is enhanced include the microorganisms disclosed in Japanese Patent Laid-open Nos. 2001-333769, 2000-106869, 2000-189169 2000-333769, 2006-129840, WO2006/051660, and so forth.

Furthermore, L-glutamic acid-producing ability can also be imparted by enhancing the 6-phosphogluconate dehydratase activity, 2-keto-3-deoxy-6-phosphogluconate aldolase activity, or both these activities. Examples of the microorganism of which 6-phosphogluconate dehydratase activity and 2-keto-3-deoxy-6-phosphogluconate aldolase activity are increased include the microorganism disclosed in Japanese Patent Laid-open No. 2003-274988.

The modification for imparting L-glutamic acid-producing ability or enhancing it may also be attained by reducing or eliminating activity of an enzyme that catalyzes a reaction which branches off from the L-glutamic acid biosynthesis pathway and producing a compound other than L-glutamic acid. Examples of such an enzyme include 2-oxoglutarate dehydrogenase (α-ketoglutarate dehydrogenase (sucA)), isocitrate lyase (aceA), phosphate acetyltransferase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), 1-pyrroline-5-carboxylate dehydrogenase (putA), and so forth. Reducing or eliminating the activity of 2-oxoglutarate dehydrogenase is one example.

In order to reduce or eliminate the activities of the aforementioned enzymes, mutations for reducing or eliminating intracellular activities of the enzymes can be introduced into genes of the aforementioned enzymes by a usual mutagenesis treatment or a genetic engineering technique. Examples of the mutagenesis treatment include, for example, methods utilizing irradiation of X-ray or ultraviolet ray, methods utilizing treatment with a mutagen such as N-methyl-N'-nitro-N-nitrosoguanidine, and so forth. The mutation can be introduced into a coding region of the gene encoding an enzyme protein or a region for regulating expression such as a promoter. Examples of the genetic engineering techniques include methods using genetic recombination, transduction, cell fusion and so forth.

Decreasing the intracellular activity of a target enzyme and the degree by which the activity is decreased can be confirmed by measuring the enzyme activity in a cell extract or a purified fraction thereof obtained from a candidate strain and comparing it with that of a wild-type strain. For example, the 2-oxoglutarate dehydrogenase activity can be measured by the method of Reed et al. (L. J. Reed and B. B. Mukherjee, Methods in Enzymology, 13, pp. 55-61 (1969)).

Bacteria belonging to the genus $Escherichia$ which are deficient in the 2-oxoglutarate dehydrogenase activity or in which 2-oxoglutarate dehydrogenase activity is reduced include the following strains (U.S. Pat. Nos. 5,378,616 and 5,573,945):

$E.\ coli$ W3110sucA::Kmr
$E.\ coli$ AJ12624 (FERM BP-3853)
$E.\ coli$ AJ12628 (FERM BP-3854)
$E.\ coli$ AJ12949 (FERM BP-4881)

$E.\ coli$ W3110sucA::Kmr is obtained by disrupting the 2-oxoglutarate dehydrogenase gene (sucA gene) of $E.\ coli$ W3110. This strain is completely deficient in the α-ketoglutarate dehydrogenase.

Specifically, examples of bacterium wherein the activity of 2-oxoglutarate dehydrogenase is deleted or reduced include the following strains:

*Pantoea ananatis* AJ13601 (FERM BP-7207, European Patent Laid-open No. 1078989)

*Pantoea ananatis* AJ13356 (FERM BP-6615, U.S. Pat. No. 6,331,419)

*Pantoea ananatis* SC17sucA (FERM BP-8646, WO2005/085419)

*Klebsiella planticola* AJ13410 strain (FERM BP-6617, U.S. Pat. No. 6,197,559)

The SC17sucA strain is obtained by selecting a low phlegm production mutant strain (SC17) from the AJ13355 strain, which was isolated from nature as a strain that could proliferate in a medium containing L-glutamic acid and a carbon source at low pH, and disrupting the 2-oxoglutarate dehydrogenase gene (sucA) of the mutant strain. The AJ13601 strain was obtained by introducing the plasmid RSFCPG containing the gltA, ppc and gdhA genes derived from $Escherichia\ coli$ and the plasmid pSTVCB containing the gltA gene derived from *Brevibacterium lactofermentum* into the SC17sucA strain to obtain the SC17sucA/RSFCPG+pSTVCB strain, and selecting a high concentration an L-glutamic acid resistant strain at a low pH, and a strain showing a high proliferation degree and a high L-glutamic acid producing ability from the SC17sucA/RSFCPG+pSTVCB strain (European Patent Laid-open No. 0952221). The AJ13356 strain was obtained by deleting the αKGDH-E1 subunit gene (sucA) of the AJ13355 strain. Furthermore, the NP106 strain described in the examples corresponds to the AJ13601 strain from which the plasmid RSFCPG+pSTVCB is eliminated.

The *Pantoea ananatis* AJ13355 and AJ13356 stains were deposited on Feb. 19, 1998 in National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan), as deposit number of FERM P-16644 and FERM P-16645 respectively, and were converted from the original deposit to an international deposit based on Budapest Treaty on Jan. 11, 1999, and given an accession number of FERM BP-6644 and FERM BP-6615, respectively. The SC17sucA strain was assigned a private number of AJ417, and was deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Feb. 26, 2004, and assigned an accession number of FERM BP-08646. The *Pantoea ananatis* AJ13601 stain was deposited on Aug. 18, 1999 in the National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan), as deposit number FERM P-17156, and was converted from the original deposit to an international deposit based on the Budapest Treaty on Jul. 6, 2000 and given an accession number of FERM BP-7207.

The aforementioned *Pantoea ananatis* AJ13355, AJ13356, and AJ13601 strains and *Klebsiella planticola* AJ13399 strain have an ability to produce L-glutamic acid in a concentration which exceeds the saturation concentration of L-glutamic acid in a liquid medium when it is cultured under acidic conditions.

Furthermore, in order to improve L-glutamic acid-producing ability of Enterobacteriaceae bacteria, the method of deleting the arcA gene (U.S. Pat. No. 7,090,998), and the method of amplifying the yhfK gene, which is a glutamic acid secretion gene (WO2005/085419 pamphlet) can also be used.

The aforementioned method of enhancing or deleting enzyme activity is similarly applicable to bacteria for producing other amino acids as described below.

L-Threonine-Producing Bacteria

Examples of parent strains which can be used to derive the L-threonine-producing bacteria include, but are not limited to, strains belonging to the genus $Escherichia$, such as $E.\ coli$ TDH-6/pVIC40 (VKPM B-3996) (U.S. Pat. No. 5,175,107, U.S. Pat. No. 5,705,371), $E.\ coli$ 472T23/pYN7 (ATCC 98081) (U.S. Pat. No. 5,631,157), $E.\ coli$ NRRL-21593 (U.S. Pat. No. 5,939,307), $E.\ coli$ FERM BP-3756 (U.S. Pat. No. 5,474,918), $E.\ coli$ FERM BP-3519 and FERM BP-3520

(U.S. Pat. No. 5,376,538), *E. coli* MG442 (Gusyatiner et al., Genetika (in Russian), 14, 947-956 (1978)), *E. coli* VL643 and VL2055 (European Patent Laid-open No. 1149911), and the like.

The TDH-6 strain is deficient in the thrC gene, as well as being sucrose-assimilative, and the ilvA gene thereof has a leaky mutation. This strain also has a mutation in the rhtA gene, which imparts resistance to high concentrations of threonine or homoserine. The B-3996 strain contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russian Federation) under the accession number RIA 1867. The strain was also deposited in the Russian National Collection of Industrial Microorganisms (VKPM) (Russia, 117545 Moscow, 1 Dorozhny proezd. 1) on Apr. 7, 1987 under the accession number VKPM B-3996.

*E. coli* VKPM B-5318 (European Patent Publication No. 0593792) may also be used as a parent strain to derive L-threonine-producing bacteria. The B-5318 strain is prototrophic with regard to isoleucine, and a temperature-sensitive λ-phage C1 repressor and PR promoter replaces the regulatory region of the threonine operon in plasmid pVIC40. The VKPM B-5318 strain was deposited in the Russian National Collection of Industrial Microorganisms (VKPM) on May 3, 1990 under the accession number VKPM B-5318.

The bacterium may be additionally modified to enhance expression of one or more of the following genes:

mutant thrA gene which encodes aspartokinase homoserine dehydrogenase I resistant to feed back inhibition by threonine;

thrB gene which encodes homoserine kinase;

the thrC gene which encodes threonine synthase;

the rhtA gene which encodes a putative transmembrane protein;

the asd gene which encodes aspartate-β-semialdehyde dehydrogenase; and the aspC gene which encodes aspartate aminotransferase (aspartate transaminase).

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region which affects the transcription is desirably removed from the operon (WO2005/049808, W)2003/097839).

A mutant thrA gene which encodes aspartokinase homoserine dehydrogenase I resistant to feedback inhibition by threonine, as well as the thrB and thrC genes can be obtained as one operon from the well-known plasmid pVIC40 which is present in the threonine producing *E. coli* strain VKPM B-3996. Plasmid pVIC40 is described in detail in U.S. Pat. No. 5,705,371.

The rhtA gene is present at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position-1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, European Patent Laid-open No. 1013765).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorgansms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The WC196 strain may be used as a L-lysine-producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, the deposit was converted to an international deposit under the provisions of the Budapest Treaty on Sep. 29, 1995, and received an accession number of FERM BP-5252 (U.S. Pat. No. 5,827, 698).

Examples of parent strains which can be used to derive L-lysine-producing bacteria also include strains in which expression of one or more genes encoding an L-lysine biosynthetic enzyme is/are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (European Patent Laid-open No. 1253195). In addition, the parent strains may have an increased level of expression of the gene involved in energy efficiency (cyo) (European Patent Laid-open No. 1170376), the gene encoding nicotinamide nucleotide transhydrogenase (pntAB) (U.S. Pat. No. 5,830, 716), the ybjE gene (WO2005/073390), or combinations thereof.

Examples of parent strains which can be used to derive L-lysine-producing bacteria also include strains having decreased or eliminated activity of an enzyme that catalyzes a reaction for generating a compound other than L-lysine by branching off from the biosynthetic pathway of L-lysine. Examples of these enzymes include homoserine dehydrogenase, lysine decarboxylase (U.S. Pat. No. 5,827,698), and the malic enzyme (WO2005/010175).

L-Cysteine-Producing Bacteria

Examples of parent strains which can be used to derive L-cysteine-producing bacteria include, but are not limited to, strains belonging to the genus *Escherichia*, such as *E. coli* JM15 which is transformed with different cysE alleles encoding feedback-resistant serine acetyltransferases (U.S. Pat. No. 6,218,168, Russian Patent Application No. 2003121601); *E. coli* W3110 having over-expressed genes which encode proteins suitable for secreting substances toxic for cells (U.S. Pat. No. 5,972,663); *E. coli* strains having lowered cysteine desulfhydrase activity (JP11155571A2); *E. coli* W3110 with increased activity of a positive transcriptional regulator for cysteine regulon encoded by the cysB gene (WO0127307A1), and the like.

L-Leucine-Producing Bacteria

Examples of parent strains which can be used to derive L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5, 5-trifluoroleucine (Japanese Patent Publication No. 62-34397 and Japanese Patent Laid-open No. 8-70879); *E. coli* strains obtained by the gene engineering method described in WO96/06926; *E. coli* H-9068 (Japanese Patent Laid-open No. 8-70879), and the like.

The bacterium may be improved by enhancing expression of one or more genes involved in L-leucine biosynthesis. Examples of such genes include the genes of the leuABCD operon, a typical example of which is a mutant leuA gene encoding isopropylmalate synthase desensitized to feedback inhibition by L-leucine (U.S. Pat. No. 6,403,342). In addition, the bacterium may be improved by enhancing expression of one or more genes encoding proteins which excrete L-amino acid from the bacterial cell. Examples of such genes include the b2682 and b2683 genes (ygaZH genes) (European Patent Laid-open No. 1239041 A2).

L-Histidine-Producing Bacteria

Examples of parent strains which can be used to derive L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (European Patent No. 1085087); *E. coli* AI80/pFM201 (U.S. Pat. No. 6,258,554) and the like.

Examples of parent strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase gene (hisG) (Russian Patent Nos. 2003677 and 2119536).

Specific examples of strains having an L-histidine-producing ability include *E. coli* FERM P-5038 and 5048 which have been introduced with a vector carrying a DNA encoding an L-histidine-biosynthetic enzyme (Japanese Patent Laid-open No. 56-005099), *E. coli* strains introduced with rht, a gene for an amino acid-export (European Patent Laid-open No. 1016710), *E. coli* 80 strain imparted with sulfaguanidine, DL-1,2,4-triazole-3-alanine, and streptomycin-resistance (VKPM B-7270, Russian Patent No. 2119536), and so forth.

L-Phenylalanine-Producing Bacteria

Examples of parent strains which can be used to derive L-phenylalanine-producing bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring a mutant pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407, 952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) may be used (European Patent Publication No. 488424 B1). Furthermore, L-phenylalanine producing bacteria belonging to the genus *Escherichia* with an enhanced activity of the protein encoded by the yedA gene or the yddG gene may also be used (U.S. Patent Application Publication Nos. 2003/0148473 A1 and 2003/0157667 A1, respectively).

L-Tryptophan-Producing Bacteria

Examples of parent strains which can be used to derive the L-tryptophan-producing bacteria include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180, 373); *E. coli* AGX17 (pGX44) (NRRL B-12263) and AGX6 (pGX50)aroP (NRRL B-12264) deficient in the enzyme tryptophanase (U.S. Pat. No. 4,371,614); *E. coli* AGX17/pGX50, pACKG4-pps in which phosphoenolpyruvate-producing ability is enhanced (WO97/08333, U.S. Pat. No. 6,319,696), and the like. L-tryptophan-producing bacteria belonging to the genus *Escherichia* in which the activity of the protein encoded by the yedA gene or yddG gene is increased can also be used (U.S. Patent Application Publication Nos. 2003/0148473 A1 and 2003/0157667 A1).

Examples of parent strains which can be used to derive the L-tryptophan-producing bacteria also include strains in which one or more activities of the enzymes anthranilate synthase (trpE), phosphoglycerate dehydrogenase (serA), and tryptophan synthase (trpAB) are enhanced. The anthranilate synthase and phosphoglycerate dehydrogenase are both subject to feedback inhibition by L-tryptophan and L-serine, and therefore a mutation desensitizing the feedback inhibition may be introduced into these enzymes. Specific examples of strains having such a mutation include a *E. coli* SV164 which harbors desensitized anthranilate synthase and a transformant strain obtained by introducing, into the *E. coli* SV164, the plasmid pGH5(WO 94/08031), which contains a mutant serA gene encoding feedback inhibition-desensitized phosphoglycerate dehydrogenase.

Examples of parent strains for deriving the L-tryptophan-producing bacteria also include strains into which the tryptophan operon containing a gene encoding desensitized anthranilate synthase has been introduced (Japanese Patent Laid-open Nos. 57-71397, 62-244382, U.S. Pat. No. 4,371,614). Moreover, L-tryptophan-producing ability may be imparted by enhancing expression of a gene which encodes tryptophan synthase, among tryptophan operons (trpBA). The tryptophan synthase includes α and β subunits which are encoded by trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains which can be used to derive L-proline-producing bacteria include, but are not limited to, strains belonging to the genus *Escherichia*, such as *E. coli* 702ilvA (VKPM B-8012) which is deficient in the ilvA gene and is able to produce L-proline (European Patent No. 1172433).

The bacterium may be improved by enhancing the expression of one or more genes involved in L-proline biosynthesis. Examples of such genes for L-proline producing bacteria include the proB gene encoding glutamate kinase of which feedback inhibition by L-proline is desensitized (German Patent No. 3127361). In addition, the bacterium may be improved by enhancing the expression of one or more genes encoding proteins excreting L-amino acid from bacterial cell. Examples of such genes are b2682 and b2683 genes (ygaZH genes) (European Patent Laid-open No. 1239041 A2).

Examples of bacteria belonging to the genus *Escherichia*, which have an activity to produce L-proline include the following *E. coli* strains: NRRL B-12403 and NRRL B-12404 (British Patent No. 2075056), VKPM B-8012 (Russian Patent Application No. 2000124295), plasmid mutants described in German Patent No. 3127361, plasmid mutants described by Bloom F. R. et al (The 15th Miami winter symposium, 1983, p. 34), and the like.

L-Arginine-Producing Bacteria

Examples of parent strains which can be used to derive L-arginine-producing bacteria include, but are not limited to, strains belonging to the genus *Escherichia*, such as *E. coli* strain 237 (VKPM B-7925) (U.S. Patent Application Publication No. 2002/058315 A1) and its derivative strains harboring mutant N-acetylglutamate synthase (Russian Patent Application No. 2001112869), *E. coli* strain 382 (VKPM B-7926) (European Patent Laid-open No. 1170358A1), an arginine-producing strain into which argA gene encoding N-acetylglutamate synthetase is introduced (European Patent Laid-open No. 1170361A1), and the like.

Examples of parent strains which can be used to derive L-arginine producing bacteria also include strains in which expression of one or more genes encoding an L-arginine biosynthetic enzyme is/are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Example of parent strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon can be disrupted so that threonine deaminase activity is decreased.

Examples of parent strains which can be used to derive L-valine-producing bacteria also include mutant strains having a mutation of amino-acyl t-RNA synthetase (U.S. Pat. No. 5,658,766). For example, *E. coli* VL1970, which has a mutation in the ileS gene encoding isoleucine tRNA synthetase, can be used. E. coli VL1970 was deposited at the Russian National Collection of Industrial Microorganisms (VKPM) (Russia, 113545 Moscow, 1 Dorozhny Proezd, 1) on Jun. 24, 1988 under accession number VKPM B-4411.

Furthermore, mutants requiring lipoic acid for growth and/or lacking H$^+$-ATPase can also be used as parent strains (WO96/06926).

L-Isoleucine-Producing Bacteria

Examples of parent strains which can be used to derive L-isoleucine-producing bacteria include, but are not limited to, mutant strains having resistance to 6-dimethylaminopurine (Japanese Patent Laid-open No. 5-304969), mutant strains having resistance to an isoleucine analogue such as thiaisoleucine and isoleucine hydroxamate, and mutant strains additionally having resistance to DL-ethionine and/or arginine hydroxamate (Japanese Patent Laid-open No. 5-130882). In addition, recombinant strains transformed with a gene encoding a protein involved in L-isoleucine biosynthesis, such as threonine deaminase and acetohydroxate synthase, can also be used as parent strains (Japanese Patent Laid-open No. 2-458, French Patent No. 0356739, and U.S. Pat. No. 5,998,178).

<1-2> Enhancement of kdp System

Exemplary microorganisms of the present invention can be obtained by modifying a microorganism belonging to the family Enterobacteriaceae which is able to produce an L-amino acid as described above so that the kdp system is enhanced. However, the ability to produce an L-amino acid may be imparted after the microorganism is modified so that the kdp system is enhanced.

The kdp system can be enhanced by a modification which increases expression of the kdp operon or one or more genes on the kdp operon, and such increase of expression may be based on enhancement of expression of an endogenous gene by modification of an expression control region such as modification of a promoter or the like, or enhancement of expression of an exogenous gene by introduction of a plasmid containing the operon or any of the genes or the like. These methods may be performed in combination. The kdp system can also be enhanced by increasing translation of the kdp operon or any of the genes on the kdp operon.

The term "kdp system" means a P type ATPase (potassium-transporting P-type ATPase) which acts on the high-affinity potassium transport system (EC 3.6.3.12).

The phrase "modified so that the kdp system is enhanced" means that the aforementioned potassium transport by the P type ATPase is enhanced, more specifically, that the microorganism is modified so that the P type ATPase activity thereof is enhanced. This means, for example, that number of the molecules of the P type ATPase protein per cell is increased as compared to that of the parent strain or a wild-type strain, or that the activity of the P type ATPase per molecule is increased as compared to that of the parent strain or a wild-type strain. The modification is performed so that the P type ATPase activity per cell is improved to, for example, 150% or more, in another example 200% or more, in another example 300% or more, of the activity of the parent strain or a wild-type strain. The wild-type microorganism belonging to the family Enterobacteriaceae used as a reference for the comparison is, for example, Escherichia coli MG1655 (ATCC 47076), Pantoea ananatis AJ13355 (FERM BP-6615), or the like.

Increase of expression of the kdp operon can be confirmed by comparing the amount of mRNA thereof with that of a wild-type or non-modified strain. Examples of the method for confirming the expression include Northern hybridization and RT-PCR (Molecular Cloning, Cold Spring Harbor Laboratory Press, Cold Spring Harbor, USA, 2001). The degree of the increase in the expression is not particularly limited so long as it increases as compared to that of a wild-type strain or non-modified strain. However, it is desirably increased, for example, 1.5 times or more, in another example 2 times or more, in another example 3 times or more, as compared to that of a wild-type strain or non-modified strain.

The P type ATPase activity can be measured by, for example, extracting the kdp system from a microorganism, purifying it (refer to Siebers, A. et al., Eur. J. Biochem., 178, 131 (1988)) and measuring the P type ATPase activity of the purified kdp system (refer to Arnold, A. et al., Anal. Biochem., 71, 209 (1976)).

The kdp system consists of three subunits encoded by the kdp operon, and as for E. coli, the following annotations are given to the subunit genes:

kdpA: ATPase of high-affinity potassium transport system, A chain
kdpB: ATPase of high-affinity potassium transport system, B chain
kdpC: P-type ATPase, high-affinity potassium transport system, C chain The "kdp operon" is a gene cluster encoding A, B and C subunits of the P type ATPase described above, in which the A subunit is encoded by the kdpA gene, the B subunit is encoded by the kdpB gene, and the C subunit is encoded by the kdpC gene. The kdp operon may contain a gene other than the kdpA, kdpB and kdpC genes.

The nucleotide sequence of the kdp operon of Escherichia coli is shown in SEQ ID NO: 1. This operon contains the following six genes, and the coding regions (including stop codon) of the genes in SEQ ID NO: 1 are as follows. The amino acid sequences encoded by kdpA, kdpB, kdpC, kdpD and kdpE are shown in SEQ ID NOS: 2 to 6, respectively.

kdpF: 457 to 546
kdpA: 546 to 2219
kdpB: 2242 to 4290
kdpC: 4299 to 4871
kdpD: 4864 to 7548
kdpE: 7545 to 8222

The nucleotide sequence of the kdp operon of Pantoea ananatis is shown in SEQ ID NO: 7. This operon contains the following four genes, and the coding regions (including stop codon) of the genes in SEQ ID NO: 7 are as follows. The amino acid sequences encoded by kdpA, kdpB, kdpC and kdpD are shown in SEQ ID NOS: 8 to 11, respectively.

kdpA: 543 to 2225
kdpB: 2228 to 4273
kdpC: 4284 to 4853
kdpD: 4867 to 7542

Furthermore, the nucleotide sequence of the kdpE gene of Pantoea ananatis and the amino acid sequence encoded by this gene are shown in SEQ ID NOS: 12 and 13, respectively.

In this specification, the proteins encoded by kdpA, kdpB, kdpC, kdpD and kdpE may be indicated as KdpA, KdpB, KdpC, KdpD and KdpE, respectively.

Alignments of the amino acid sequences of KdpA, KdpB and KdpC of Pantoea ananatis and Escherichia coli are shown in FIGS. 6 to 8. The consensus of the sequences of Pantoea ananatis and Escherichia coli are shown in the lower rows of the alignments. Moreover, consensus sequences of KdpA, KdpB and KdpC are shown in SEQ ID NOS: 57 to 59, respectively.

Homologies of KdpA, KdpB and KdpC of Pantoea ananatis and Escherichia coli are 75.36%, 81.35% and 59.57%, respectively.

As for Escherichia bacteria, the kdpA gene is registered at GenBank NP_415226.1 Reports potassium-transpo . . . To [gi:16128674], the kdpB gene at NP_415225. Reports potassium-transpo . . . [gi:16128673], the kdpC gene at NP_415224. Reports potassium-transpo . . . [gi:16128672], the kdpD gene at NP_415223. Reports fused sensory his . . . [gi:16128671], and the kdpE gene at NP_415222. Reports DNA-binding respo . . . [gi:16128670].

Furthermore, the kdp operon may be cloned from a microorganism belonging to the family Enterobacteriaceae such as Escherichia, Pantoea, Enterobacter, Klebsiella, Serratia, Erwinia and Yersinia bacteria on the basis of homologies to the genes exemplified above.

An exemplary kdp operon which can be used in the present invention includes the kdp operon and flanking regions thereof including an expression control region located upstream from the operon. The operon and flanking regions can be obtained by PCR (polymerase chain reaction, refer to White, T. J. et al., Trends Genet., 5, 185 (1989)) using primers prepared on the basis of an already elucidated nucleotide sequence of a microorganism belonging to the family Enterobacteriaceae and chromosomal DNA of a microorganism belonging to the family Enterobacteriaceae as the template. Homologues of the kdp operon of other microorganisms can also be obtained in a similar manner.

A kdp operon homologue means a gene encoding a P type ATPase, which incorporates potassium ions, derived from another microorganism and showing a high homology to the kdp operon of Escherichia coli or Pantoea ananatis. The kdpA gene, kdpB gene and kdpC gene derived from another microorganism means those showing homologies of no less than 80%, 90%, 95%, or 97%, to the total amino acid sequences of SEQ ID NOS: 2, 3, 4, 8, 9 and 10 and encoding the subunits constituting a protein having the P type ATPase activity.

Each of genes may encode a conservative variant having amino acid sequences of SEQ ID NOS: 2, 3, 4, 8, 9 or 10, but which includes a substitution, deletion, insertion, or addition of one or several amino acid residues at one or several positions so long as the activity of P-type ATPase constituted from these subunits are not degraded. Although the number meant by the term "several" may differ depending on position in the three-dimensional structure or types of amino acid residues of the proteins, it may be 1 to 20, for example, and in another example 1 to 10, and in another example 1 to 5. Substitutions, deletions, insertions, additions, inversions and the like of the amino acids described above include those caused by mutations which are naturally occurring due to individual differences or differences in species of microorganisms.

These substitutions may be conservative substitutions that are neutral and do not effect the function. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp and Glu, if it is an acidic amino acid; and between Ser and Thr, if it is an amino acid having a hydroxyl group. Specific examples of conservative substitutions include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val.

Furthermore, the kdp operon using codons that function in the chosen host microorganism may also be used, since the degeneracy of the gene varies depending on the host microorganism. Similarly, so long as L-amino acid production can be improved by amplifying the kdp operon, the kdp operon may be extended or shortened at either the N-terminus and/or C-terminus of each subunit encoded by the operon by, for example, 50 or less, in another example 20 or less, in another example 10 or less, and in another example 5 or less, of the number of amino acid residues. More specifically, each subunit may have an amino acid sequence which is shortened by 5 to 50 amino acid residues at either the N-terminus and/or the C-terminus in the amino acid sequence of SEQ ID NOS: 2, 3, 4, 8, 9 or 10.

Moreover, the kdp operon may be a DNA which hybridizes under stringent conditions with the nucleotide sequence shown in SEQ ID NO: 1 or 7, or a sequence complementary to each of the coding region in the nucleotide sequence of SEQ ID NO: 1 or 7, or a probe which can be prepared from these sequences, and which encodes the kdp system, that is, a protein having P type ATPase activity to incorporate potassium ions.

The "stringent conditions" mean conditions where a so-called specific hybrid is formed and a non-specific hybrid is not formed. It is difficult to clearly define the conditions with numerical values, but examples thereof include conditions where DNAs having high homology, for example, homology of no less than 70%, 80%, 90%, 95%, or 97%, hybridize to each other and DNAs having a homology less than the value do not hybridize with each other; and specifically include conditions corresponding to a salt concentration and temperature of washing typical Southern hybridization, e.g., 1×SSC, 0.1% SDS, in another example 0.1×SSC, 0.1% SDS, at 60° C.

The probe may be a probe having a partial sequence of the kdp operon. Such a probe can be prepared by PCR using oligonucleotides based on the nucleotide sequence of the gene according to well-known methods as primers, and a DNA fragment containing the gene as the template. When a DNA fragment of a length of about 300 bp is used as the probe, washing after hybridization under the aforementioned conditions may be, for example, washing once or twice or three times under the conditions of 50° C., 2×SSC, and 0.1% SDS.

A gene homologous to the kdp operon can be obtained by, for example, modifying the coding region in the nucleotide sequence of SEQ ID NO: 1 or 7 by site-specific mutagenesis so that the encoded protein contains substitutions, deletions, insertions or additions of amino acid residues at a specific site. Such a gene can also be obtained by the following conventionally known mutagenesis. As for the mutagenesis, an operon encoding a highly active kdp system can be obtained by artificially introducing a mutation into the kdp operon by treating the nucleotide sequences of SEQ ID NO: 1 or 7, or a coding region in these nucleotide sequences in vitro with hydroxylamine or the like, or treating a microorganism having the gene, for example, such a microorganism belonging to the family Enterobacteriaceae, with ultraviolet irradiation or a mutagen used for usual mutagenesis such as N-methyl-N'-nitro-N-nitrosoguanidine (NTG) or ethyl methanesulfonate (EMS), or by gene recombination based on error-prone PCR (Cadwell, R. C., PCR Meth. Appl., 2, 28 (1992)), DNA shuffling (Stemmer, W. P., Nature, 370, 389 (1994)), or StEP-PCR (Zhao, H., Nature Biotechnol., 16, 258 (1998)). Whether a homologue of the kdp operon encodes the P type ATPase can be confirmed by, for example, introducing the gene into a microorganism belonging to the family Enterobacteriaceae and having L-amino acid-producing ability and determining whether the L-amino acid producing ability is improved or measuring the P type ATPase activity by the aforementioned method.

The above descriptions concerning variants and homologues can also be applied to the kdpD gene and kdpE gene described later.

The modification of a microorganism belonging to the family Enterobacteriaceae so that expression of the kdp operon or one or more genes on the operon is increased can be attained by the aforementioned method of modifying a bacterium so that the expression of a target gene is enhanced. Namely, by increasing the number of the kdp operon or each gene on the operon, and/or replacing the expression control sequence of the operon with a stronger expression control sequence, or by controlling each gene on the operon with a stronger expression control sequence, expression of the operon or each gene can be enhanced. For example, enhancement of expression of the genes on the kdp operon may be performed for the entire operon or each gene, and in another example, the enhancement may be performed for the entire operon. When expression is enhanced for each individual gene, the gene to be enhanced may be any one of the genes constituting the kdp operon, but in another example expression of at least one or more kinds of genes among kdpA, kdpB, and kdpC genes are enhanced, and in another example, expression of all the kdpA, kdpB and kdpC genes are enhanced.

The kdp system can also be enhanced by modifying the spacer sequence between the ribosome binding site (RBS) and start codon of each gene so that translation of each gene constituting the kdp operon is increased.

Furthermore, it is known that expression of the kdp operon is controlled by the binary control system KdpDE encoded by the kdpD gene and the kdpE gene (J. Bacteriol., 1992 April, 174 (7):2152-59), and expression of the kdp operon can also be increased by increasing expression of the kdpD gene and the kdpE gene.

<2> Method for Producing L-Amino Acid

By culturing an exemplary microorganism of the present invention in a medium to produce and accumulate an L-amino acid in the medium and collecting the L-amino acid from the medium, an L-amino acid can be produced.

As the medium used for the culture, a typical medium containing a carbon source, nitrogen source, and mineral salts as well as organic trace nutrients such as amino acids and vitamins as required may be used. Either a synthetic medium or a natural medium may be used. Any kind of carbon source and nitrogen source may be used so long as they can be utilized by the chosen strain.

Sugars such as glucose, glycerol, fructose, sucrose, maltose, mannose, galactose, starch hydrolysates and molasses can be used as the carbon source. In addition, organic acids such as acetic acid and citric acid, and alcohols such as ethanol can also be used each alone or in combination with other carbon sources. Ammonia, ammonium salts such as ammonium sulfate, ammonium carbonate, ammonium chloride, ammonium phosphate and ammonium acetate, nitric acid salts and so forth can be used as the nitrogen source. Amino acids, vitamins, fatty acids, nucleic acids, those containing those substances such as peptone, casamino acid, yeast extract and soybean protein decomposition product and so forth can be used as the organic trace nutrients. When an auxotrophic mutant strain that requires an amino acid or the like for its growth is used, the required nutrient may be supplemented.

In particular, when a liquid medium prepared so as to satisfy a condition for precipitating L-glutamic acid is used, addition of pantothenic acid to the medium provides more efficient precipitation of L-glutamic acid (WO2004/111258). As inorganic salts, phosphoric acid salts, magnesium salts, calcium salts, iron salts, manganese salt and so forth can be used.

The culture may be performed as an aerobic culture, while the fermentation temperature is controlled to be 20 to 45° C., and pH to be 3 to 9. When the pH decreases during the culture, calcium carbonate may be added, or culture is neutralized with an alkaline substance such as ammonia gas. The target L-amino acid is accumulated in the culture medium after, for example, 10 to 120 hours of culture under such conditions as described above.

Moreover, the culture can be performed by precipitating L-glutamic acid in a medium by using, as the medium, a liquid medium adjusted to satisfy a condition under which L-glutamic acid is precipitated. Examples of the conditions under which L-glutamic acid is precipitated include, for example, pH of 5.0 to 4.0, in another example 4.5 to 4.0, in another example 4.3 to 4.0, in another example 4.0.

When L-glutamic acid is precipitated in the medium, preliminary addition of crystals of L-glutamic acid or L-lysine as seed crystals can provide more efficient crystallization (European Patent No. 1233069, European Patent Laid-open No. 1624069).

Collection of the L-amino acid from the culture broth after the culture may be performed by a known collection method. For example, after the cells were removed from the culture medium, L-amino acid can be collected by concentrating the medium to crystallize the L-amino acid, ion exchange chromatography, or the like. When the culture is performed under conditions so that L-glutamic acid is precipitated, L-glutamic acid which precipitates in the medium can be collected by centrifugation or filtration. In this case, L-glutamic acid which dissolves in the medium may be precipitated and then separated together with already precipitated L-glutamic acid.

When a basic amino acid is produced, a method may be used in which pH of the medium during culture is controlled to be 6.5 to 9.0, and the pH of the medium after completion of the culture is controlled to be 7.2 to 9.0. Furthermore, the pressure in the fermentation tank can be controlled during fermentation to be positive, or carbon dioxide or a mixed gas containing carbon dioxide can be added to the medium so that there is period when bicarbonate ions and/or carbonate ions are present in a concentration of at least 2 g/L in the culture medium during the culture, and these bicarbonate ions and/or carbonate ions serve as counter ions to the cations largely of the basic amino acid, and the target basic amino acid is then collected (refer to Japanese Patent Laid-open No. 2002-065287, U.S. Patent Application Publication No. 2002025564).

EXAMPLES

Hereinafter, the present invention will be described in more detail by referring to the following non-limiting examples.

Reference Example 1

Construction of a *Pantoea ananatis* Strain which is Resistant to the λ Red Gene Product To amplify the kdp operon in *Pantoea ananatis*, a recipient strain was constructed which carries out the method called "Red-driven integration" or "Red-mediated integration" (Proc. Natl. Acad. Sci. USA, 97, 6640-6645 (2000)).

First, the novel helper plasmid RSF-Red-TER which expresses the gam, bet and exo genes of λ (henceforth referred to as "λ Red genes") was constructed (FIG. 1). The details thereof will be described in Reference Example 2.

This plasmid can be used in a wide range of hosts having different genetic backgrounds. This is because 1) this plasmid has the replicon of the RSF1010 wide host spectrum plasmid (Scholz, et al., 1989; Buchanan-Wollaston et al., 1987), which is stably maintained by many types of gram negative and gram positive bacteria, and even plant cells, 2) the λ Red genes, gam, bet and exo genes, are under the control of the PlacUV5 promoter, which is recognized by the RNA polymerases of many types of bacteria (for example, Brunschwig, E. and Darzins, A., Gene, 111, 1, 35-41 (1992); Dehio, M. et al, Gene, 215, 2, 223-229 (1998)), and 3) the autoregulation factor $P_{lacUV5}$-lacI and the ρ-non-dependent transcription terminator (TrrnB) of the rrnB operon of *Escherichia coli* lower the basal expression level of the λ Red genes (Skorokhodova, A. Yu et al, Biotekhnologiya (Rus), 5, 3-21 (2004)). Furthermore, the RSF-Red-TER plasmid contains the levansucrase gene (sacB), and by using this gene, the plasmid can be collected from cells in a medium containing sucrose.

In *Escherichia coli*, the frequency of integration of a PCR-generated DNA fragment along with the short flanking region provided by the RSF-Red-TER plasmid is as high as the frequency obtained when using the pKD46 helper plasmid (Datsenko, K. A., Wanner, B. L., Proc. Natl. Acad. Sci. USA, 97, 6640-6645 (2000)). However, expression of the λ Red genes is toxic to *Pantoea ananatis*. Cells transformed with the RSF-Red-TER helper plasmid grow extremely slowly in LB medium containing IPTG (isopropylβ-D-thiogalactopyranoside, 1 mM) and an appropriate antibiotic (25 μg/ml of chloramphenicol or 40 µg/ml of kanamycin), and the efficiency of λ Red-mediated recombination is extremely low ($10^{-8}$), if observed at all.

A variant strain of *Pantoea ananatis* which is resistant to expression of all three of the λ Red genes was selected. For this purpose, the RSF-Red-TER plasmid was introduced into the *Pantoea ananatis* SC17 strain (U.S. Pat. No. 6,596,517) by electroporation. After an 18 hour culture, about $10^6$ transformants were obtained, and among these, 10 clones formed colonies of a large size, and all the remainder formed extremely small colonies. After an 18 hour culture, the large colonies were about 2 mm, and the small colonies were about 0.2 mm. Whereas the small colonies did not grow any more even when the culture was extended another 24 hours, the large colonies continued to grow. One of the large colony *Pantoea ananatis* mutant strains which was resistant to expression of all three of the λ Red genes (gam, bet, and exo) was used for further analysis.

The RSF-Red-TER plasmid DNA was isolated from one clone of the large colony clones, and from several clones of the small colony clones, and transformed again into *Escherichia coli* MG1655 to examine the ability of the plasmid to synthesize an active Red gene product. By a control experiment for Red-dependent integration in the obtained transformants, it was demonstrated that only the plasmid isolated from the large colony clone induced expression of the λ Red genes required for the Red-dependent integration. In order to investigate whether the Red-mediated integration occurs in the selected large colony clone, electroporation was performed using a linear DNA fragment produced by PCR. This fragment was designed so that it contains a $Km^R$ marker and a flanking region of 40 bp homologous to the hisD gene. This fragment is integrated into the hisD gene of *Pantoea ananatis* at the SmaI recognition site. Two small colony clones were used as control. The nucleotide sequence of the hisD gene of *Pantoea ananatis* is shown in SEQ ID NO: 14. For PCR, the oligonucleotides of SEQ ID NOS: 15 and 16 were used as primers, and the pMW118-(λatt-$Km^r$-λatt) plasmid was used as the template. The two small colony clones which were not resistant to the λ Red genes were used as a control. Construction of the pMW118-(λattL-$Km^r$-λattR) plasmid will be explained in detail in Reference Example 3.

The RSF-Red-TER plasmid can induce expression of the Red genes by the lacI gene carried on the plasmid. Two kinds of induction conditions were investigated. In the first group, IPTG (1 mM) was added 1 hour before the electroporation, and in the second group, IPTG was added at the start of the culture to prepare cells in which electroporation is possible. The growth rate of the cells harboring RSF-Red-TER derived from the large colony clone was not significantly lower than that of a strain not having the SC17 plasmid. The addition of IPTG only slightly decreased the growth rate of these cultures. On the other hand, the progeny of the small colony clones grew extremely slowly even without the addition of IPTG, and after induction, growth was substantially arrested. After electroporation of the cells of the progeny of the large colony clone, many $Km^R$ clones grew (18 clones after a short induction time, and about 100 clones after an extended induction time). All of the 100 clones that were investigated had a His⁻ phenotype, and about 20 clones were confirmed by PCR to have the expected structure of the chromosome in the cells. On the other hand, even when electroporation was performed with the progeny of the small colony clones, an integrated strain was not obtained.

The obtained large colony clone was grown on a plate containing 7% sucrose to eliminate the plasmid, and transformed again with RSF-Red-TER. The strain without the plasmid was designated SC17(0). This strain was deposited at the Russian National Collection of Industrial Microorganisms (VKPM, GNII Genetica (1 Dorozhny proezd., 1 Moscow 117545, Russia) on Sep. 21, 2005, and assigned an accession number of VKPM B-9246.

All the clones which grew after the aforementioned re-transformation were like the parent strain clone SC17(0). The Red-mediated integration experiment was performed in the SC17(0) strain re-transformed with the RSF-Red-TER plasmid. Three of the independent transformants were investigated using the same DNA fragment as that used for the previous experiment. The short induction time (1 hour before electroporation) was employed. $Km^R$ clones exceeding ten clones grew in each experiment. All the examined clones had the His⁻ phenotype. In this way, a mutant strain designated SC17(0) which is resistant to the expression of the λ Red genes was selected. This strain can be used as a recipient strain suitable for the Red-dependent integration into the *Pantoea ananatis* chromosome.

Reference Example 2

Construction of Helper Plasmid RSF-Red-TER

Figure 2:
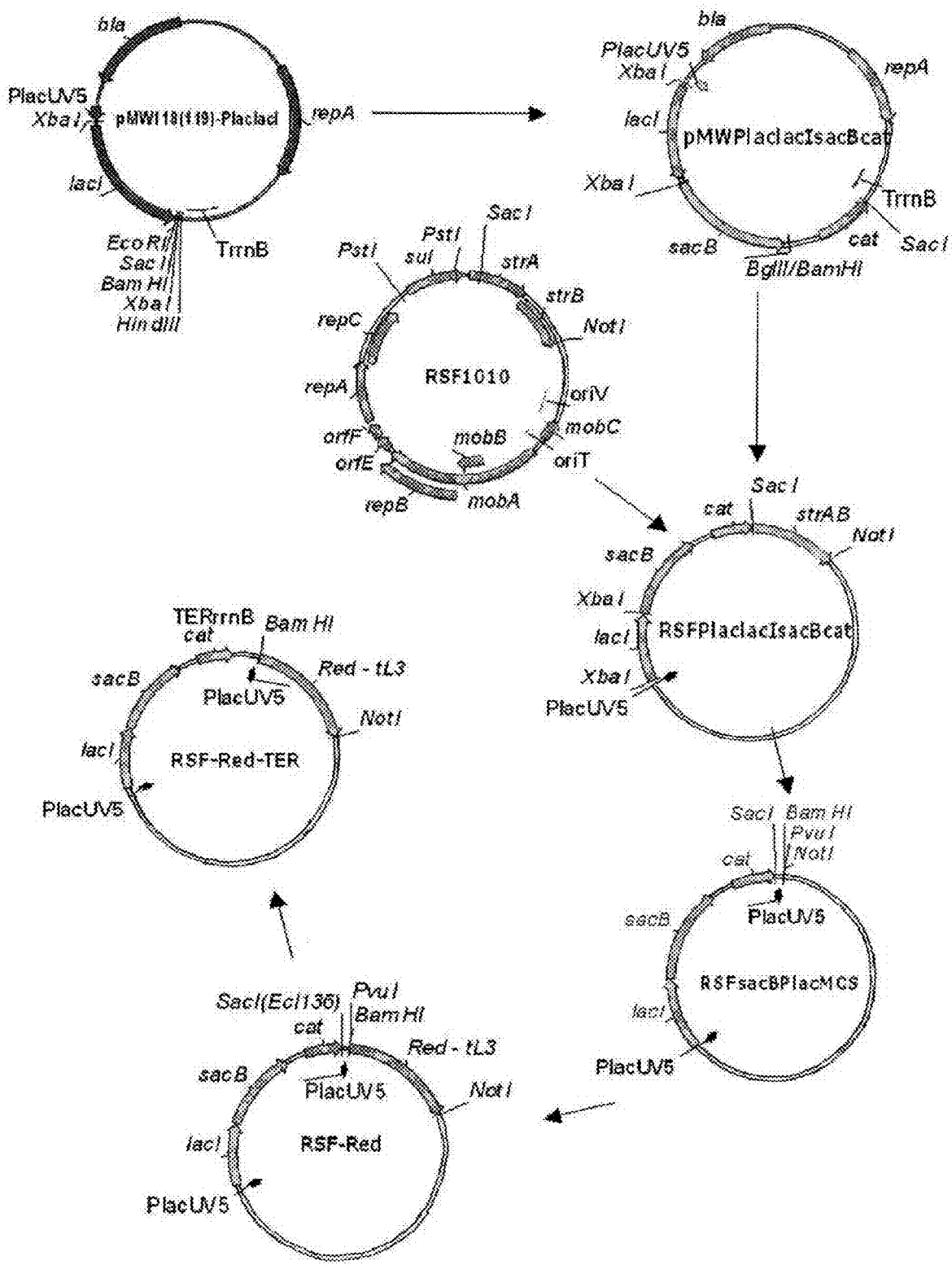
FIG. 2 shows the construction of the helper plasmid RSF-Red-TER.

The scheme for constructing the helper plasmid RSF-Red-TER is shown in FIG. 2.

As the first step in the construction, an RSFsacBPlacMCS vector was designed. For this purpose, DNA fragments containing the cat gene of the pACYC184 plasmid and the structural region of the sacB gene of *Bacillus subtilis* were amplified by PCR using the oligonucleotides of SEQ ID NOS: 17 and 18, and 19 and 20, respectively. These oligonucleotides contained BglII, SadI, XbaI and BamHI restriction enzyme sites, which are required and convenient for further cloning, in the 5' end regions, respectively. The obtained sacB fragment of 1.5 kb was cloned into the previously obtained pMW119-$P_{lac}$lacI vector at the XbaI-BamHI site. This vector was constructed in the same manner as that described for the pMW118-$P_{lac}$lacI vector (Skorokhodova, A. Yu et al, Biotekhnologiya (Rus), 5, 3-21 (2004)). However, this vector contained a polylinker moiety derived from pMW219 instead of the pMW218 plasmid.

Then, the aforementioned cat fragment of 1.0 kb was treated with BglII and SacI, and cloned into the RSF-$P_{lac}$lacIsacB plasmid obtained in the previous step at the BamHI-SacI site. The obtained plasmid pMW-$P_{lac}$lacIsacBcat contained the PlacUV5-lacI-sacB-cat fragment. In order to subclone this fragment into the RSF1010 vector, pMW-$P_{lac}$lacIsacBcat was digested with BglII, blunt-ended with DNA polymerase I Klenow fragment, and successively digested with SacI. A 3.8 kb BglII-SacI fragment of the pMWP$_{lac}$lacIsacBcat plasmid was eluted from a 1% agarose gel, and ligated with the RSF1010 vector which had been treated with PstI and SacI. *Escherichia coli* TG1 was transformed with the ligation mixture, and plated on the LB medium containing chloramphenicol (50 mg/L). The plasmids isolated from the grown clones were analyzed with restriction enzymes to obtain a RSFsacB plasmid. In order to construct an RSFsacB$P_{lac}$MCS vector, a DNA fragment containing the $P_{lacUV5}$ promoter was amplified by PCR using the oligonucleotides of SEQ ID NOS: 21 and 22 as primers and the pMW119-$P_{lac}$lacI plasmid as the template. The obtained fragment of 146 bp was digested with SacI and NotI, and ligated with the SacI-NotI large fragment of the RSFsacB plasmid. Then, by PCR using the oligonucleotides of SEQ ID NOS: 23 and 24 as primers, and the pKD46 plasmid (Datsenko, K. A., Wanner, B. L., Proc. Natl. Acad. Sci. USA, 97, 6640-6645 (2000)) as the template, a DNA fragment of 2.3 kb containing the λRedαβγ genes and the transcription terminator tL3 was amplified. The obtained fragment was cloned into the RSFsacBP$_{lac}$MCS vector at the PvuI-NotI site. In this way, the RSFRed plasmid was designed.

In order to eliminate read through transcription of the Red genes, a ρ-dependent transcription terminator of the rrnB operon of *Escherichia coli* was inserted at a position between the cat gene and the P$_{lacUV5}$ promoter. For this purpose, a DNA fragment containing the P$_{lacUV5}$ promoter and the TrrnB terminator was amplified by PCR using the oligonucleotides of SEQ ID NOS: 25 and 22 as primers and the chromosome of *Escherichia coli* BW3350 as the template. These obtained fragments were treated with KpnI and ligated. Then, the 0.5 kb fragment containing both P$_{lacUV5}$ and TrrnB was amplified by PCR using the oligonucleotides of SEQ ID NOS: 22 and 26 as primers. The obtained DNA fragment was digested with EcoRI, blunt-ended by a treatment with DNA polymerase I Klenow fragment, digested with BamHI, and ligated with the Ec1136II-BamHI large fragment of the RSF-sacBPlacMCS vector. The obtained plasmid was designated RSF-Red-TER.

Reference Example 3

Construction of pMW118-(λattL-Km$^r$-λattR) Plasmid

The pMW118-(λattL-Km$^r$-λattR) plasmid was constructed from the pMW118-attL-Tc-attR (WO2005/010175) plasmid by replacing the tetracycline resistance marker gene with the kanamycin resistance gene of the pUC4K plasmid. For that purpose, the EcoRI-HindIII large fragment from pMW118-attL-Tc-attR plasmid was ligated to two fragments from the pUC4K plasmid: HindIII-PstI fragment (676 bp) and EcoRI-HindIII fragment (585 bp). Basic pMW118-attL-Tc-attR was obtained by ligation of the following four fragments.

1) The BglII-EcoRI fragment (114 bp) including attL (SEQ ID NO: 29) which was obtained by PCR amplification of the region corresponding to attL of the *Escherichia coli* W3350 (containing λ prophage) chromosome using the primers P1 and P2 (SEQ ID NOS: 27 and 28) (these primers contained the subsidiary recognition sites for BglII and EcoRI).

2) The PstI-HindIII fragment (182 bp) including attR (SEQ ID NO: 32) which was obtained by PCR amplification of the region corresponding to attR of the *Escherichia coli* W3350 (containing λ prophage) chromosome using the primers P3 and P4 (SEQ ID NOS: 30 and 31) (these primers contained the subsidiary recognition sites for PstI and HindIII).

3) The BglII-HindIII large fragment (3916 bp) of pMW118-ter_rrnB. The plasmid pMW118-ter_rrnB was obtained by ligation of the following three DNA fragments:
  The large DNA fragment (2359 bp) including the AatII-EcoRI fragment of pMW118 that was obtained by digesting pMW118 with EcoRI, treating with DNA polymerase I Klenow fragment, and then digesting with AatII;
  The small AatII-BglII fragment (1194 bp) of pUC19 including the bla gene for ampicillin resistance (AP$^R$), which was obtained by PCR amplification of the corresponding region of the pUC19 plasmid using the primers P5 and P6 (SEQ ID NOS: 33 and 34) (these primers contained the subsidiary recognition sites for PstI, AatII and BglII);
  The small BglII-PstIpol fragment (363 bp) of the transcription terminator ter_rrnB, which was obtained by PCR amplification of the corresponding region of the *Escherichia coli* MG1655 chromosome using the primers P7 and P8 (SEQ ID NOS: 35 and 36) (these primers contained the subsidiary recognition sites for PstI, BglII and PstI).

4) The small EcoRI-PstI fragment (1388 bp) (SEQ ID NO: 37) of pML-Tc-ter_thrL including the tetracycline resistance gene and the ter_thrL transcription terminator; the pML-Tc-ter_thrL plasmid was obtained by the following two steps:
  the pML-ter_thrL plasmid was obtained by digesting the pML-MCS plasmid (Mashko, S. V. et al., Biotekhnologiya (in Russian), 2001, no. 5, 3-20) with XbaI and BamHI, followed by ligation of the large fragment (3342 bp) with the XbaI-BamHI fragment (68 bp) carrying ter_thrL terminator obtained by PCR amplification of the corresponding region of the *Escherichia coli* MG1655 chromosome using the primers P9 and P10 (SEQ ID NOS: 38 and 39) (these primers contained the subsidiary recognition sites for PstI, XbaI and BamHI);
  the pML-Tc-ter_thrL plasmid was obtained by digesting the pML-ter_thrL plasmid with KpnI and XbaI followed by treatment with Klenow fragment of DNA polymerase I and ligated with the small EcoRI-Van91I fragment (1317 bp) of pBR322 including the tetracycline resistance gene (pBR322 was digested with EcoRI and Van91I and then treated with Klenow fragment DNA polymerase I).

Example 1

Acquisition of kdp Operon Promoter-Substituted Strain (1) Construction of Glutamic Acid-Producing Plasmid RSFPPG The plasmid RSFPPG was constructed in which the L-glutamic acid biosynthesis system genes, prpC gene (International Patent Publication WO2006/051660), ppc gene and gdhA gene (EP0999282A) were amplified.

The primer 1 (SEQ ID NO: 40) and the primer 2 (SEQ ID NO: 41) for amplifying a part of RSFCPG (EP1233068A) other than ORF of the gltA gene were designed. By using these primers and RSFCPG as the template, PCR was performed to obtain a fragment of about 14.9 kb. As for prpC, PCR was performed using the primer 3 (SEQ ID NO: 42) and the primer 4 (SEQ ID NO: 43) and the chromosomal DNA of the *E. coli* W3110 strain as the template to obtain a fragment of about 1.2 kb. Both the PCR products were treated with BglII and KpnI, ligated, and then used to transform the *E. coli* JM109 strain. All the colonies which grew were collected, and the plasmids were extracted from the colonies as a mixture. The *E. coli* ME8330 strain, which is a citrate synthase (CS) deficient strain, was transformed with the plasmid mixture, and the cell suspension was applied on M9 minimal medium (5 g of glucose, 2 mM magnesium sulfate, 3 g of monopotassium phosphate, 0.5 g of sodium chloride, 1 g of ammonium chloride and 6 g of disodium phosphate in 1 L of pure water) containing 50 mg/L of uracil and 5 mg/L of thiamine HCl. From the strains which grew, a plasmid was extracted and designated RSFPPG. This plasmid RSFPPG was introduced into the *Pantoea ananatis* NP106 strain, which is an L-glutamic acid-producing strain, to construct an L-glutamic acid-producing strain, NP106/RSFPPG (this strain is referred to as "NA1 strain").

The NP106 strain was obtained as follows. The *Pantoea ananatis* AJ13601 strain described above was cultured overnight at 34° C. in LBGM9 liquid medium with shaking, the medium was diluted so that 100 to 200 colonies will grow per plate, and then the diluted medium was applied to an LBGM9 plate containing 12.5 mg/L of tetracycline. The colonies which appeared were replicated on a LBGM9 plate containing 12.5 mg/L of tetracycline and 25 mg/L of chloramphenicol, and a strain which was sensitive to chloramphenicol was selected to obtain a strain from which pSTVCB was eliminated, which was designated G106S. The G106S strain was further cultured overnight at 34° C. in the LBGM9 liquid medium with shaking, the medium was diluted so that 100 to 200 colonies appear per plate, and then the diluted medium was applied to an LBGM9 plate without drugs. The colonies which grew were replicated on a LBGM9 plate containing 12.5 mg/L of tetracycline and a LBGM9 plate without drugs, and a strain which was sensitive to tetracycline was selected to obtain a strain from which RSFCPG was eliminated, which was designated NP106. The NP106 obtained as described above does not contain plasmids RSFCPG and pSTVCB, which are harbored by the AJ13601 strain.

Figure 3:
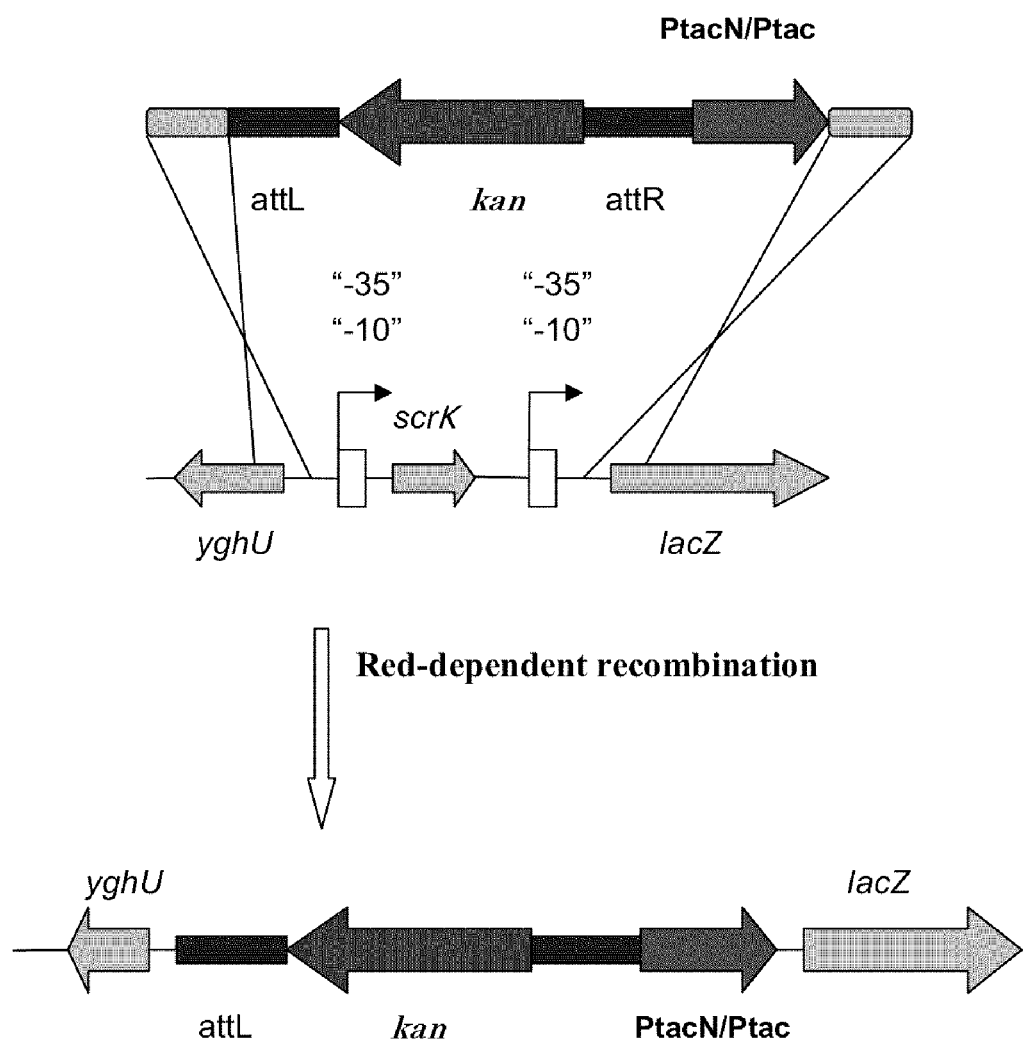
FIG. 3 shows the structure of the chromosome region of *P. ananatis* located upstream of the LacZ gene.

(2) Acquisition of Strain in which Promoter of kdp Operon was Replaced with tac Promoter i) Construction of a *P. ananatis* SC17(0) strain in which a sequence which has λattL-Km$^r$-λattR and Ptac promoter ligated downstream (λattL-Kmr-λattR-Ptac) was integrated upstream from lacZ gene The Ptac promoter was integrated into the chromosome of *P. ananatis* SC17(0) strain at a position upstream from the lacZ gene. The structure of the chromosome region of *P. ananatis* upstream from the LacZ gene is shown in FIG. 3. The nucleotide sequences of the yghU, scrK and lacZ genes of *Pantoea ananatis* are shown in SEQ ID NOS: 44, 45 and 46. The sequence of the −35 region of the Ptac promoter is ttgaca.

The Ptac promoter fragment was amplified by PCR using 5' primer 1 (SEQ ID NO: 47) and 3' primer 2 (SEQ ID NO: 48) corresponding to the Ptac promoter, and pDR540 plasmid (Pharmacia, Sweden) as the template. Both of the primers contained a BglII recognition sequence at the 5' end. The primer 2 contained 46 nucleotides of the 3' end part of Ptac, SD sequence, and a beginning part of the coding region of the lacZ gene.

A DNA fragment containing a removable Km resistance gene flanking the attL and attR sites of λ was also amplified by PCR using pMW118-(λattL-Km$^r$-λattR) as the template, and primer 3 (SEQ ID NO: 49) and primer 4 (SEQ ID NO: 50). The obtained fragment had a BglII recognition site for ligation with the tac promoter fragment at one end, and a site corresponding to a sequence homologous to the *Pantoea ananatis* chromosome located upstream of the scrK gene for integration into the bacterial genome at the other end (FIG. 3). Two of the PCR product fragments were treated with BglII, and ligated in vitro with T4 DNA ligase.

The ligation reaction mixture was used for λ-dependent integration into the *Pantoea ananatis* chromosome. The helper plasmid RSF-Red-TER was used as a carrier of λ phage Red genes. In order to obtain electro-competent cells of *Pantoea ananatis*, the SC17(0) strain was transformed with the RSF-Red-Ter plasmid, and cultured overnight at 34° C. in LB medium containing 50 µg/ml of chloramphenicol. Then, the culture broth was diluted 100 times with fresh LB medium containing 50 µg/ml of chloramphenicol, and the cells grew at 34° C. under aeration until OD$_{600}$ became 0.3. Then, 1 mM IPTG was added, and culture was continued until OD$_{600}$ became 0.7. A 10 mM sample was washed 3 times with an equal volume of deionized water, and the cells were suspended in 40 µl of 10% cold glycerol. Immediately before electroporation, 100 to 200 ng of in vitro-amplified DNA fragment dissolved in 5 µl of deionized water was added to the cell suspension. Electroporation was done by using a bacterium electroporation apparatus (BioRad, United States, Catalog number 165-2089, Version 2-89). The parameters of the pulse used were a field intensity of 20 kV/cm, and a pulse time of 5 milliseconds.

After the electroporation, 1 ml of LB medium supplemented with glucose (0.5%) was immediately added to the cell suspension. Then, the cells were allowed to grow at 34° C. for 2 hours under aeration, plated on LB solid medium containing 40 µg/ml of chloramphenicol, and incubated overnight at 34° C. The selected Km$^R$ integrant was streaked on an LB medium plate to which IPTG (1 mM) and sucrose (5 g/L) were added, and grown at 34° C. to allow it to form single colonies. In order to remove the RSF-Red-TER helper plasmid from the integrant, Km$^R$ and Cm$^S$ variants were isolated.

The chromosome structures of the selected Km$^R$ and Cm$^S$ colonies were confirmed by nucleotide sequencing.

ii) Substitution of the tac promoter with the kdp operon promoter

Two synthetic DNA primers shown in SEQ ID NOS: 51 and 52 were synthesized in a conventional manner. The primer shown in SEQ ID NO: 51 has a sequence which is homologous to the upstream region of the kdp operon of *Pantoea ananatis*, and is followed by a sequence of which is homologous to the 5' end of λattL-Km$^r$-λattR-Ptac. The primer of SEQ ID NO: 52 includes a 5' end complementary sequence containing the first start codon of the kdp operon of *Pantoea ananatis*, which is followed by a complementary sequence to the 3' end of λ attL-Km$^r$-λattR-Ptac. By performing PCR using these primers and the chromosomal DNA of the strain selected in i) as the template, an about 1.6 kbp fragment of λattL-Km$^r$-λattR-Ptac sequence having the homologous sequence of the kdp operon upstream region at the 5' end and the 5' end homologous sequence containing the first start codon of the kdp operon at the 3' end was amplified.

The aforementioned PCR fragment was purified and introduced into SC17(0)/RSF-Red-TER by electroporation in a conventional manner.

The SC17(0)/RSF-Red-TER strain into which the PCR fragment was introduced was selected on L medium (10 g of Bacto tryptone, 5 g of yeast extract, 5 g of NaCl, and 15 g of agar in 1 L of purified water, pH 7.0) containing 40 mg/L of kanamycin to obtain about 20 colonies as transformants. Insertion of the aforementioned fragment in the kdp operon upstream region was confirmed by PCR using the two synthetic DNA primers shown in SEQ ID NOS: 53 and 54, and a strain in which insertion of the fragment was confirmed was designated SC17(0)::Ptac-kdp. Genomic DNA was extracted from this strain, and used to transform NA1/pSTV-yhfK strain by electroporation. The NA1/pSTV-yhfK strain was obtained from the AJ13601 strain (refer to Japanese Patent Laid-open No. 2001-333769) by eliminating the two plasmids RSFCPG and pSTVCB, and then introducing two plasmids, the plasmid for L-glutamic acid production, RSFPPG, and pSTV-yhfK (refer to Japanese Patent Laid-open No. 2005-278643).

Both of the plasmids RSFCPG and pSTVCB are disclosed in Japanese Patent Laid-open No. 2001-333769. RSFCPG contains the gltA, ppc and gdhA genes derived from *Escherichia coli*. pSTVCB is obtained by inserting the gltA gene derived from *Brevibacterium lactofermentum* into pSTV29 (Takara Shuzo). pSTV-yhfk is obtained by inserting the yhfk gene derived from *Pantoea ananatis* into pSTV29 (Takara Shuzo).

The NA1/pSTV-yhfK strain into which genomic DNA of SC17(0)::Ptac-kdp was introduced was selected on a plate of L medium (10 g of Bacto tryptone, 5 g of yeast extract, 5 g of NaCl and 15 g of agar in 1 L of purified water, pH 7.0) which was supplemented with minimal medium (0.5 g of glucose, 2 mM magnesium sulfate, 3 g of monopotassium phosphate, 0.5 g of sodium chloride, 1 g of ammonium chloride and 6 g of disodium phosphate in 1 L of purified water), 40 mg/L of kanamycin, 12.5 mg/L of tetracycline hydrochloride, and 25 mg/L of chloramphenicol. As a result, about 20 colonies were obtained as transformants. In all of these strains, the fragment of λattL-Km$^r$-λattR-Ptac was inserted upstream from the kdp operon, and one clone among them was selected and designated NA1::Ptac-kdp/pSTV-yhfK.

(3) Evaluation of the Culture of the kdp Operon Promoter-Substituted Strain in a Test Tube Then, in order to examine the effect of the enhancement of the kdp operon on growth, a culture was performed in test tubes. The NA1:Ptac-kdp/pSTV-yhfK strain and the NA1/pSTV-yhfK strain were used as controls, and the growth was examined under an acidic conditions.

Composition of medium for test tube culture:

| | |
|---|---|
| D-glucose | 0.5% |
| Na$_2$HPO$_4$ | 6.0 g/L |
| KH$_2$PO$_4$ | 3.0 g/L |
| NaCl | 0.5 g/L |
| NH$_4$Cl | 1.0 g/L |
| MgSO$_4$•7H$_2$O | 2.0 mM |
| ε-Diaminopimelic acid | 200 mg/L |
| L-Lysine hydrochloride | 200 mg/L |
| DL-Methionine | 200 mg/L |
| L-Glutamic acid | 30 g/L |
| Tetracycline hydrochloride | 12.5 mg/L |
| Chloramphenicol | 25 mg/L |

The medium was adjusted to pH 4.5 or pH 4.9 with aqueous ammonia, and then filtered.

Figure 4:
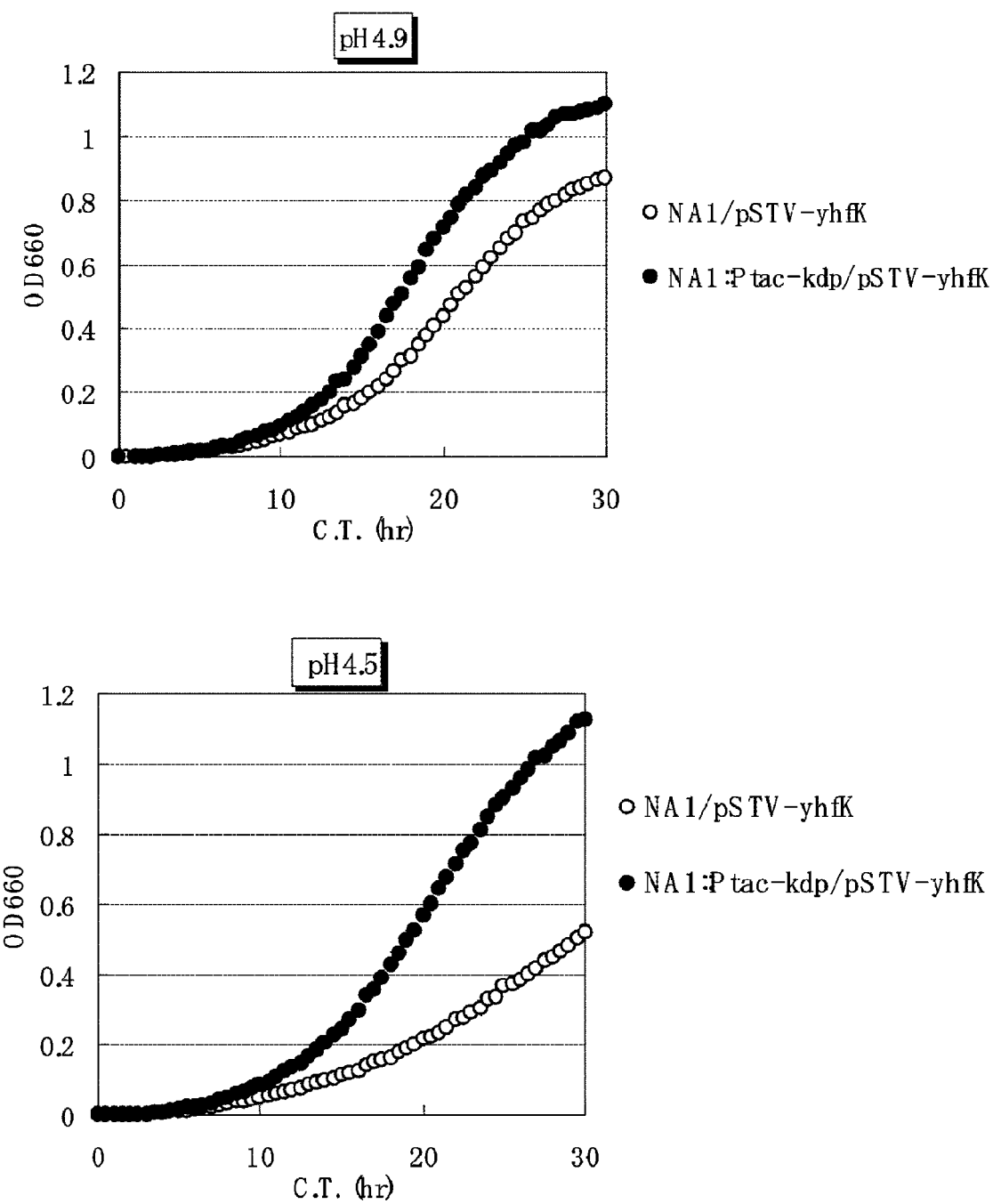
FIG. 4 is a graph which shows the growth of the kdp operon promoter-substituted strain in culture in a test tube under acidic conditions.

The NA1::Ptac-kdp/pSTV-yhfK and NA1/pSTV-yhfK strains were each pre-cultured in L medium (10 g of Bacto tryptone, 5 g of yeast extract, 5 g of NaCl, and 15 g of agar in 1 L of purified water, pH 7.0) which was supplemented with minimal medium (0.5 g of glucose, 2 mM magnesium sulfate, 3 g of monopotassium phosphate, 0.5 g of sodium chloride, 1 g of ammonium chloride and 6 g of disodium phosphate in 1 L of purified water), 12.5 mg/L of tetracycline hydrochloride and 25 mg/L of chloramphenicol, and cells corresponding to ⅛ of the plate were scraped, washed twice with physiological saline, and finally suspended in 1 ml of physiological saline. The suspension in a volume of 20 μL was inoculated into 5 mL of the medium for a test tube culture, and cultured at 34° C. with shaking. During the culture, OD (660 nm) was measured every 30 minutes using an automatic OD meter (TN1506 BIO PHOTORECORDER, ADVANTEC). The results are shown in FIG. 4.

As compared to the NA1/pSTV-yhfK control strain, the kdp-enhanced strain, NA1::Ptac-kdp/pSTV-yhfK, showed improvement of growth under acidic conditions of pH 4.5 or pH 4.9. Thus, the effect of the enhancement of the kdp operon to improve growth and L-glutamic acid production rate is demonstrated by these results.

(4) Evaluation of the Culture of the kdp Operon Promoter-Substituted Strain in a S-Jar Then, in order to examine the effect of the enhancement of the kdp operon on L-glutamic acid production, a L-glutamic acid production culture was performed by using the NA1:Ptac-kdp/pSTV-yhfK and the NA1/pSTV-yhfK strains.

The culture was performed in two steps: a seed culture to allow formation of cells, and a main culture to produce L-glutamic acid.

The seed culture was performed with the following medium composition.

Composition of seed culture medium:

| | |
|---|---|
| Sucrose | 50 g/L |
| MgSO$_4$•7H$_2$O | 0.4 g/L |
| GD113 (antifoam) | 0.1 mL/L |
| (NH$_4$)$_2$SO$_4$ | 4.0 g/L |
| KH$_2$PO$_4$ | 2.0 g/L |
| Yeast extract | 4.0 g/L |
| FeSO$_4$•7H$_2$O | 0.01 g/L |
| MnSO$_4$•5H$_2$O | 0.01 g/L |
| Citric acid | 0.02 g/L |
| L-Lysine hydrochloride | 0.4 g/L |
| DL-Methionine | 0.4 g/L |
| ε-Diaminopimelic acid | 0.4 g/L |
| Calcium pantothenate | 18 mg/L |
| Tetracycline hydrochloride | 12.5 mg/L |
| Chloramphenicol | 25 mg/L |

The medium was sterilized with steam at 120° C. for 20 minutes.

The NA1::Ptac-kdp/pSTV-yhfK and the NA1/pSTV-yhfK strains were each pre-cultured in L medium (10 g of Bacto tryptone, 5 g of yeast extract, 5 g of NaCl, and 15 g of agar in 1 L of purified water, pH 7.0) which was supplemented with minimal medium (0.5 g of glucose, 2 mM magnesium sulfate, 3 g of monopotassium phosphate, 0.5 g of sodium chloride, 1 g of ammonium chloride and 6 g of disodium phosphate in 1 L of purified water), 12.5 mg/L of tetracycline and 25 mg/L of chloramphenicol, and cells corresponding to one plate were inoculated into 300 mL of the medium of the aforementioned composition contained in a 1 L-volume mini jar, and stirring was controlled at 34° C. and pH 6.0 for about 12 hours so that aeration of 1/1 vvm and an oxygen concentration of 3% or higher is obtained. During the culture, pH was controlled to be 6.0 with the addition of ammonia gas. The seed culture was terminated at the time of depletion of the saccharide in the medium observed as an index.

Composition of the main culture medium is shown below.

Composition of culture medium: (Concentrations are after inoculation of 20% of seed culture medium)

| | |
|---|---|
| Sucrose | 100 g/L |
| MgSO$_4$•7H$_2$O | 0.4 g/L |
| GD113 | 0.1 mL/L |
| (NH$_4$)$_2$SO$_4$ | 5.0 g/L |
| KH$_2$PO$_4$ | 6.0 g/L |
| Yeast extract | 6.0 g/L |
| FeSO$_4$•7H$_2$O | 0.02 g/L |
| MnSO$_4$•5H$_2$O | 0.02 g/L |
| Citric acid | 0.02 g/L |
| Betaine* | 2.0 g/L |
| L-Lysine hydrochloride | 0.8 g/L |
| DL-Methionine | 0.6 g/L |
| ε-Diaminopimelic acid | 0.6 g/L |
| Calcium pantothenate | 18 mg/L |
| Tetracycline hydrochloride | 25 mg/L |
| Chloramphenicol | 25 mg/L |

*N,N,N-trimethylglycine

The cells obtained by the seed culture in a volume of 60 mL were inoculated into 240 mL of medium having the aforementioned composition contained in a 1 L-volume mini jar, and cultured at pH 4.7. The culture was terminated 16 hours after the start of the main culture. The cell density and L-glutamic acid concentration in the culture medium were measured over time. The cell density was examined by measuring turbidity of the culture medium diluted 101 times with water at 620 nm using a spectrophotometer (U-2000A, Hitachi). L-Glutamic acid concentration was measured for the culture supernatant appropriately diluted with water by using Biotech Analyzer (AS-210, Sakura SI).

Figure 5:
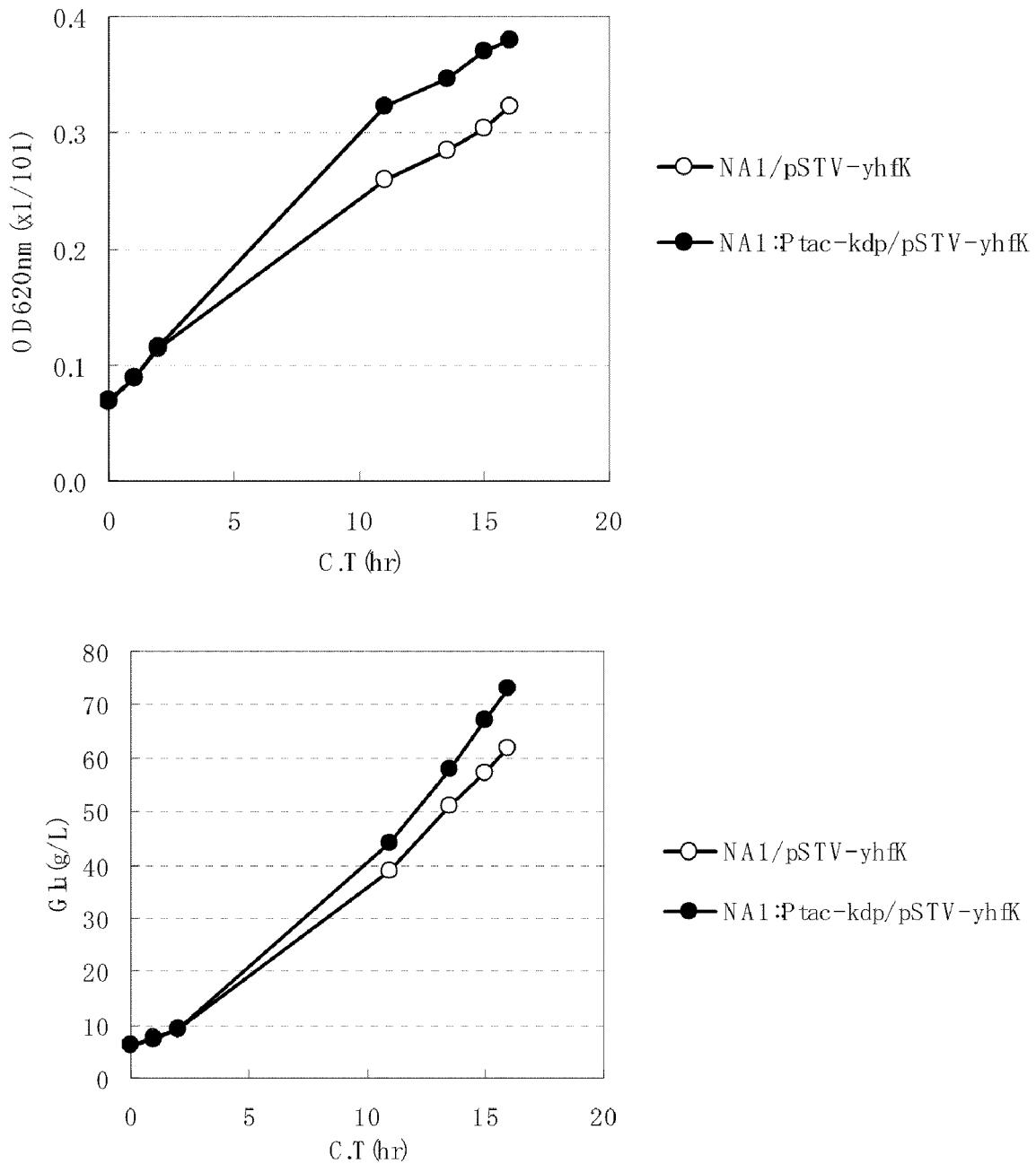
FIG. 5 is a graph which shows L-glutamic acid productivity of the kdp operon promoter-substituted strain.

The results are shown in Table 1 and FIG. 5. It became clear that growth as well as accumulation of L-glutamic acid and production rate of L-glutamic acid of the kdp operon-enhanced strain, NA1::Ptac-kdp/pSTV-yhfK strain, were improved as compared to the comparative strain, NA1/pSTV-yhfK strain.

TABLE 1

|  | NA1/pSTVyhfK | NA1::Ptac-kdp/pSTV-yhfK |
| --- | --- | --- |
| Produced L-glutamic acid (g/Jar) | 15.8 | 19.0 |
| L-Glutamic acid production rate (g/L/hr) | 3.30 | 3.96 |

Example 2

Amplification of the kdp Operon in L-Threonine-Producing *Escherichia coli*

(1) Construction of a Plasmid for Amplification of kdp Operon

In order to introduce the kdp operon into an *Escherichia* bacterium, a plasmid for amplification of the kdp operon is constructed by using the known plasmid pMW218 (Takara Shuzo).

pMW218 is first digested with the restriction enzymes HindIII and BamHI, and the reaction is terminated by adding a phenol/chloroform solution and mixing them. The reaction mixture is centrifuged, then the upper layer is collected, and DNAs are collected by ethanol precipitation. The kdp operon is separately amplified by PCR using a chromosome extracted from *Escherichia coli* MG1655 as the template and DNA primers shown in SEQ ID NOS: 55 and 56 (denaturation at 94° C. for 10 seconds, annealing at 60° C. for 30 seconds, and extension at 72° C. for 120 seconds). For PCR, Pyrobest DNA polymerase (Takara Shuzo) is used. The obtained kdp operon fragment is digested with the restriction enzymes HindIII and BamHI, and the reaction is terminated by adding a phenol/chloroform solution and mixing them.

The pMW218 digest and kdpABC gene region fragment prepared as described above are ligated by using DNA Ligation Kit Ver. 2 (Takara Shuzo). *Escherichia coli* (*E. coli* JM109 competent cells, Takara Shuzo) is transformed with the ligation solution, applied to LB agar medium containing 50 mg/L of kanamycin, and incubated overnight at 37° C. Colonies which appear on the agar medium are inoculated into the LB liquid medium containing 50 mg/L of kanamycin, and cultured at 37° C. for 8 hours with shaking. Plasmid DNA is extracted from each culture medium by the alkali-SDS method, and the structure thereof is confirmed by digestion with restriction enzymes to obtain pMW218kdp.

(2) Introduction of pMW218kdp into Threonine-Accumulating *Escherichia coli* B-3996 and Amino Acid Production pMW218kdp obtained as described above is introduced into the VKPM B-3996 strain by the electroporation method (Canadian Journal of Microbiology, 43, 197 (1997)).

The obtained transformant (B-3996/pMW218kdp) and the strain into which pMW218 is introduced as a control (B-3996/pMW218) are cultured as follows, and L-threonine concentrations in the culture supernatants are examined.

Each transformant is inoculated into 3 mL of the LB liquid medium containing 50 mg/L of kanamycin and 20 mg/L of streptomycin, and cultured overnight at 37° C. in a test tube, then 200 μL of the culture medium is inoculated into a threonine production medium (20 ml) containing 50 mg/L of kanamycin and 20 mg/L of streptomycin, and the culture is performed at 37° C. for 24 hours with shaking. After completion of the culture, the cells are removed by centrifugation, and L-threonine concentration in the culture supernatant is measured by using an amino acid analyzer (L-8500, Hitachi). It can be seen that the amount of L-threonine which is produced in the medium is increased in the kdp operon-amplified strain, B-3996/pMW218kdp, as compared to the control B-3996/pMW218 strain.

Threonine production medium:

| D-glucose | 40 g/L |
| --- | --- |
| $(NH_4)_2SO_4$ | 16 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| L-Isoleucine | 50 mg/L |
| DL-Methionine | 500 mg/L |
| Calcium carbonate | 0.6 g/L |
| Streptomycin | 20 mg/L |
| Kanamycin | 50 mg/L |

The medium is adjusted to pH 7.5 with potassium hydroxide.

The medium is sterilized with steam at 115° C. for 10 minutes.

Explanation of Sequence Listing

SEQ ID NO: 1: Nucleotide sequence of kdp operon of *Escherichia coli* (amino acid sequences of kdpA, kdpB and kdpC are also shown)
kdpF: 457 to 546
kdpA: 546 to 2219
kdpB: 2242 to 4290
kdpC: 4299 to 4871
kdpD: 4864 to 7548
kdpE: 7545 to 8222
SEQ ID NO: 2: Amino acid sequence of KdpA
SEQ ID NO: 3: Amino acid sequence of KdpB
SEQ ID NO: 4: Amino acid sequence of KdpC
SEQ ID NO: 5: Amino acid sequence of KdpD
SEQ ID NO: 6: Amino acid sequence of KdpE
SEQ ID NO: 5: Nucleotide sequence of KdpD operon (amino acid sequence of SDHC is also shown)
SEQ ID NO: 7: Nucleotide sequence of *Pantoea ananatis* kdp operon (amino acid sequences of kdpA, kdpB, kdpC and kdpD are also shown)
kdpA: 543 to 2225
kdpB: 2228 to 4273
kdpC: 4284 to 4853
kdpD: 4867 to 7542
SEQ ID NO: 8: Amino acid sequence of KdpA
SEQ ID NO: 9: Amino acid sequence of KdpB
SEQ ID NO: 10: Amino acid sequence of KdpC
SEQ ID NO: 11: Amino acid sequence of KdpD
SEQ ID NO: 12: Nucleotide sequence of *Pantoea ananatis* kdpE gene
SEQ ID NO: 13: Amino acid sequence of KdpE
SEQ ID NO: 14: Nucleotide sequence of hisD gene of *Pantoea ananatis*

SEQ ID NO: 15: Primer for amplification of fragment for integration of Km$^r$ gene into hisD gene
SEQ ID NO: 16: Primer for amplification of fragment for integration of Km$^r$ gene into hisD gene
SEQ ID NO: 17: Primer for cat gene amplification
SEQ ID NO: 18: Primer for cat gene amplification
SEQ ID NO: 19: Primer for sacB gene amplification
SEQ ID NO: 20: Primer for sacB gene amplification
SEQ ID NO: 21: Primer for amplification of DNA fragment containing PlacUV5 promoter
SEQ ID NO: 22: Primer for amplification of DNA fragment containing PlacUV5 promoter
SEQ ID NO: 23: Primer for amplification of DNA fragment containing λRedαβγ genes and tL3
SEQ ID NO: 24: Primer for amplification of DNA fragment containing λRedαβγ genes and tL3
SEQ ID NO: 25: Primer for amplification of DNA fragment containing PlacUV5 promoter and TrrnB
SEQ ID NO: 26: Primer for amplification of DNA fragment containing PlacUV5 promoter and TrrnB
SEQ ID NO: 27: Primer for attL amplification
SEQ ID NO: 28: Primer for attL amplification
SEQ ID NO: 29: Nucleotide sequence of attL
SEQ ID NO: 30: Primer for attR amplification
SEQ ID NO: 31: Primer for attR amplification
SEQ ID NO: 32: Nucleotide sequence of attR
SEQ ID NO: 33: Primer for amplification of DNA fragment containing bla gene
SEQ ID NO: 34: Primer for amplification of DNA fragment containing bla gene
SEQ ID NO: 35: Primer for amplification of DNA fragment containing ter_rrnB
SEQ ID NO: 36: Primer for amplification of DNA fragment containing ter_rrnB
SEQ ID NO: 37: Nucleotide sequence of DNA fragment containing ter_thrL terminator
SEQ ID NO: 38: Primer for amplification of DNA fragment containing ter_thrL terminator
SEQ ID NO: 39: Primer for amplification of DNA fragment containing ter_thrL terminator
SEQ ID NO: 40: Primer for amplifying part of gltA gene other than ORF
SEQ ID NO: 41: Primer for amplifying part of gltA gene other than ORF
SEQ ID NO: 42: Primer for prpC gene amplification
SEQ ID NO: 43: Primer for prpC gene amplification
SEQ ID NO: 44: Nucleotide sequence of yghU gene of *Pantoea ananatis*
SEQ ID NO: 45: Nucleotide sequence of scrK gene of *Pantoea ananatis*
SEQ ID NO: 46: Nucleotide sequence of lacZ gene of *Pantoea ananatis*
SEQ ID NO: 47: Primer for amplification of DNA fragment containing Ptac promoter
SEQ ID NO: 48: Primer for amplification of DNA fragment containing Ptac promoter
SEQ ID NO: 49: Primer for amplification of DNA fragment containing Km resistance gene
SEQ ID NO: 50: Primer for amplification of DNA fragment containing Km resistance gene
SEQ ID NO: 51: Primer for amplification of kdp operon upstream sequence ligated to tac promoter
SEQ ID NO: 52: Primer for amplification of kdp operon upstream sequence ligated to tac promoter
SEQ ID NO: 53: Primer for confirming kdp operon upstream structure
SEQ ID NO: 54: Primer for confirming kdp operon upstream structure
SEQ ID NO: 55: Primer for kdp operon amplification
SEQ ID NO: 56: Primer for kdp operon amplification
SEQ ID NO: 57: Consensus sequence of KdpA amino acid sequences of *Pantoea ananatis* and *Escherichia coli*
SEQ ID NO: 58: Consensus sequence of KdpB amino acid sequences of *Pantoea ananatis* and *Escherichia coli*
SEQ ID NO: 59: Consensus sequence of KdpC amino acid sequences of *Pantoea ananatis* and *Escherichia coli*

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

INDUSTRIAL APPLICABILITY

By using the microorganism of the present invention, an L-amino acid such as L-glutamic acid, L-lysine, L-threonine, L-arginine, L-histidine, L-isoleucine, L-valine, L-leucine, L-threonine, L-phenylalanine, L-tyrosine, L-tryptophan or L-cysteine, or the like can be efficiently produced by fermentation. In one embodiment, the microorganism of the present invention shows both superior L-amino acid production and production rate.

What is claimed is:

1. A method for producing an L-amino acid comprising:
   A) culturing a an *Escherichia* or a *Pantoea* bacterium in a medium to produce and accumulate an L-amino acid in the medium or the bacterium, and
   B) collecting the L-amino acid from the medium or bacterium,
   wherein the bacterium is able to produce the L-amino acid and has been modified so that the kdp system encoded by the kdp operon is enhanced, and
   wherein the kdp operon comprises the kdpA, kdpB, and kdpC genes, and
   wherein the kdpA gene encodes a protein comprising the amino acid sequence shown in SEQ ID NO: 8, the kdpB gene encodes a protein comprising the amino acid sequence shown in SEQ ID NO: 9, and the kdpC gene encodes a protein having the amino acid sequence shown in SEQ ID NO: 10, and
   wherein each of the protein can comprise substitutions, deletions, insertions or additions of one to five amino acids.

2. The method according to claim 1, wherein the L-amino acid is selected from the group consisting of L-glutamic acid, L-lysine, L-threonine, L-arginine, L-histidine, L-isoleucine, L-valine, L-leucine, L-phenylalanine, L-tyrosine, L-tryptophan, L-cysteine, and combinations thereof.

3. The method according to claim 1, wherein the kdp system is enhanced by a method selected from the group consisting of:
   a) increasing expression of the kdp operon,
   b) increasing expression of one or more gene on the kdp operon,
   c) increasing translation of the kdp operon,
   d) increasing translation of one or more genes on the kdp operon, and
   e) combinations thereof.

4. The method according to claim 3, wherein the kdp system is enhanced by a method selected from the group consisting of:
   a) increasing the copy number of the kdp operon,
   b) increasing the copy number of one or more genes on the kdp operon, and
   c) modifying an expression control sequence of the operon.

5. The method according to claim 1, wherein the bacterium is *Escherichia coli* or *Pantoea ananatis*.

* * * * *

UNITED STATES PATENT AND TRADEMARK OFFICE
CERTIFICATE OF CORRECTION

PATENT NO. : 7,919,284 B2  
APPLICATION NO. : 12/497918  
DATED : April 5, 2011  
INVENTOR(S) : Rie Takikawa et al.

It is certified that error appears in the above-identified patent and that said Letters Patent is hereby corrected as shown below:

Col. 119, lines 38-58 should read,

1. A method for producing an L-amino acid comprising:
A) culturing an Escherichia or a Pantoea bacterium in a medium to produce and accumulate an L-amino acid in the medium or the bacterium, and
B) collecting the L-amino acid from the medium or bacterium,
wherein the bacterium is able to produce the L-amino acid and has been modified so that the kdp system encoded by the kdp operon is enhanced, and
wherein the kdp operon comprises the kdpA, kdpB, and kdpC genes, and
wherein the kdpA gene encodes a protein comprising the amino acid sequence shown in SEQ ID NO: 8, the kdpB gene encodes a protein comprising the amino acid sequence shown in SEQ ID NO: 9, and the kdpC gene encodes a protein having the amino acid sequence shown in SEQ ID NO: 10, and
wherein each of the protein can comprise substitutions, deletions, insertions or additions of one to five amino acids.

Signed and Sealed this
Eighth Day of November, 2011

David J. Kappos
*Director of the United States Patent and Trademark Office*

SEQUENCE LISTING

```
<160> NUMBER OF SEQ ID NOS: 59

<210> SEQ ID NO 1
<211> LENGTH: 8501
<212> TYPE: DNA
<213> ORGANISM: Escherichia coli
<220> FEATURE:
<221> NAME/KEY: CDS
<222> LOCATION: (546)..(2219)
<220> FEATURE:
<221> NAME/KEY: CDS
<222> LOCATION: (2242)..(4290)
<220> FEATURE:
<221> NAME/KEY: CDS
<222> LOCATION: (4299)..(4871)

<400> SEQUENCE: 1
```

```
cgaccagacg cgatgcaggt agctgtaaaa gcgggcgcgg tctttccaga aaagcatgaa    60
aggcagcgcc agaacgcccg ctgcaaccgc ataagtacgg cgtaaaaaga taagccatgc   120
aggatattct ctgtagagtt ccatactttt ctccccattt tgtatctacc cggtgaatgg   180
caccggaaaa atgaatttgt ttatctgatg aaaatagtac cgccttttgt gtaattttac   240
tactcatccg accacttatt tttgcttatt gatggtttat ttacattcat cctgtaatta   300
agttacacaa aagttaaatt aatactaaac attagttaaa tcatggcttt tgccattttt   360
atactttttt tacaccccgc ccgcagattt ttgcgaaatc tttgcagcca gaattctacc   420
cttccggtat cacttttagg ccactggagg tgcactgtga gtgcaggcgt gataaccggc   480
gtattgctgg tgtttttatt actgggttat ctggtttatg ccctgatcaa tgcggaggcg   540 ttctg atg gct gcg caa ggg ttc tta ctg atc gcc acg ttt tta ctg gtg    590
      Met Ala Ala Gln Gly Phe Leu Leu Ile Ala Thr Phe Leu Leu Val
        1               5                  10                  15 tta atg gtg ctg gcg cgt cct tta ggc agc ggg ctg gcg cgg ctg att       638
Leu Met Val Leu Ala Arg Pro Leu Gly Ser Gly Leu Ala Arg Leu Ile
            20                  25                  30 aat gac att cct ctt ccc ggt aca acg ggc gtt gag cgc gta ctt ttt       686
Asn Asp Ile Pro Leu Pro Gly Thr Thr Gly Val Glu Arg Val Leu Phe
        35                  40                  45 cgc gca ctt ggc gtc tct gac cgt gag atg aac tgg aag caa tat ctt       734
Arg Ala Leu Gly Val Ser Asp Arg Glu Met Asn Trp Lys Gln Tyr Leu
    50                  55                  60 tgt gcc att ctc ggc ctg aac atg ctg ggg ctg gcg gtg ctg ttt ttt       782
Cys Ala Ile Leu Gly Leu Asn Met Leu Gly Leu Ala Val Leu Phe Phe
65                  70                  75 atg ttg ctc ggt cag cac tat ctg ccg ctt aat cca cag cag ttg cca       830
Met Leu Leu Gly Gln His Tyr Leu Pro Leu Asn Pro Gln Gln Leu Pro
80                  85                  90                  95 ggg ctg tcg tgg gat ctg gcg ctg aat acc gcc gtc agc ttt gtc acc       878
Gly Leu Ser Trp Asp Leu Ala Leu Asn Thr Ala Val Ser Phe Val Thr
                100                 105                 110 aat acc aac tgg caa tct tat agc ggt gaa acc acg ttg agc tat ttc       926
Asn Thr Asn Trp Gln Ser Tyr Ser Gly Glu Thr Thr Leu Ser Tyr Phe
            115                 120                 125 agc cag atg gcg ggc tta acg gtg caa aac ttt ctt tct gcc gcc agc       974
Ser Gln Met Ala Gly Leu Thr Val Gln Asn Phe Leu Ser Ala Ala Ser
        130                 135                 140 ggg att gcg gtg att ttt gcc ctc atc cgt gcg ttt acc cgc cag agc      1022
Gly Ile Ala Val Ile Phe Ala Leu Ile Arg Ala Phe Thr Arg Gln Ser
    145                 150                 155 atg agc acg ctc ggg aat gcc tgg gtc gat ctg cta cgc atc acg tta      1070
Met Ser Thr Leu Gly Asn Ala Trp Val Asp Leu Leu Arg Ile Thr Leu
160                 165                 170                 175 tgg gtg cta gtc cct gtg gcg ttg ttg att gca ctg ttt ttt att caa      1118
Trp Val Leu Val Pro Val Ala Leu Leu Ile Ala Leu Phe Phe Ile Gln
                180                 185                 190 caa ggt gcg ctg caa aac ttt ctg cct tat cag gct gtg aat acc gtt      1166
Gln Gly Ala Leu Gln Asn Phe Leu Pro Tyr Gln Ala Val Asn Thr Val
            195                 200                 205 gaa gga gcg caa cag ctg tta ccc atg ggg cct gta gct tct cag gaa      1214
Glu Gly Ala Gln Gln Leu Leu Pro Met Gly Pro Val Ala Ser Gln Glu
        210                 215                 220 gcg atc aag atg ctc ggt act aac ggc ggt ggc ttc ttt aat gcc aac      1262
Ala Ile Lys Met Leu Gly Thr Asn Gly Gly Gly Phe Phe Asn Ala Asn
    225                 230                 235 tcg tcg cat ccg ttt gaa aac cca acc gca ctg acc aac ttc gtg cag      1310
Ser Ser His Pro Phe Glu Asn Pro Thr Ala Leu Thr Asn Phe Val Gln
```

```
                240                 245                 250                 255
atg ctg gcg atc ttc ttg atc cca acg gcg ctg tgc ttt gcc ttt ggt    1358
Met Leu Ala Ile Phe Leu Ile Pro Thr Ala Leu Cys Phe Ala Phe Gly
            260                 265                 270 gaa gtg atg ggc gat cgc cgc cag ggg cgc atg ttg ctg tgg gcg atg    1406
Glu Val Met Gly Asp Arg Arg Gln Gly Arg Met Leu Leu Trp Ala Met
        275                 280                 285 tca gtg att ttt gtc atc tgc gta ggc gtg gtg atg tgg gca gaa gtt    1454
Ser Val Ile Phe Val Ile Cys Val Gly Val Val Met Trp Ala Glu Val
    290                 295                 300 cag ggt aat cct cat ctg ctg gca ctg gcg acg gac agc agc atc aat    1502
Gln Gly Asn Pro His Leu Leu Ala Leu Gly Thr Asp Ser Ser Ile Asn
305                 310                 315 atg gaa ggt aaa gag agc cgt ttc ggc gtg ctg gtc agt agc ctg ttt    1550
Met Glu Gly Lys Glu Ser Arg Phe Gly Val Leu Val Ser Ser Leu Phe
320                 325                 330                 335 gcg gtc gtg acg acg gcg gct tcc tgt ggc gcg gtg att gcg atg cat    1598
Ala Val Val Thr Thr Ala Ala Ser Cys Gly Ala Val Ile Ala Met His
                340                 345                 350 gat tcg ttt acc gct ctc ggt ggc atg gtg ccg atg tgg ctg atg caa    1646
Asp Ser Phe Thr Ala Leu Gly Gly Met Val Pro Met Trp Leu Met Gln
            355                 360                 365 att ggt gaa gtg gtg ttc ggc ggt gtc ggt tct ggt ctt tac ggc atg    1694
Ile Gly Glu Val Val Phe Gly Gly Val Gly Ser Gly Leu Tyr Gly Met
        370                 375                 380 atg ctg ttt gtc ctg ctg gcg gtg ttt att gcc ggg ctg atg att ggt    1742
Met Leu Phe Val Leu Leu Ala Val Phe Ile Ala Gly Leu Met Ile Gly
    385                 390                 395 cgt aca ccg gaa tat ctg ggt aaa aaa atc gac gta cgc gag atg aaa    1790
Arg Thr Pro Glu Tyr Leu Gly Lys Lys Ile Asp Val Arg Glu Met Lys
400                 405                 410                 415 ctg act gca ctg gca att ctg gtt acc ccg acg ctg gtg ctg atg ggc    1838
Leu Thr Ala Leu Ala Ile Leu Val Thr Pro Thr Leu Val Leu Met Gly
                420                 425                 430 gcg gcg ttg gcg atg atg acc gac gcc gga cgt agc gcc atg ctc aac    1886
Ala Ala Leu Ala Met Met Thr Asp Ala Gly Arg Ser Ala Met Leu Asn
            435                 440                 445 cct ggc ccg cat ggt ttt agc gaa gtg ctg tac gcc gtg tca tcc gcc    1934
Pro Gly Pro His Gly Phe Ser Glu Val Leu Tyr Ala Val Ser Ser Ala
        450                 455                 460 gct aac aac aac ggc agc gcc ttt gcc gga tta agc gcc aac tct ccg    1982
Ala Asn Asn Asn Gly Ser Ala Phe Ala Gly Leu Ser Ala Asn Ser Pro
    465                 470                 475 ttc tgg aac tgt tta ctg gcg ttc tgc atg ttt gtc ggt cgc ttc ggg    2030
Phe Trp Asn Cys Leu Leu Ala Phe Cys Met Phe Val Gly Arg Phe Gly
480                 485                 490                 495 gtg att atc ccg gtg atg gca att gcc ggt tcg ctg gtg agt aaa aag    2078
Val Ile Ile Pro Val Met Ala Ile Ala Gly Ser Leu Val Ser Lys Lys
                500                 505                 510 agc caa gcc gcc agc tcc ggc acg ctg cca acg cac ggc ccg ctg ttt    2126
Ser Gln Ala Ala Ser Ser Gly Thr Leu Pro Thr His Gly Pro Leu Phe
            515                 520                 525 gtt ggc ctg tta atc ggc acc gtg ttg ctg gtt ggc gca ctg acc ttt    2174
Val Gly Leu Leu Ile Gly Thr Val Leu Leu Val Gly Ala Leu Thr Phe
        530                 535                 540 atc cct gcc ctg gcg ctt ggt ccg gtg gcg gaa tat ctc tcc tga        2219
Ile Pro Ala Leu Ala Leu Gly Pro Val Ala Glu Tyr Leu Ser
    545                 550                 555 tgatattgag tgagcactga at atg agt cgt aaa caa ctg gcg cta ttc gaa   2271
                          Met Ser Arg Lys Gln Leu Ala Leu Phe Glu
```

| | | | | | | | | | | | | | | | | |
|---|---|---|---|---|---|---|---|---|---|---|---|---|---|---|---|---|
| cca | aca | ctt | gtc | gtt | cag | gcg | ctg | aaa | gaa | gcg | gtg | aaa | aaa | tta | aac | 2319 |
| Pro | Thr | Leu | Val | Val | Gln | Ala | Leu | Lys | Glu | Ala | Val | Lys | Lys | Leu | Asn | |
| | 570 | | | | | 575 | | | | | 580 | | | | | |
| ccg | cag | gcg | caa | tgg | cgc | aat | ccg | gtg | atg | ttt | atc | gtc | tgg | atc | ggc | 2367 |
| Pro | Gln | Ala | Gln | Trp | Arg | Asn | Pro | Val | Met | Phe | Ile | Val | Trp | Ile | Gly | |
| 585 | | | | | 590 | | | | | 595 | | | | | | |
| agt | ctg | ctg | acc | acc | tgt | att | agc | atc | gcg | atg | gca | agc | ggt | gcg | atg | 2415 |
| Ser | Leu | Leu | Thr | Thr | Cys | Ile | Ser | Ile | Ala | Met | Ala | Ser | Gly | Ala | Met | |
| 600 | | | | 605 | | | | | 610 | | | | | 615 | | |
| ccc | ggc | aat | gcg | ctg | ttt | agc | gcg | gcc | att | agc | ggt | tgg | ctg | tgg | atc | 2463 |
| Pro | Gly | Asn | Ala | Leu | Phe | Ser | Ala | Ala | Ile | Ser | Gly | Trp | Leu | Trp | Ile | |
| | | | | 620 | | | | | 625 | | | | | 630 | | |
| acc | gta | ctg | ttc | gct | aat | ttc | gcc | gag | gcg | ctg | gca | gaa | ggc | cgc | agt | 2511 |
| Thr | Val | Leu | Phe | Ala | Asn | Phe | Ala | Glu | Ala | Leu | Ala | Glu | Gly | Arg | Ser | |
| | | | 635 | | | | | 640 | | | | | 645 | | | |
| aaa | gcg | cag | gcc | aac | agt | ctg | aaa | ggg | gtg | aaa | aaa | act | gcc | ttt | gcc | 2559 |
| Lys | Ala | Gln | Ala | Asn | Ser | Leu | Lys | Gly | Val | Lys | Lys | Thr | Ala | Phe | Ala | |
| | | 650 | | | | | 655 | | | | | 660 | | | | |
| cgc | aag | ctg | cgt | gag | ccg | aaa | tat | ggc | gct | gcg | gcg | gac | aaa | gtt | cct | 2607 |
| Arg | Lys | Leu | Arg | Glu | Pro | Lys | Tyr | Gly | Ala | Ala | Ala | Asp | Lys | Val | Pro | |
| 665 | | | | | 670 | | | | | 675 | | | | | | |
| gcc | gac | caa | ctt | cgt | aaa | ggc | gat | atc | gta | ctg | gta | gaa | gct | ggc | gat | 2655 |
| Ala | Asp | Gln | Leu | Arg | Lys | Gly | Asp | Ile | Val | Leu | Val | Glu | Ala | Gly | Asp | |
| 680 | | | | 685 | | | | | 690 | | | | | 695 | | |
| att | atc | ccc | tgc | gat | ggt | gaa | gtt | att | gaa | ggg | ggt | gca | tcg | gtc | gat | 2703 |
| Ile | Ile | Pro | Cys | Asp | Gly | Glu | Val | Ile | Glu | Gly | Gly | Ala | Ser | Val | Asp | |
| | | | | 700 | | | | | 705 | | | | | 710 | | |
| gaa | agc | gcc | atc | acc | ggg | gaa | tcg | gca | ccg | gtg | atc | cgt | gaa | tcc | ggc | 2751 |
| Glu | Ser | Ala | Ile | Thr | Gly | Glu | Ser | Ala | Pro | Val | Ile | Arg | Glu | Ser | Gly | |
| | | | 715 | | | | | 720 | | | | | 725 | | | |
| ggc | gat | ttt | gcc | tcc | gtc | acc | ggc | ggc | acg | cgt | att | ctt | tct | gac | tgg | 2799 |
| Gly | Asp | Phe | Ala | Ser | Val | Thr | Gly | Gly | Thr | Arg | Ile | Leu | Ser | Asp | Trp | |
| | | 730 | | | | | 735 | | | | | 740 | | | | |
| ctg | gtg | att | gag | tgt | agc | gtt | aac | ccc | ggc | gag | aca | ttt | ctg | gat | cgg | 2847 |
| Leu | Val | Ile | Glu | Cys | Ser | Val | Asn | Pro | Gly | Glu | Thr | Phe | Leu | Asp | Arg | |
| | 745 | | | | | 750 | | | | | 755 | | | | | |
| atg | atc | gcg | atg | gtg | gaa | ggc | gca | cag | cga | cgc | aaa | acg | ccg | aac | gaa | 2895 |
| Met | Ile | Ala | Met | Val | Glu | Gly | Ala | Gln | Arg | Arg | Lys | Thr | Pro | Asn | Glu | |
| 760 | | | | 765 | | | | | 770 | | | | | 775 | | |
| att | gcc | ctg | acc | att | ctg | ctg | att | gcc | ctg | act | atc | gtc | ttt | tta | ctg | 2943 |
| Ile | Ala | Leu | Thr | Ile | Leu | Leu | Ile | Ala | Leu | Thr | Ile | Val | Phe | Leu | Leu | |
| | | | 780 | | | | | 785 | | | | | 790 | | | |
| gca | acc | gcc | acg | ctg | tgg | ccg | ttt | tcc | gcg | tgg | ggc | ggt | aat | gca | gtc | 2991 |
| Ala | Thr | Ala | Thr | Leu | Trp | Pro | Phe | Ser | Ala | Trp | Gly | Gly | Asn | Ala | Val | |
| | | | 795 | | | | | 800 | | | | | 805 | | | |
| agc | gta | acg | gta | ctg | gtg | gcg | ctg | ctg | gtc | tgt | ctg | atc | cca | acc | act | 3039 |
| Ser | Val | Thr | Val | Leu | Val | Ala | Leu | Leu | Val | Cys | Leu | Ile | Pro | Thr | Thr | |
| | | 810 | | | | | 815 | | | | | 820 | | | | |
| att | ggc | ggc | ctg | ttg | tca | gcg | atc | ggc | gtc | gcc | ggg | atg | agc | cgg | atg | 3087 |
| Ile | Gly | Gly | Leu | Leu | Ser | Ala | Ile | Gly | Val | Ala | Gly | Met | Ser | Arg | Met | |
| | 825 | | | | | 830 | | | | | 835 | | | | | |
| cta | ggc | gcg | aat | gtg | att | gcc | acc | agc | gga | cgt | gca | gtt | gaa | gcg | gca | 3135 |
| Leu | Gly | Ala | Asn | Val | Ile | Ala | Thr | Ser | Gly | Arg | Ala | Val | Glu | Ala | Ala | |
| 840 | | | | 845 | | | | | 850 | | | | | 855 | | |
| ggt | gac | gtt | gac | gtt | ctg | cta | ctg | gat | aaa | acc | ggc | acc | atc | aca | ctc | 3183 |
| Gly | Asp | Val | Asp | Val | Leu | Leu | Leu | Asp | Lys | Thr | Gly | Thr | Ile | Thr | Leu | |
| | | | 860 | | | | | 865 | | | | | 870 | | | |
| ggt | aac | cgt | cag | gcg | tcg | gag | ttt | atc | ccc | gcg | cag | ggc | gtg | gat | gaa | 3231 |
| Gly | Asn | Arg | Gln | Ala | Ser | Glu | Phe | Ile | Pro | Ala | Gln | Gly | Val | Asp | Glu | |

-continued

```
              875                 880                 885
aaa acg ctg gct gac gcc gca caa ctg gct tcg ctg gct gat gaa acg    3279
Lys Thr Leu Ala Asp Ala Ala Gln Leu Ala Ser Leu Ala Asp Glu Thr
        890                 895                 900 ccg gaa ggc cgc agt att gtg atc ctc gcc aag cag cgt ttt aac ctg    3327
Pro Glu Gly Arg Ser Ile Val Ile Leu Ala Lys Gln Arg Phe Asn Leu
    905                 910                 915 cgc gag cgc gat gtg cag tcg ctc cat gcc acc ttt gta ccg ttt act    3375
Arg Glu Arg Asp Val Gln Ser Leu His Ala Thr Phe Val Pro Phe Thr
920                 925                 930                 935 gcg caa agc cgg atg agc ggg atc aac atc gac aac cgc atg atc cgt    3423
Ala Gln Ser Arg Met Ser Gly Ile Asn Ile Asp Asn Arg Met Ile Arg
            940                 945                 950 aaa ggt tct gtc gat gcc att cgt cgc cat gtt gag gct aac ggt ggt    3471
Lys Gly Ser Val Asp Ala Ile Arg Arg His Val Glu Ala Asn Gly Gly
        955                 960                 965 cac ttc cct acc gat gtt gat caa aaa gtc gat cag gtt gcg cgt cag    3519
His Phe Pro Thr Asp Val Asp Gln Lys Val Asp Gln Val Ala Arg Gln
    970                 975                 980 gga gcc acg ccg ctg gtg gtg gtg gaa ggt tct cgt gtg ctg ggc gtt    3567
Gly Ala Thr Pro Leu Val Val Val Glu Gly Ser Arg Val Leu Gly Val
985                 990                 995 att gcg ctg aaa gat atc gtc aaa ggc ggt att aaa gag cgc ttc        3612
Ile Ala Leu Lys Asp Ile Val Lys Gly Gly Ile Lys Glu Arg Phe
    1000                1005                1010 gcc cag ctg cgc aaa atg ggc att aaa acg gtg atg att acc ggc        3657
Ala Gln Leu Arg Lys Met Gly Ile Lys Thr Val Met Ile Thr Gly
1015                1020                1025 gat aac cgt ctg act gcc gcc gcg att gct gcg gaa gcg ggt gtc        3702
Asp Asn Arg Leu Thr Ala Ala Ala Ile Ala Ala Glu Ala Gly Val
1030                1035                1040 gat gat ttt ctc gcc gaa gcg aca ccg gag gcc aag ctg gca ttg        3747
Asp Asp Phe Leu Ala Glu Ala Thr Pro Glu Ala Lys Leu Ala Leu
1045                1050                1055 atc cgt cag tat cag gcg gaa ggt cgt ttg gta gcg atg acc ggc        3792
Ile Arg Gln Tyr Gln Ala Glu Gly Arg Leu Val Ala Met Thr Gly
1060                1065                1070 gac ggc acc aac gat gct ccg gcg ctg gcg cag gca gat gtc gcg        3837
Asp Gly Thr Asn Asp Ala Pro Ala Leu Ala Gln Ala Asp Val Ala
1075                1080                1085 gtg gcg atg aac tcc ggc acc cag gcg gcg aaa gag gcg ggc aat        3882
Val Ala Met Asn Ser Gly Thr Gln Ala Ala Lys Glu Ala Gly Asn
1090                1095                1100 atg gtc gat ctc gac tct aac ccg acc aag ttg atc gag gtg gtg        3927
Met Val Asp Leu Asp Ser Asn Pro Thr Lys Leu Ile Glu Val Val
1105                1110                1115 cac att ggc aaa cag atg ctg atg acc cgt ggc tcg ctg acc acc        3972
His Ile Gly Lys Gln Met Leu Met Thr Arg Gly Ser Leu Thr Thr
1120                1125                1130 ttc agc att gcc aac gat gtg gcg aaa tac ttc gcc att att ccg        4017
Phe Ser Ile Ala Asn Asp Val Ala Lys Tyr Phe Ala Ile Ile Pro
1135                1140                1145 gcg gca ttc gcg gca acg tat ccg cag tta aat gcg ctg aac atc        4062
Ala Ala Phe Ala Ala Thr Tyr Pro Gln Leu Asn Ala Leu Asn Ile
1150                1155                1160 atg tgc ctg cat tcg ccc gac tcc gca atc ctc agt gcg gtg att        4107
Met Cys Leu His Ser Pro Asp Ser Ala Ile Leu Ser Ala Val Ile
1165                1170                1175 ttc aac gcc ttg att atc gtc ttt ttg att ccc ctg gcg tta aaa        4152
Phe Asn Ala Leu Ile Ile Val Phe Leu Ile Pro Leu Ala Leu Lys
```

```
                                                                1180                    1185                    1190
ggc gtg agt tat aaa ccg ctt acc gct tct gcc atg ttg cgc cgt                                                             4197
Gly Val Ser Tyr Lys Pro Leu Thr Ala Ser Ala Met Leu Arg Arg
1195                1200                1205 aac tta tgg att tac ggt ctg ggt ggg ctg ctg gtg ccg ttt atc                                                             4242
Asn Leu Trp Ile Tyr Gly Leu Gly Gly Leu Leu Val Pro Phe Ile
1210                1215                1220 ggt atc aaa gtc att gat tta ctg ctg acc gtt tgc ggt ctg gtg                                                             4287
Gly Ile Lys Val Ile Asp Leu Leu Leu Thr Val Cys Gly Leu Val
1225                1230                1235 tga ggtttacc atg  agt gga tta cgt ccg gca tta tca aca ttt  atc                                                          4334
            Met  Ser Gly Leu Arg Pro Ala Leu Ser Thr Phe  Ile
                 1240                1245                1250 ttt ctg tta ttg att act ggc ggc gtt tac ccg ctg ctg acc acc                                                             4379
Phe Leu Leu Leu Ile Thr Gly Gly Val Tyr Pro Leu Leu Thr Thr
                1255                1260                1265 gta ctg ggg caa tgg tgg ttt ccc tgg cag gcc aat ggt tcg ttg                                                             4424
Val Leu Gly Gln Trp Trp Phe Pro Trp Gln Ala Asn Gly Ser Leu
            1270                1275                1280 att cgt gaa ggt gat acg gtg cgc ggt tcg gca tta atc ggg cag                                                             4469
Ile Arg Glu Gly Asp Thr Val Arg Gly Ser Ala Leu Ile Gly Gln
        1285                1290                1295 aat ttt acc ggc aac ggc tat ttt cat ggt cgc ccg tcg gca acg                                                             4514
Asn Phe Thr Gly Asn Gly Tyr Phe His Gly Arg Pro Ser Ala Thr
    1300                1305                1310 gca gaa atg ccc tat aat cca cag gct tct ggc ggg agc aat ctg                                                             4559
Ala Glu Met Pro Tyr Asn Pro Gln Ala Ser Gly Gly Ser Asn Leu
1315                1320                1325 gcg gtc agt aac cct gag ctg gat aaa cta ata gcc gca cgc gtt                                                             4604
Ala Val Ser Asn Pro Glu Leu Asp Lys Leu Ile Ala Ala Arg Val
            1330                1335                1340 gct gca tta cgg gcc gct aac ccg gat gcc agc gcg agc gtt ccg                                                             4649
Ala Ala Leu Arg Ala Ala Asn Pro Asp Ala Ser Ala Ser Val Pro
        1345                1350                1355 gtt gaa ctg gtg acg gca tcg gca agc ggg ctg gac aat aat atc                                                             4694
Val Glu Leu Val Thr Ala Ser Ala Ser Gly Leu Asp Asn Asn Ile
    1360                1365                1370 acc ccg caa gcg gcg gcc tgg caa atc cca cgc gtg gcg aaa gcg                                                             4739
Thr Pro Gln Ala Ala Ala Trp Gln Ile Pro Arg Val Ala Lys Ala
1375                1380                1385 cgt aat ctc agc gtt gaa cag ctc acg caa ctg atc gca aaa tac                                                             4784
Arg Asn Leu Ser Val Glu Gln Leu Thr Gln Leu Ile Ala Lys Tyr
            1390                1395                1400 agc caa caa ccg ctg gtg aaa tat atc ggc cag ccg gtt gtc aac                                                             4829
Ser Gln Gln Pro Leu Val Lys Tyr Ile Gly Gln Pro Val Val Asn
        1405                1410                1415 att gtt gaa ctc aat ctg gcg ctg gat aaa ctt gat gaa taa                                                                 4871
Ile Val Glu Leu Asn Leu Ala Leu Asp Lys Leu Asp Glu
    1420                1425 cgaaccctta cgtcccgacc ccgatcgtct gctggaacaa actgccgcgc cgcatcgggg                                                       4931
gaagctgaaa gttttcttcg gtgcctgtgc aggcgtcggg aagacctggg cgatgctggc                                                       4991
agaagcccag cgactgcggg cgcaagggct ggatattgtg gttggcgtgg tagaaaccca                                                       5051
cgggcgaaaa gataccgccg ccatgctgga agggctggct gttctgccgt aaaacgcca                                                        5111 ggcgtaccgt gggcggcata tcagcgagtt tgatctcgat gccgccctcg cccgccgccc                                                       5171
ggcgctgatc ttaatggacg aactggcgca cagtaatgcg ccaggttccc gtcatcccaa                                                       5231
acgctggcag gatatcgaag aactgctgga agctggcatt gatgttttca ctaccgtcaa                                                       5291
```

```
cgttcagcat ctggaaagtc tgaatgatgt ggtcagcggc gtcaccggaa ttcaggtacg    5351
ggaaaccgtg cccgatcctt ttttcgatgc cgccgacgac gtggtgctgg tggacttgcc    5411
cccggacgat ctgcgccagc ggctgaaaga aggcaaagtc tatattgccg ggcaggcgga    5471
gcgcgccatt gaacattttt tccgcaaagg taatctgatc gccctgcgcg aactggcact    5531
gcgccgtact gccgatcgcg ttgatgagca aatgcgcgcc tggcgggggc atcctggcga    5591
agagaaagtg tggcacacgc gcgacgcgat ccttttatgc atcggccata acaccggcag    5651
cgaaaaactg gtccgcgcag cggcgcggct ggcgtcacgg ctgggtagcg tctggcacgc    5711
ggtgtatgtt gaaccccctg ccctgcaccg cttaccggaa aaaaacgtc gggcaattct     5771 cagcgcctta cgtctggcgc aggaactggg cgcggagacg gcaacacttt ctgatccagc    5831
ggaagagaaa gcgtagtgc gttatgcccg tgaacataat ctcggcaaga ttattctcgg     5891
tcgcccggcc tcgcgccgct ggtggcgtcg ggaaacgttt gctgaccgac tggcgcgcat    5951
cgcccccgat ctcgatcagg tgctggtcgc gcttgatgaa ccacccgccc gcacgattaa    6011
caacgcgccg gataaccgct cttttaaaga caagtggcgt gtacaaattc agggatgcgt    6071
ggttgccgcc gcgttatgcg ccgttatcac cttaattgcc atgcagtggc tgatggcgtt    6131
tgatgccgcc aacctggtga tgctgtatct gcttggcgtg gtggtggtgg cgctatttta    6191
tggacgctgg ccttcagtgg ttgccaccgt cattaatgta gtgagtttcg atctcttttt    6251
tatcgcccca cgcggcacgc tcgccgtctc tgatgtgcaa tatctgctga ccttcgcggt    6311
gatgttaacc gtcgggctgg tgatcgggaa ccttactgct ggcgtgcgtt atcaggcgcg    6371
ggtagcccgt taccgcgagc aacgcacacg gcacttatat gaaatgtcga aagctctggc    6431
ggtgggccgc agtccgcagg atatcgctgc caccagcgaa caatttattg cctccacgtt    6491
tcatgcccgc agtcaggtgt tgttgcccga tgacaacggt aaattgcagc cgttaacaca    6551
tccgcaagga atgacgccgt gggacgatgc catcgcgcag tggagttttg ataaaggcct    6611
gcctgcgggc gcgggcaccg acacgttacc cggtgtaccg taccagattt tgccgctaaa    6671
aagcggcgag aaaacctacg ggctggtggt ggtggagccg gggaatctgc gccagttgat    6731
gatcccggaa cagcagcgcc tgctggagac gtttacgctg ttagtcgcca atgcccttga    6791
gcggctgacg ctaaccgcca gcgaagaaca ggcgcggatg gcaagcgaac gtgaacagat    6851
ccgcaacgcc ctgctggcgg cgcttttcgca tgatttacgc acgccgctta cggtgctgtt    6911
tggtcaggca gaaatcttaa cgctcgatct ggcaagcgaa ggatcacccc acgcccgcca    6971
ggccagcgag atccgtcagc atgtgctgaa cactacccga ctggtgaata atctactgga    7031
tatggcgcga attcagtccg gcggctttaa tttgaagaaa gagtggttaa cgctggaaga    7091
agtagtcggc agcgcgctgc aaatgctgga accgggttta tcgtcgccca tcaatctttc    7151
tctgccagaa ccgctgacct aatccacgt tgacgggcca ctctttgaac gggtgctgat     7211
taatctgctg gagaacgcgg tgaaatatgc gggtgcgcag gccgaaattg gtatcgatgc    7271
ccacgttgag ggcgaaaatc tacaactgga tgtctgggat aacggccccg gtcttccgcc    7331
aggccaggag cagacgatat ttgataagtt tgctcgcggg aataaagagt cggcagtacc    7391
gggggtaggg cttggactgg caatttgtcg ggcgatagtg gatgtacacg ggggcactat    7451
taccgcgttc aaccgaccgg aaggtggtgc ctgttttcgt gttacacttc cccagcaaac    7511 tgccccgaa cttgaagaat tcatgagga tatgtgacaa acgttctgat tgttgaagat      7571
gaacaggcta ttcgtcgctt tctgcgcacg gcgctgaggg gcgacgggat gcgcgtcttt    7631
gaggccgaaa cgctgcaacg cggcttgctg aagcggcaa cccgtaagcc agatttgatt     7691
```

-continued

```
attctcgatc tcggcctgcc cgatggtgat gggattgagt ttatccgcga cctgcgccag      7751
tggagcgcgg tgccggtgat tgtgctttcc gcacgcagcg aagagagcga caaaatcgcc      7811
gcgctggatg ccggagcgga tgattatctg agtaagccgt ttggcattgg cgaattgcag      7871
gcccgtctgc gcgtcgcatt acgccgccac tctgccacca ccgcgcccga tccgctggta      7931
aaattttccg atgttaccgt cgatttagcc gcccgcgtga ttcaccgggg tgaggaagag      7991
gtgcatctca caccaattga gttccgcctg ctggcggtgc tgctcaacaa tgccggaaaa      8051
gtactcaccc agcgccagct ccttaaccag gtgtggggc caaacgcggt cgaacacagt       8111
cactatttgc gtatttatat gggacatctg cgacaaaaac tggaacagga tcccgcccgc      8171
ccacgccatt tcattactga aaccggtatt ggctatcggt ttatgctttg aatattaatt      8231
ttaatacagc ctgccttta ttaattaaag ccgtaataat aaatacggct ttttatctta      8291
aacaacacac aaaaataaca attcaatatt ttatattact gagtaaaaag ctcatcatta      8351
aataaattaa gattgatcat tttttattga tcaccttcac agttcaaccg tatttcctgg      8411
atagaatatc ttcaccttca ttcacatcag gaaaggtaaa ttaaatggaa aataacagcc      8471
gcactatgcc ccatataagg cggacaactc                                       8501
```

<210> SEQ ID NO 2
<211> LENGTH: 557
<212> TYPE: PRT
<213> ORGANISM: Escherichia coli

<400> SEQUENCE: 2

```
Met Ala Ala Gln Gly Phe Leu Leu Ile Ala Thr Phe Leu Leu Val Leu
1               5                   10                  15

Met Val Leu Ala Arg Pro Leu Gly Ser Gly Leu Ala Arg Leu Ile Asn
            20                  25                  30

Asp Ile Pro Leu Pro Gly Thr Thr Gly Val Glu Arg Val Leu Phe Arg
        35                  40                  45

Ala Leu Gly Val Ser Asp Arg Glu Met Asn Trp Lys Gln Tyr Leu Cys
    50                  55                  60

Ala Ile Leu Gly Leu Asn Met Leu Gly Leu Ala Val Leu Phe Phe Met
65                  70                  75                  80

Leu Leu Gly Gln His Tyr Leu Pro Leu Asn Pro Gln Gln Leu Pro Gly
                85                  90                  95

Leu Ser Trp Asp Leu Ala Leu Asn Thr Ala Val Ser Phe Val Thr Asn
            100                 105                 110

Thr Asn Trp Gln Ser Tyr Ser Gly Glu Thr Thr Leu Ser Tyr Phe Ser
        115                 120                 125

Gln Met Ala Gly Leu Thr Val Gln Asn Phe Leu Ser Ala Ala Ser Gly
    130                 135                 140

Ile Ala Val Ile Phe Ala Leu Ile Arg Ala Phe Thr Arg Gln Ser Met
145                 150                 155                 160

Ser Thr Leu Gly Asn Ala Trp Val Asp Leu Leu Arg Ile Thr Leu Trp
                165                 170                 175

Val Leu Val Pro Val Ala Leu Leu Ile Ala Leu Phe Phe Ile Gln Gln
            180                 185                 190

Gly Ala Leu Gln Asn Phe Leu Pro Tyr Gln Ala Val Asn Thr Val Glu
        195                 200                 205

Gly Ala Gln Gln Leu Leu Pro Met Gly Pro Val Ala Ser Gln Glu Ala
    210                 215                 220

Ile Lys Met Leu Gly Thr Asn Gly Gly Gly Phe Phe Asn Ala Asn Ser
225                 230                 235                 240
```

Ser His Pro Phe Glu Asn Pro Thr Ala Leu Thr Asn Phe Val Gln Met
            245                 250                 255

Leu Ala Ile Phe Leu Ile Pro Thr Ala Leu Cys Phe Ala Phe Gly Glu
        260                 265                 270

Val Met Gly Asp Arg Arg Gln Gly Arg Met Leu Leu Trp Ala Met Ser
            275                 280                 285

Val Ile Phe Val Ile Cys Val Gly Val Val Met Trp Ala Glu Val Gln
        290                 295                 300

Gly Asn Pro His Leu Leu Ala Leu Gly Thr Asp Ser Ser Ile Asn Met
305                 310                 315                 320

Glu Gly Lys Glu Ser Arg Phe Gly Val Leu Val Ser Ser Leu Phe Ala
                325                 330                 335

Val Val Thr Thr Ala Ala Ser Cys Gly Ala Val Ile Ala Met His Asp
            340                 345                 350

Ser Phe Thr Ala Leu Gly Gly Met Val Pro Met Trp Leu Met Gln Ile
        355                 360                 365

Gly Glu Val Val Phe Gly Gly Val Gly Ser Gly Leu Tyr Gly Met Met
    370                 375                 380

Leu Phe Val Leu Leu Ala Val Phe Ile Ala Gly Leu Met Ile Gly Arg
385                 390                 395                 400

Thr Pro Glu Tyr Leu Gly Lys Lys Ile Asp Val Arg Glu Met Lys Leu
                405                 410                 415

Thr Ala Leu Ala Ile Leu Val Thr Pro Thr Leu Val Leu Met Gly Ala
            420                 425                 430

Ala Leu Ala Met Met Thr Asp Ala Gly Arg Ser Ala Met Leu Asn Pro
        435                 440                 445

Gly Pro His Gly Phe Ser Glu Val Leu Tyr Ala Val Ser Ser Ala Ala
    450                 455                 460

Asn Asn Asn Gly Ser Ala Phe Ala Gly Leu Ser Ala Asn Ser Pro Phe
465                 470                 475                 480

Trp Asn Cys Leu Leu Ala Phe Cys Met Phe Val Gly Arg Phe Gly Val
                485                 490                 495

Ile Ile Pro Val Met Ala Ile Ala Gly Ser Leu Val Ser Lys Lys Ser
            500                 505                 510

Gln Ala Ala Ser Ser Gly Thr Leu Pro Thr His Gly Pro Leu Phe Val
        515                 520                 525

Gly Leu Leu Ile Gly Thr Val Leu Leu Val Gly Ala Leu Thr Phe Ile
    530                 535                 540

Pro Ala Leu Ala Leu Gly Pro Val Ala Glu Tyr Leu Ser
545                 550                 555

<210> SEQ ID NO 3
<211> LENGTH: 682
<212> TYPE: PRT
<213> ORGANISM: Escherichia coli

<400> SEQUENCE: 3

Met Ser Arg Lys Gln Leu Ala Leu Phe Glu Pro Thr Leu Val Val Gln
1               5                   10                  15

Ala Leu Lys Glu Ala Val Lys Lys Leu Asn Pro Gln Ala Gln Trp Arg
            20                  25                  30

Asn Pro Val Met Phe Ile Val Trp Ile Gly Ser Leu Leu Thr Thr Cys
        35                  40                  45

Ile Ser Ile Ala Met Ala Ser Gly Ala Met Pro Gly Asn Ala Leu Phe
    50                  55                  60

Ser Ala Ala Ile Ser Gly Trp Leu Trp Ile Thr Val Leu Phe Ala Asn
 65                  70                  75                  80

Phe Ala Glu Ala Leu Ala Glu Gly Arg Ser Lys Ala Gln Ala Asn Ser
             85                  90                  95

Leu Lys Gly Val Lys Lys Thr Ala Phe Ala Arg Lys Leu Arg Glu Pro
            100                 105                 110

Lys Tyr Gly Ala Ala Asp Lys Val Pro Ala Asp Gln Leu Arg Lys
            115                 120                 125

Gly Asp Ile Val Leu Val Glu Ala Gly Asp Ile Ile Pro Cys Asp Gly
            130                 135                 140

Glu Val Ile Glu Gly Gly Ala Ser Val Asp Glu Ser Ala Ile Thr Gly
145                 150                 155                 160

Glu Ser Ala Pro Val Ile Arg Glu Ser Gly Asp Phe Ala Ser Val
            165                 170                 175

Thr Gly Gly Thr Arg Ile Leu Ser Asp Trp Leu Val Ile Glu Cys Ser
            180                 185                 190

Val Asn Pro Gly Glu Thr Phe Leu Asp Arg Met Ile Ala Met Val Glu
            195                 200                 205

Gly Ala Gln Arg Arg Lys Thr Pro Asn Glu Ile Ala Leu Thr Ile Leu
            210                 215                 220

Leu Ile Ala Leu Thr Ile Val Phe Leu Leu Ala Thr Ala Thr Leu Trp
225                 230                 235                 240

Pro Phe Ser Ala Trp Gly Gly Asn Ala Val Ser Val Thr Val Leu Val
            245                 250                 255

Ala Leu Leu Val Cys Leu Ile Pro Thr Thr Ile Gly Gly Leu Leu Ser
            260                 265                 270

Ala Ile Gly Val Ala Gly Met Ser Arg Met Leu Gly Ala Asn Val Ile
            275                 280                 285

Ala Thr Ser Gly Arg Ala Val Glu Ala Ala Gly Asp Val Asp Val Leu
            290                 295                 300

Leu Leu Asp Lys Thr Gly Thr Ile Thr Leu Gly Asn Arg Gln Ala Ser
305                 310                 315                 320

Glu Phe Ile Pro Ala Gln Gly Val Asp Glu Lys Thr Leu Ala Asp Ala
            325                 330                 335

Ala Gln Leu Ala Ser Leu Ala Asp Glu Thr Pro Glu Gly Arg Ser Ile
            340                 345                 350

Val Ile Leu Ala Lys Gln Arg Phe Asn Leu Arg Glu Arg Asp Val Gln
            355                 360                 365

Ser Leu His Ala Thr Phe Val Pro Phe Thr Ala Gln Ser Arg Met Ser
            370                 375                 380

Gly Ile Asn Ile Asp Asn Arg Met Ile Arg Lys Gly Ser Val Asp Ala
385                 390                 395                 400

Ile Arg Arg His Val Glu Ala Asn Gly Gly His Phe Pro Thr Asp Val
            405                 410                 415

Asp Gln Lys Val Asp Gln Val Ala Arg Gln Gly Ala Thr Pro Leu Val
            420                 425                 430

Val Val Glu Gly Ser Arg Val Leu Gly Val Ile Ala Leu Lys Asp Ile
            435                 440                 445

Val Lys Gly Gly Ile Lys Glu Arg Phe Ala Gln Leu Arg Lys Met Gly
            450                 455                 460

Ile Lys Thr Val Met Ile Thr Gly Asp Asn Arg Leu Thr Ala Ala Ala
465                 470                 475                 480

Ile Ala Ala Glu Ala Gly Val Asp Asp Phe Leu Ala Glu Ala Thr Pro

```
                        485                 490                 495
Glu Ala Lys Leu Ala Leu Ile Arg Gln Tyr Gln Ala Glu Gly Arg Leu
                500                 505                 510

Val Ala Met Thr Gly Asp Gly Thr Asn Asp Ala Pro Ala Leu Ala Gln
            515                 520                 525

Ala Asp Val Ala Val Ala Met Asn Ser Gly Thr Gln Ala Ala Lys Glu
        530                 535                 540

Ala Gly Asn Met Val Asp Leu Asp Ser Asn Pro Thr Lys Leu Ile Glu
545                 550                 555                 560

Val Val His Ile Gly Lys Gln Met Leu Met Thr Arg Gly Ser Leu Thr
                565                 570                 575

Thr Phe Ser Ile Ala Asn Asp Val Ala Lys Tyr Phe Ala Ile Ile Pro
            580                 585                 590

Ala Ala Phe Ala Ala Thr Tyr Pro Gln Leu Asn Ala Leu Asn Ile Met
        595                 600                 605

Cys Leu His Ser Pro Asp Ser Ala Ile Leu Ser Ala Val Ile Phe Asn
    610                 615                 620

Ala Leu Ile Ile Val Phe Leu Ile Pro Leu Ala Leu Lys Gly Val Ser
625                 630                 635                 640

Tyr Lys Pro Leu Thr Ala Ser Ala Met Leu Arg Arg Asn Leu Trp Ile
                645                 650                 655

Tyr Gly Leu Gly Gly Leu Leu Val Pro Phe Ile Gly Ile Lys Val Ile
            660                 665                 670

Asp Leu Leu Leu Thr Val Cys Gly Leu Val
        675                 680

<210> SEQ ID NO 4
<211> LENGTH: 190
<212> TYPE: PRT
<213> ORGANISM: Escherichia coli

<400> SEQUENCE: 4

Met Ser Gly Leu Arg Pro Ala Leu Ser Thr Phe Ile Phe Leu Leu Leu
1               5                   10                  15

Ile Thr Gly Gly Val Tyr Pro Leu Leu Thr Thr Val Leu Gly Gln Trp
                20                  25                  30

Trp Phe Pro Trp Gln Ala Asn Gly Ser Leu Ile Arg Glu Gly Asp Thr
            35                  40                  45

Val Arg Gly Ser Ala Leu Ile Gly Gln Asn Phe Thr Gly Asn Gly Tyr
        50                  55                  60

Phe His Gly Arg Pro Ser Ala Thr Ala Glu Met Pro Tyr Asn Pro Gln
65                  70                  75                  80

Ala Ser Gly Gly Ser Asn Leu Ala Val Ser Asn Pro Glu Leu Asp Lys
                85                  90                  95

Leu Ile Ala Ala Arg Val Ala Ala Leu Arg Ala Ala Asn Pro Asp Ala
            100                 105                 110

Ser Ala Ser Val Pro Val Glu Leu Val Thr Ala Ser Ala Ser Gly Leu
        115                 120                 125

Asp Asn Asn Ile Thr Pro Gln Ala Ala Ala Trp Gln Ile Pro Arg Val
    130                 135                 140

Ala Lys Ala Arg Asn Leu Ser Val Glu Gln Leu Thr Gln Leu Ile Ala
145                 150                 155                 160

Lys Tyr Ser Gln Gln Pro Leu Val Lys Tyr Ile Gly Gln Pro Val Val
                165                 170                 175

Asn Ile Val Glu Leu Asn Leu Ala Leu Asp Lys Leu Asp Glu
            180                 185                 190
```

```
                180                 185                 190

<210> SEQ ID NO 5
<211> LENGTH: 894
<212> TYPE: PRT
<213> ORGANISM: Escherichia coli

<400> SEQUENCE: 5

Met Asn Glu Pro Leu Arg Pro Asp Pro Asp Arg Leu Leu Glu Gln
1               5                   10                  15

Thr Ala Ala Pro His Arg Gly Lys Leu Lys Val Phe Gly Ala Cys
                20                  25                  30

Ala Gly Val Gly Lys Thr Trp Ala Met Leu Ala Glu Ala Gln Arg Leu
            35                  40                  45

Arg Ala Gln Gly Leu Asp Ile Val Val Gly Val Glu Thr His Gly
        50                  55                  60

Arg Lys Asp Thr Ala Ala Met Leu Glu Gly Leu Ala Val Leu Pro Leu
65                  70                  75                  80

Lys Arg Gln Ala Tyr Arg Gly Arg His Ile Ser Glu Phe Asp Leu Asp
                85                  90                  95

Ala Ala Leu Ala Arg Arg Pro Ala Leu Ile Leu Met Asp Glu Leu Ala
                100                 105                 110

His Ser Asn Ala Pro Gly Ser Arg His Pro Lys Arg Trp Gln Asp Ile
                115                 120                 125

Glu Glu Leu Leu Glu Ala Gly Ile Asp Val Phe Thr Thr Val Asn Val
            130                 135                 140

Gln His Leu Glu Ser Leu Asn Asp Val Val Ser Gly Val Thr Gly Ile
145                 150                 155                 160

Gln Val Arg Glu Thr Val Pro Asp Pro Phe Phe Asp Ala Ala Asp Asp
                165                 170                 175

Val Val Leu Val Asp Leu Pro Pro Asp Asp Leu Arg Gln Arg Leu Lys
                180                 185                 190

Glu Gly Lys Val Tyr Ile Ala Gly Gln Ala Glu Arg Ala Ile Glu His
            195                 200                 205

Phe Phe Arg Lys Gly Asn Leu Ile Ala Leu Arg Glu Leu Ala Leu Arg
210                 215                 220

Arg Thr Ala Asp Arg Val Asp Glu Gln Met Arg Ala Trp Arg Gly His
225                 230                 235                 240

Pro Gly Glu Glu Lys Val Trp His Thr Arg Asp Ala Ile Leu Leu Cys
                245                 250                 255

Ile Gly His Asn Thr Gly Ser Glu Lys Leu Val Arg Ala Ala Ala Arg
                260                 265                 270

Leu Ala Ser Arg Leu Gly Ser Val Trp His Ala Val Tyr Val Glu Thr
            275                 280                 285

Pro Ala Leu His Arg Leu Pro Glu Lys Lys Arg Arg Ala Ile Leu Ser
        290                 295                 300

Ala Leu Arg Leu Ala Gln Glu Leu Gly Ala Glu Thr Ala Thr Leu Ser
305                 310                 315                 320

Asp Pro Ala Glu Glu Lys Ala Val Val Arg Tyr Ala Arg Glu His Asn
                325                 330                 335

Leu Gly Lys Ile Ile Leu Gly Arg Pro Ala Ser Arg Arg Trp Trp Arg
                340                 345                 350

Arg Glu Thr Phe Ala Asp Arg Leu Ala Arg Ile Ala Pro Asp Leu Asp
            355                 360                 365

Gln Val Leu Val Ala Leu Asp Glu Pro Pro Ala Arg Thr Ile Asn Asn
```

-continued

```
            370                 375                 380
Ala Pro Asp Asn Arg Ser Phe Lys Asp Lys Trp Arg Val Gln Ile Gln
385                 390                 395                 400

Gly Cys Val Val Ala Ala Leu Cys Ala Val Ile Thr Leu Ile Ala
                405                 410                 415

Met Gln Trp Leu Met Ala Phe Asp Ala Ala Asn Leu Val Met Leu Tyr
                420                 425                 430

Leu Leu Gly Val Val Val Ala Leu Phe Tyr Gly Arg Trp Pro Ser
                435                 440                 445

Val Val Ala Thr Val Ile Asn Val Val Ser Phe Asp Leu Phe Phe Ile
                450                 455                 460

Ala Pro Arg Gly Thr Leu Ala Val Ser Asp Val Gln Tyr Leu Leu Thr
465                 470                 475                 480

Phe Ala Val Met Leu Thr Val Gly Leu Val Ile Gly Asn Leu Thr Ala
                485                 490                 495

Gly Val Arg Tyr Gln Ala Arg Val Ala Arg Tyr Arg Glu Gln Arg Thr
                500                 505                 510

Arg His Leu Tyr Glu Met Ser Lys Ala Leu Ala Val Gly Arg Ser Pro
                515                 520                 525

Gln Asp Ile Ala Ala Thr Ser Glu Gln Phe Ile Ala Ser Thr Phe His
530                 535                 540

Ala Arg Ser Gln Val Leu Leu Pro Asp Asp Asn Gly Lys Leu Gln Pro
545                 550                 555                 560

Leu Thr His Pro Gln Gly Met Thr Pro Trp Asp Asp Ala Ile Ala Gln
                565                 570                 575

Trp Ser Phe Asp Lys Gly Leu Pro Ala Gly Ala Gly Thr Asp Thr Leu
                580                 585                 590

Pro Gly Val Pro Tyr Gln Ile Leu Pro Leu Lys Ser Gly Glu Lys Thr
                595                 600                 605

Tyr Gly Leu Val Val Val Glu Pro Gly Asn Leu Arg Gln Leu Met Ile
                610                 615                 620

Pro Glu Gln Gln Arg Leu Leu Glu Thr Phe Thr Leu Leu Val Ala Asn
625                 630                 635                 640

Ala Leu Glu Arg Leu Thr Leu Thr Ala Ser Glu Gln Ala Arg Met
                645                 650                 655

Ala Ser Glu Arg Glu Gln Ile Arg Asn Ala Leu Leu Ala Ala Leu Ser
                660                 665                 670

His Asp Leu Arg Thr Pro Leu Thr Val Leu Phe Gly Gln Ala Glu Ile
                675                 680                 685

Leu Thr Leu Asp Leu Ala Ser Glu Gly Ser Pro His Ala Arg Gln Ala
                690                 695                 700

Ser Glu Ile Arg Gln His Val Leu Asn Thr Thr Arg Leu Val Asn Asn
705                 710                 715                 720

Leu Leu Asp Met Ala Arg Ile Gln Ser Gly Phe Asn Leu Lys Lys
                725                 730                 735

Glu Trp Leu Thr Leu Glu Glu Val Val Gly Ser Ala Leu Gln Met Leu
                740                 745                 750

Glu Pro Gly Leu Ser Ser Pro Ile Asn Leu Ser Leu Pro Glu Pro Leu
                755                 760                 765

Thr Leu Ile His Val Asp Gly Pro Leu Phe Glu Arg Val Leu Ile Asn
                770                 775                 780

Leu Leu Glu Asn Ala Val Lys Tyr Ala Gly Ala Gln Ala Glu Ile Gly
785                 790                 795                 800
```

```
Ile Asp Ala His Val Glu Gly Glu Asn Leu Gln Leu Asp Val Trp Asp
                805                 810                 815

Asn Gly Pro Gly Leu Pro Pro Gly Gln Gln Thr Ile Phe Asp Lys
            820                 825                 830

Phe Ala Arg Gly Asn Lys Glu Ser Ala Val Pro Gly Val Gly Leu Gly
        835                 840                 845

Leu Ala Ile Cys Arg Ala Ile Val Asp Val His Gly Gly Thr Ile Thr
    850                 855                 860

Ala Phe Asn Arg Pro Glu Gly Gly Ala Cys Phe Arg Val Thr Leu Pro
865                 870                 875                 880

Gln Gln Thr Ala Pro Glu Leu Glu Glu Phe His Glu Asp Met
                885                 890
```

<210> SEQ ID NO 6
<211> LENGTH: 225
<212> TYPE: PRT
<213> ORGANISM: Escherichia coli

<400> SEQUENCE: 6

```
Val Thr Asn Val Leu Ile Val Glu Asp Glu Gln Ala Ile Arg Arg Phe
1               5                   10                  15

Leu Arg Thr Ala Leu Glu Gly Asp Gly Met Arg Val Phe Glu Ala Glu
            20                  25                  30

Thr Leu Gln Arg Gly Leu Leu Glu Ala Ala Thr Arg Lys Pro Asp Leu
        35                  40                  45

Ile Ile Leu Asp Leu Gly Leu Pro Asp Gly Asp Gly Ile Glu Phe Ile
    50                  55                  60

Arg Asp Leu Arg Gln Trp Ser Ala Val Pro Val Ile Val Leu Ser Ala
65                  70                  75                  80

Arg Ser Glu Glu Ser Asp Lys Ile Ala Ala Leu Asp Ala Gly Ala Asp
                85                  90                  95

Asp Tyr Leu Ser Lys Pro Phe Gly Ile Gly Glu Leu Gln Ala Arg Leu
            100                 105                 110

Arg Val Ala Leu Arg Arg His Ser Ala Thr Thr Ala Pro Asp Pro Leu
        115                 120                 125

Val Lys Phe Ser Asp Val Thr Val Asp Leu Ala Ala Arg Val Ile His
    130                 135                 140

Arg Gly Glu Glu Glu Val His Leu Thr Pro Ile Glu Phe Arg Leu Leu
145                 150                 155                 160

Ala Val Leu Leu Asn Asn Ala Gly Lys Val Leu Thr Gln Arg Gln Leu
                165                 170                 175

Leu Asn Gln Val Trp Gly Pro Asn Ala Val Glu His Ser His Tyr Leu
            180                 185                 190

Arg Ile Tyr Met Gly His Leu Arg Gln Lys Leu Glu Gln Asp Pro Ala
        195                 200                 205

Arg Pro Arg His Phe Ile Thr Glu Thr Gly Ile Gly Tyr Arg Phe Met
    210                 215                 220

Leu
225
```

<210> SEQ ID NO 7
<211> LENGTH: 7620
<212> TYPE: DNA
<213> ORGANISM: Pantoea
<220> FEATURE:
<221> NAME/KEY: CDS
<222> LOCATION: (543)..(2225)
<220> FEATURE:

```
<221> NAME/KEY: CDS
<222> LOCATION: (2228)..(4273)
<220> FEATURE:
<221> NAME/KEY: CDS
<222> LOCATION: (4284)..(4853)
<220> FEATURE:
<221> NAME/KEY: CDS
<222> LOCATION: (4867)..(7542)

<400> SEQUENCE: 7
```

| | | |
|---|---|---|
| aggctggacc ccagccaaaa ccctgcaaat gatgttgagc tggccggggc atttcgacag | 60 |
| taccttactg cacgctttcg tcagtacgat agggatgtat cccgtcggtt ccctggttcg | 120 |
| cctggcgtct ggacgcattg cgctggtggt gaagggcggc gataagtcat tacagcgacc | 180 |
| tacggtgcat gtcttctggt cactgcacgc gcagcgggaa atcaaacccg aggtgctgga | 240 |
| tctgggcgac agttttgta ctgacagcat tgtgtgtgcc gaagataacg gccgttggga | 300 |
| caacgtcgat ctgcgccgaa tctggttgct ggacgccgcc tgatattgcg ggtcgttttt | 360 |
| atacattttt tacatccccg acccgcattt taacccttc tttatgtgcg ccagcgcaag | 420 |
| ctactcagca aatccaatcc tctggaggtt gctgtgagtg caggcgtaat aaccggcatt | 480 |
| gtgctggtag tgttgttgct gggctatctg atctatgccc tgttaaatgc ggaggccttc | 540 |

```
tg atg gcg gcc aat gcg ttt tta ctg atc gcg gtt tat ctg ctg ttg       587
   Met Ala Ala Asn Ala Phe Leu Leu Ile Ala Val Tyr Leu Leu Leu
   1               5                  10                 15 ctg atg gtg atg gcg caa ccg ctg ggg cgt ggg ctg gcc gcg ctg gtt      635
Leu Met Val Met Ala Gln Pro Leu Gly Arg Gly Leu Ala Ala Leu Val
            20                   25                  30 gcc gat aaa ccc ctc ttt gca cgt gct gaa gcc ctg ctg tgg cgt ttt      683
Ala Asp Lys Pro Leu Phe Ala Arg Ala Glu Ala Leu Leu Trp Arg Phe
        35                  40                  45 tcg ggt gta caa gaa ggc ggt atg cgc tgg cag cac tac ctg ctg gca      731
Ser Gly Val Gln Glu Gly Gly Met Arg Trp Gln His Tyr Leu Leu Ala
    50                  55                  60 att ttg gtg ttc aac ctg ctt ggc ttc gtg gtg ctg ctc gcc atc cta      779
Ile Leu Val Phe Asn Leu Leu Gly Phe Val Val Leu Leu Ala Ile Leu
65                  70                  75 atg ttt cag gga gcg ttg ccg ctc aat ccg caa cat ctt ccc gga ctg      827
Met Phe Gln Gly Ala Leu Pro Leu Asn Pro Gln His Leu Pro Gly Leu
80                  85                  90                  95 agc tgg gat ttg gcg ctg aat acc gct atc agt ttt gtc acc aac acc      875
Ser Trp Asp Leu Ala Leu Asn Thr Ala Ile Ser Phe Val Thr Asn Thr
            100                 105                 110 aac tgg cag tct tat gcc ggt gaa agc acc ctg agt tac ttc agc cag      923
Asn Trp Gln Ser Tyr Ala Gly Glu Ser Thr Leu Ser Tyr Phe Ser Gln
        115                 120                 125 atg gtc ggg ctg acg gtg cag aac ttc gtt tcc gcc gcc acc ggc atc      971
Met Val Gly Leu Thr Val Gln Asn Phe Val Ser Ala Ala Thr Gly Ile
    130                 135                 140 gcc gtg gcg ttt gcg ctg att cgc ggt ttt gct aat cgt tcg gtg gca     1019
Ala Val Ala Phe Ala Leu Ile Arg Gly Phe Ala Asn Arg Ser Val Ala
145                 150                 155 acc ctg ggc aac gcc tgg cgc gat tta acg cgc att aca ctc tat gtc     1067
Thr Leu Gly Asn Ala Trp Arg Asp Leu Thr Arg Ile Thr Leu Tyr Val
160                 165                 170                 175 ctg ttg ccg atc agc ctg ctg atg gcg ctg ttt ttt gtc agc cag ggc     1115
Leu Leu Pro Ile Ser Leu Leu Met Ala Leu Phe Phe Val Ser Gln Gly
            180                 185                 190 agc atc cag aac ttc ctg ccg tat cac aac gtc acc agc ctg gaa ggt     1163
Ser Ile Gln Asn Phe Leu Pro Tyr His Asn Val Thr Ser Leu Glu Gly
        195                 200                 205
```

-continued

| | |
|---|---|
| gcg cag caa acg ctg gca atg ggg ccg gtt gcc tct cag gaa gcc atc<br>Ala Gln Gln Thr Leu Ala Met Gly Pro Val Ala Ser Gln Glu Ala Ile<br>210                                 215                            220 | 1211 |
| aaa atg ctg ggc acc aac ggc ggc ttt ttc aac gtt aac tct gcg<br>Lys Met Leu Gly Thr Asn Gly Gly Phe Phe Asn Val Asn Ser Ala<br>225                         230                            235 | 1259 |
| cat ccg ttt gag aac cct acc gcg ctg agc aat ttc gta cag atg ctt<br>His Pro Phe Glu Asn Pro Thr Ala Leu Ser Asn Phe Val Gln Met Leu<br>240                                 245                      250                      255 | 1307 |
| agt atc ttc ctg att cct gca gca ctc tgc ttt gcc ttt ggc gaa agc<br>Ser Ile Phe Leu Ile Pro Ala Ala Leu Cys Phe Ala Phe Gly Glu Ser<br>                             260                      265                      270 | 1355 |
| gtt aaa gat cgg cgc cag ggc tca atg ttg ctc tgg tcc atg acg ttg<br>Val Lys Asp Arg Arg Gln Gly Ser Met Leu Leu Trp Ser Met Thr Leu<br>        275                           280                            285 | 1403 |
| atg ttt gtc gtg gct gct gcg ctg gtg atg tgg gct gaa cta cgt ggc<br>Met Phe Val Val Ala Ala Ala Leu Val Met Trp Ala Glu Leu Arg Gly<br>              290                         295                      300 | 1451 |
| aac ccg cac ttt ctg acg cta ggg gct gac agc gcc atc aat atg gaa<br>Asn Pro His Phe Leu Thr Leu Gly Ala Asp Ser Ala Ile Asn Met Glu<br>305                                 310                      315 | 1499 |
| ggc aaa gaa acg cgc ttc ggc att ctc aac tcc agc ctg ttt gcg gtg<br>Gly Lys Glu Thr Arg Phe Gly Ile Leu Asn Ser Ser Leu Phe Ala Val<br>320                           325                      330                      335 | 1547 |
| att acg acg gcg gcg tcc tgc ggt gcg gta aac gcg atg cat gac tcg<br>Ile Thr Thr Ala Ala Ser Cys Gly Ala Val Asn Ala Met His Asp Ser<br>                             340                      345                      350 | 1595 |
| ttt acg gcg ctg ggc ggt atg gtg ccg atg ctg ctg atg caa ctg ggc<br>Phe Thr Ala Leu Gly Gly Met Val Pro Met Leu Leu Met Gln Leu Gly<br>              355                         360                      365 | 1643 |
| gag gtg gtg ttt ggc ggc gtg ggt gcc ggt ctg tac ggg atg ctg ctg<br>Glu Val Val Phe Gly Gly Val Gly Ala Gly Leu Tyr Gly Met Leu Leu<br>370                                 375                      380 | 1691 |
| ttt gtc tta ctg gcg gtg ttt att gcc ggg ttg atg att ggc cgc aca<br>Phe Val Leu Leu Ala Val Phe Ile Ala Gly Leu Met Ile Gly Arg Thr<br>        385                           390                            395 | 1739 |
| ccg gaa ttc ctc ggc aag aaa atc gac gta tgg gaa atg aaa atg acg<br>Pro Glu Phe Leu Gly Lys Lys Ile Asp Val Trp Glu Met Lys Met Thr<br>400                                 405                      410                      415 | 1787 |
| gcc ctg gcg att ctg gtc acg ccc gcg ctg gtg ttg atc ggt acg gcg<br>Ala Leu Ala Ile Leu Val Thr Pro Ala Leu Val Leu Ile Gly Thr Ala<br>                      420                      425                      430 | 1835 |
| att gcg atg atg acc gac gcc gga cgc gca ggt atg gca aac ccc gga<br>Ile Ala Met Met Thr Asp Ala Gly Arg Ala Gly Met Ala Asn Pro Gly<br>                             435                      440                      445 | 1883 |
| acg cat ggc ttt agt gaa gtc ctg tat gcc gtt tcg tcg gcc gcc aat<br>Thr His Gly Phe Ser Glu Val Leu Tyr Ala Val Ser Ser Ala Ala Asn<br>              450                         455                      460 | 1931 |
| aac aat ggc agc gcc ttt gcg ggc ctg aac gcc aat acg ccg ttc tgg<br>Asn Asn Gly Ser Ala Phe Ala Gly Leu Asn Ala Asn Thr Pro Phe Trp<br>465                                 470                      475 | 1979 |
| aac ctg ctg ctg gcg gtg tgt atg ttc gta ggt cgc ttc ggc atc att<br>Asn Leu Leu Leu Ala Val Cys Met Phe Val Gly Arg Phe Gly Ile Ile<br>480                                 485                      490                      495 | 2027 |
| att ccg gtc atg gcg att gcg ggg gca atg gcg gtg aaa aaa gtg cag<br>Ile Pro Val Met Ala Ile Ala Gly Ala Met Ala Val Lys Lys Val Gln<br>                      500                      505                      510 | 2075 |
| ccg gta ggt aac ggc acg ctc cct acg cac ggt ccg ctg ttt atc gca<br>Pro Val Gly Asn Gly Thr Leu Pro Thr His Gly Pro Leu Phe Ile Ala<br>              515                      520                      525 | 2123 |

```
ctg ctg gtc ggt acc gtc ttg ttg gtc ggc gcg ctg acc ttt att cct     2171
Leu Leu Val Gly Thr Val Leu Leu Val Gly Ala Leu Thr Phe Ile Pro
        530             535                 540 gct ctg gcg ctg ggt ccg gtc gcc gag cac ctg caa ctt att cag gga     2219
Ala Leu Ala Leu Gly Pro Val Ala Glu His Leu Gln Leu Ile Gln Gly
545                 550                 555 caa taa tc atg agt cgt caa caa cag gtg ttt gac gca gcg ctg tta      2266
Gln     Met Ser Arg Gln Gln Gln Val Phe Asp Ala Ala Leu Leu
560             565                 570 cgt acc tca gcg atc gat gcg gta aaa aaa ctc gat cct cgc gtg cag     2314
Arg Thr Ser Ala Ile Asp Ala Val Lys Lys Leu Asp Pro Arg Val Gln
    575                 580                 585 ttt cgc aat ccg gtc atg ttt gtg gtt tac ctg ggc agt atc ctg acc     2362
Phe Arg Asn Pro Val Met Phe Val Val Tyr Leu Gly Ser Ile Leu Thr
590                 595                 600                 605 tcg att ctg gcc ata atg atg ttt acc gga cac cag agc ggc agc gcc     2410
Ser Ile Leu Ala Ile Met Met Phe Thr Gly His Gln Ser Gly Ser Ala
                610                 615                 620 agc ttt acc ggc gcg att gcc ctg tgg tta tgg ttc acc gtg ctg ttt     2458
Ser Phe Thr Gly Ala Ile Ala Leu Trp Leu Trp Phe Thr Val Leu Phe
            625                 630                 635 gcc aac atg gca gaa gcc ctg gcg gaa ggg cgc agt aaa gcc cag gca     2506
Ala Asn Met Ala Glu Ala Leu Ala Glu Gly Arg Ser Lys Ala Gln Ala
        640                 645                 650 aac agc ctg aaa ggc gtt aaa aag acc agc ttc gcc aaa aaa ctg tcg     2554
Asn Ser Leu Lys Gly Val Lys Lys Thr Ser Phe Ala Lys Lys Leu Ser
    655                 660                 665 gcg gcg cac tac ggt gca gcg tgg cag cag gtg gcg gcc gat gcg ctg     2602
Ala Ala His Tyr Gly Ala Ala Trp Gln Gln Val Ala Ala Asp Ala Leu
670                 675                 680                 685 cgt aaa ggg gat gcc gtg ctg gta gag gcc ggt gat gtg atc ccc tgc     2650
Arg Lys Gly Asp Ala Val Leu Val Glu Ala Gly Asp Val Ile Pro Cys
                690                 695                 700 gac ggt gaa gtc gtg gaa ggg ggc gca tcg gta gac gag agc gcg atc     2698
Asp Gly Glu Val Val Glu Gly Gly Ala Ser Val Asp Glu Ser Ala Ile
            705                 710                 715 acc ggt gaa tcg gca ccg gtg atc cgt gaa tcg ggc ggg gat ttc gcc     2746
Thr Gly Glu Ser Ala Pro Val Ile Arg Glu Ser Gly Gly Asp Phe Ala
        720                 725                 730 tcg gtg acc ggc ggg aca cgc att ctg tct gac tgg ctg gtc att acc     2794
Ser Val Thr Gly Gly Thr Arg Ile Leu Ser Asp Trp Leu Val Ile Thr
    735                 740                 745 tgc agc gcc aac cca ggc gaa acc ttc ctg gac cgg atg atc gcc atg     2842
Cys Ser Ala Asn Pro Gly Glu Thr Phe Leu Asp Arg Met Ile Ala Met
750                 755                 760                 765 gtc gaa ggc gca cag cgt cgt aaa acc ccg aat gag att gcc ctg acc     2890
Val Glu Gly Ala Gln Arg Arg Lys Thr Pro Asn Glu Ile Ala Leu Thr
                770                 775                 780 att ctg ctg gtg tcg ctc acc att gtg ttt ctg tta gcc acc gtc acg     2938
Ile Leu Leu Val Ser Leu Thr Ile Val Phe Leu Leu Ala Thr Val Thr
            785                 790                 795 ctg tgg cct ttt tca gcc tgg ggc ggc acg ccg gtc acc atc acc gta     2986
Leu Trp Pro Phe Ser Ala Trp Gly Gly Thr Pro Val Thr Ile Thr Val
        800                 805                 810 ctg gtg gcg ctg ctg gta tgc ctg atc ccg acc acc att ggc ggt ctg     3034
Leu Val Ala Leu Leu Val Cys Leu Ile Pro Thr Thr Ile Gly Gly Leu
    815                 820                 825 ctg tcc gct atc ggc gtg gcc ggg atg agc cgg atg ctg ggc gct aac     3082
Leu Ser Ala Ile Gly Val Ala Gly Met Ser Arg Met Leu Gly Ala Asn
830                 835                 840                 845
```

| | | |
|---|---|---|
| gtc att gcc acc agt ggc cgc gct gtt gaa gcc gct ggc gac gtg gat<br>Val Ile Ala Thr Ser Gly Arg Ala Val Glu Ala Ala Gly Asp Val Asp<br>850          855          860 | | 3130 |
| gtg ctg atg ctg gat aaa acc ggc acc atc acg ctg ggt aac cgt cag<br>Val Leu Met Leu Asp Lys Thr Gly Thr Ile Thr Leu Gly Asn Arg Gln<br>865          870          875 | | 3178 |
| gca acg cag ttt tta ccg gct ccc ggc gtc acg gaa gaa cag ctg gcg<br>Ala Thr Gln Phe Leu Pro Ala Pro Gly Val Thr Glu Glu Gln Leu Ala<br>880          885          890 | | 3226 |
| gat gcg gcg cag ctg gcg tcc ctg gcg gat gaa acg ccg gaa ggg cgc<br>Asp Ala Ala Gln Leu Ala Ser Leu Ala Asp Glu Thr Pro Glu Gly Arg<br>895          900          905 | | 3274 |
| agc atc gtg gtg ctg gcg aag caa aag ttt aac ctg cgt gaa cgt gac<br>Ser Ile Val Val Leu Ala Lys Gln Lys Phe Asn Leu Arg Glu Arg Asp<br>910          915          920          925 | | 3322 |
| ctg agc agc atg ggc gcc agc ttt att ccc ttc tcg gct caa acc cgt<br>Leu Ser Ser Met Gly Ala Ser Phe Ile Pro Phe Ser Ala Gln Thr Arg<br>930          935          940 | | 3370 |
| atg agc ggc gtc aac gta cag gac cgc ctg atc cgt aaa ggt gcg gtc<br>Met Ser Gly Val Asn Val Gln Asp Arg Leu Ile Arg Lys Gly Ala Val<br>945          950          955 | | 3418 |
| gat gcg gtg cgc cgt cat att gaa gcc agc cac ggt gcc ttt ccg gct<br>Asp Ala Val Arg Arg His Ile Glu Ala Ser His Gly Ala Phe Pro Ala<br>960          965          970 | | 3466 |
| gag gtg aac gcc cgg gtt gaa gag gtg gcg cgg gcc ggt ggc aca ccg<br>Glu Val Asn Ala Arg Val Glu Glu Val Ala Arg Ala Gly Gly Thr Pro<br>975          980          985 | | 3514 |
| ctg gtg gtg gcg gaa ggc gca aag gtg ctg ggc gtg gtg gcg cta aaa<br>Leu Val Val Ala Glu Gly Ala Lys Val Leu Gly Val Val Ala Leu Lys<br>990          995          1000          1005 | | 3562 |
| gat atc gtt aaa ggt ggc atc aaa gaa cgt ttt gcg gaa ctg cgc<br>Asp Ile Val Lys Gly Gly Ile Lys Glu Arg Phe Ala Glu Leu Arg<br>1010          1015          1020 | | 3607 |
| aag atg ggc att aaa acc gtg atg atc acc ggt gat aac ccg ctc<br>Lys Met Gly Ile Lys Thr Val Met Ile Thr Gly Asp Asn Pro Leu<br>1025          1030          1035 | | 3652 |
| acc gcc gcc gcc atc gcg gca gag gca ggg gtg gat gac ttt ctg<br>Thr Ala Ala Ala Ile Ala Ala Glu Ala Gly Val Asp Asp Phe Leu<br>1040          1045          1050 | | 3697 |
| tca gaa gcg acg ccg gaa gcc aag ctg gca ctg att cgt cag tat<br>Ser Glu Ala Thr Pro Glu Ala Lys Leu Ala Leu Ile Arg Gln Tyr<br>1055          1060          1065 | | 3742 |
| cag gcg gag ggg cgc tta gtc gcg atg acc ggt gac ggc acc aat<br>Gln Ala Glu Gly Arg Leu Val Ala Met Thr Gly Asp Gly Thr Asn<br>1070          1075          1080 | | 3787 |
| gac gcg cca gcg ttg gcc cag gcg gac gtg gcg gtc gcc atg aac<br>Asp Ala Pro Ala Leu Ala Gln Ala Asp Val Ala Val Ala Met Asn<br>1085          1090          1095 | | 3832 |
| tcg ggt act cag gcg gcg aaa gaa gcg ggc aac atg gtc gat ctg<br>Ser Gly Thr Gln Ala Ala Lys Glu Ala Gly Asn Met Val Asp Leu<br>1100          1105          1110 | | 3877 |
| gac tcg aac ccc acc aaa ctg ctg gaa gtg gtg cac att ggt aag<br>Asp Ser Asn Pro Thr Lys Leu Leu Glu Val Val His Ile Gly Lys<br>1115          1120          1125 | | 3922 |
| cag atg ctg atg acg cgc ggt tcc ttg acc acc ttc agt atc gcc<br>Gln Met Leu Met Thr Arg Gly Ser Leu Thr Thr Phe Ser Ile Ala<br>1130          1135          1140 | | 3967 |
| aat gac gtt gcc aag tat ttc gcc atc atc ccg gcc gcc ttt gct<br>Asn Asp Val Ala Lys Tyr Phe Ala Ile Ile Pro Ala Ala Phe Ala<br>1145          1150          1155 | | 4012 |

| | |
|---|---|
| gca acc tat cca cag tta aat atg ctc aac gtg atg cag ctg cac<br>Ala Thr Tyr Pro Gln Leu Asn Met Leu Asn Val Met Gln Leu His<br>            1160                       1165                       1170 | 4057 |
| tcg ccc gca tcg gcc atc ctg tcg gcc gtg att ttt aac gcc cta<br>Ser Pro Ala Ser Ala Ile Leu Ser Ala Val Ile Phe Asn Ala Leu<br>            1175                       1180                       1185 | 4102 |
| gtg att gta ttc ctg atc cct ctg gcg ctt aaa ggt gtc agc tat<br>Val Ile Val Phe Leu Ile Pro Leu Ala Leu Lys Gly Val Ser Tyr<br>            1190                       1195                       1200 | 4147 |
| cgc ccc ttg agt gcc gca tcg ctg ttg cgc cgt aat tta ctg att<br>Arg Pro Leu Ser Ala Ala Ser Leu Leu Arg Arg Asn Leu Leu Ile<br>            1205                       1210                       1215 | 4192 |
| tat ggg tta ggt ggg ctg ctg gtg ccc ttt gtc ggc atc aaa gcg<br>Tyr Gly Leu Gly Gly Leu Leu Val Pro Phe Val Gly Ile Lys Ala<br>            1220                       1225                       1230 | 4237 |
| att gat atg ttg ctc gtg ctg tct ggt atg gcc tga ggagattaaa atg<br>Ile Asp Met Leu Leu Val Leu Ser Gly Met Ala                           Met<br>                 1235                       1240 | 4286 |
| agt cag tta cgt ccg gcg att ttc ctg ctt ttg ctg cta acg gtt<br>Ser Gln Leu Arg Pro Ala Ile Phe Leu Leu Leu Leu Leu Thr Val<br>            1245                       1250                       1255 | 4331 |
| gtg tgc ggc gtc gtt tat cct ttg ctt acc acg gga ctg tcg caa<br>Val Cys Gly Val Val Tyr Pro Leu Leu Thr Thr Gly Leu Ser Gln<br>            1260                       1265                       1270 | 4376 |
| ctg ctg ttt ccc tgg cag gct aac ggg tca gta ttg aat gtc gat<br>Leu Leu Phe Pro Trp Gln Ala Asn Gly Ser Val Leu Asn Val Asp<br>            1275                       1280                       1285 | 4421 |
| ggc gaa gaa cgg gga tca gcg ctg att ggt cag aat ttt agc cag<br>Gly Glu Glu Arg Gly Ser Ala Leu Ile Gly Gln Asn Phe Ser Gln<br>            1290                       1295                       1300 | 4466 |
| ccc ggt tat ttc tgg ggg cgt cct tct gca acc ggt gat aag cct<br>Pro Gly Tyr Phe Trp Gly Arg Pro Ser Ala Thr Gly Asp Lys Pro<br>            1305                       1310                       1315 | 4511 |
| tat aat cct ctg gcc tcc agc ggc agc aac ctg gcg gcc agc aac<br>Tyr Asn Pro Leu Ala Ser Ser Gly Ser Asn Leu Ala Ala Ser Asn<br>            1320                       1325                       1330 | 4556 |
| ccg gcg ctg gat aag gct gta gcc gag cgc gtg gcg gct ttg cgc<br>Pro Ala Leu Asp Lys Ala Val Ala Glu Arg Val Ala Ala Leu Arg<br>            1335                       1340                       1345 | 4601 |
| acg gcg aat ccg cag gct aac ggg gcg gta ccg gtc gag ctg gta<br>Thr Ala Asn Pro Gln Ala Asn Gly Ala Val Pro Val Glu Leu Val<br>            1350                       1355                       1360 | 4646 |
| acc acc tcg gcc agt gga ctg gac ccg gag att tcg cct gag gct<br>Thr Thr Ser Ala Ser Gly Leu Asp Pro Glu Ile Ser Pro Glu Ala<br>            1365                       1370                       1375 | 4691 |
| gcg ctg tgg cag gca ccg cgt atc gcg gcg gca cgt cag ctg ccg<br>Ala Leu Trp Gln Ala Pro Arg Ile Ala Ala Ala Arg Gln Leu Pro<br>            1380                       1385                       1390 | 4736 |
| ctg gcg aaa gtg gat gcc ctg gta gac agc atg acg cag cgc ccg<br>Leu Ala Lys Val Asp Ala Leu Val Asp Ser Met Thr Gln Arg Pro<br>            1395                       1400                       1405 | 4781 |
| ctg ctg ccc ttt atc ggc gaa ccg act gtc aat gtg ctg cag ctt<br>Leu Leu Pro Phe Ile Gly Glu Pro Thr Val Asn Val Leu Gln Leu<br>            1410                       1415                       1420 | 4826 |
| aat ctg gcg ctg aac gac ctc aaa taa ctgtaaggat gct atg aac cac<br>Asn Leu Ala Leu Asn Asp Leu Lys                           Met Asn His<br>            1425                       1430 | 4875 |
| gaa ccg ctg cgc ccc gat ccg gat gcg ctg ctg cag acc agc agc<br>Glu Pro Leu Arg Pro Asp Pro Asp Ala Leu Leu Gln Thr Ser Ser<br>            1435                       1440                       1445 | 4920 |

```
gac agc cat cgc ggc aaa ctg aaa atc tat ttt ggc gcc tgt gcg    4965
Asp Ser His Arg Gly Lys Leu Lys Ile Tyr Phe Gly Ala Cys Ala
    1450            1455                1460 ggc gta gga aaa acc tat gcc atg ttg cag gag gcg cag cgg ctg    5010
Gly Val Gly Lys Thr Tyr Ala Met Leu Gln Glu Ala Gln Arg Leu
1465                1470                1475 cgt gcc cag ggg ctg gat gtg ctg gtg ggc gta gtg gaa acg cac    5055
Arg Ala Gln Gly Leu Asp Val Leu Val Gly Val Val Glu Thr His
        1480                1485                1490 gaa cgt ccg gaa aca gcg cag ctt ctt aac gga ctg gtg ctg ttg    5100
Glu Arg Pro Glu Thr Ala Gln Leu Leu Asn Gly Leu Val Leu Leu
    1495                1500                1505 ccg cgc cgg gcg acg ggc cgt tcg cgg cat gcg gag ttc gac ctt    5145
Pro Arg Arg Ala Thr Gly Arg Ser Arg His Ala Glu Phe Asp Leu
1510                1515                1520 gat gcc gcg ctg gcg cgc cat ccg gca gta att ttg atg gat gag    5190
Asp Ala Ala Leu Ala Arg His Pro Ala Val Ile Leu Met Asp Glu
        1525                1530                1535 ctg gcg cac acg aac gtg aag ggc tca cgt cat ccc aaa cgc tgg    5235
Leu Ala His Thr Asn Val Lys Gly Ser Arg His Pro Lys Arg Trp
    1540                1545                1550 cag gat att gag gaa ctg ctg gag gcg ggc att gat gtc ctg acg    5280
Gln Asp Ile Glu Glu Leu Leu Glu Ala Gly Ile Asp Val Leu Thr
1555                1560                1565 aca gtg aat gtt cag cat ctg gaa agt ctg aat gat gtg gtc ggt    5325
Thr Val Asn Val Gln His Leu Glu Ser Leu Asn Asp Val Val Gly
        1570                1575                1580 ggc gtc acc ggc att cag gtg cgt gaa acc gtt ccc gat ccc ttt    5370
Gly Val Thr Gly Ile Gln Val Arg Glu Thr Val Pro Asp Pro Phe
    1585                1590                1595 ttc gac gct gcc gat gaa gtg gta ctg gtt gat ctc ccg cct gac    5415
Phe Asp Ala Ala Asp Glu Val Val Leu Val Asp Leu Pro Pro Asp
1600                1605                1610 gat ctc cgc cag cgc ctg aaa gag ggc aag gtc tac att ggc gat    5460
Asp Leu Arg Gln Arg Leu Lys Glu Gly Lys Val Tyr Ile Gly Asp
        1615                1620                1625 cgt gcc gaa cgc gcc atc gaa aat ttc ttt cgt aag ggc aac ctg    5505
Arg Ala Glu Arg Ala Ile Glu Asn Phe Phe Arg Lys Gly Asn Leu
    1630                1635                1640 tat gcc ctg cgt gag ctg gcg ctg cgc cgc act gcc gac cgg gtc    5550
Tyr Ala Leu Arg Glu Leu Ala Leu Arg Arg Thr Ala Asp Arg Val
1645                1650                1655 gat gac cag atg cgc gcc tgg cgc gac agt caa ggc cgc gat cgg    5595
Asp Asp Gln Met Arg Ala Trp Arg Asp Ser Gln Gly Arg Asp Arg
        1660                1665                1670 gtc tgg cac acg cgt gat gcc att tta ttg tgt att ggg gac gat    5640
Val Trp His Thr Arg Asp Ala Ile Leu Leu Cys Ile Gly Asp Asp
    1675                1680                1685 acc ggc agt gaa aaa ctg gtg cgg acg gcg gcg cgg ctg gcc gcc    5685
Thr Gly Ser Glu Lys Leu Val Arg Thr Ala Ala Arg Leu Ala Ala
1690                1695                1700 agg ctg ggc agc gaa tgg cat gcc gtt tac gtg gaa acg ccc cgg    5730
Arg Leu Gly Ser Glu Trp His Ala Val Tyr Val Glu Thr Pro Arg
        1705                1710                1715 ctt aac cgg cta ccg gaa gcg cgg cgt cgg gcc att tta cgc acg    5775
Leu Asn Arg Leu Pro Glu Ala Arg Arg Arg Ala Ile Leu Arg Thr
    1720                1725                1730 ctg aag ctg gcg cag gat atg ggg gcg gag acg gcg acg ctg tcc    5820
Leu Lys Leu Ala Gln Asp Met Gly Ala Glu Thr Ala Thr Leu Ser
1735                1740                1745
```

```
gac cct gat gag gcg cag gcg gtc ctg cgt tac gcg cgg gaa cat      5865
Asp Pro Asp Glu Ala Gln Ala Val Leu Arg Tyr Ala Arg Glu His
    1750            1755                1760 aat ctg ggt aag att gtg aca ggc cga cgc ccg gcg cgc cgc tgg      5910
Asn Leu Gly Lys Ile Val Thr Gly Arg Arg Pro Ala Arg Arg Trp
1765                1770                1775 cgg cgt gac agc ttt gcc gag cgg ctg ggg cag ttg ggt ccc gat      5955
Arg Arg Asp Ser Phe Ala Glu Arg Leu Gly Gln Leu Gly Pro Asp
        1780                1785                1790 ctg gat ctg ttg gtc gtg gcg ctc aat gag cct atc cag gat gcg      6000
Leu Asp Leu Leu Val Val Ala Leu Asn Glu Pro Ile Gln Asp Ala
    1795                1800                1805 ccc cat ccg tta gcc gag gat cgg gtt aac agc gac aaa tgg cgg      6045
Pro His Pro Leu Ala Glu Asp Arg Val Asn Ser Asp Lys Trp Arg
1810                1815                1820 ctg cag ctg cgc ggc gtc ctg atg gcg ctg gtg ctg tgt att gtg      6090
Leu Gln Leu Arg Gly Val Leu Met Ala Leu Val Leu Cys Ile Val
        1825                1830                1835 gtc acc gcc gca ggg cag tcg gtg ctg atc agc ttc gat ccg gcc      6135
Val Thr Ala Ala Gly Gln Ser Val Leu Ile Ser Phe Asp Pro Ala
    1840                1845                1850 aac tgt gtg atg atc tat tta ctg gcg gtg gtg atc gtc gcg ttg      6180
Asn Cys Val Met Ile Tyr Leu Leu Ala Val Val Ile Val Ala Leu
1855                1860                1865 cgc tat gga cga tgg ccc tcc gtt atc gcc acc gtc atg aac atc      6225
Arg Tyr Gly Arg Trp Pro Ser Val Ile Ala Thr Val Met Asn Ile
        1870                1875                1880 att gcc ttt gac ctg ttt ttc gtc gca cct acc ggc acg gtc gcg      6270
Ile Ala Phe Asp Leu Phe Phe Val Ala Pro Thr Gly Thr Val Ala
    1885                1890                1895 gtc tcg gat ttg caa tac ctg gtg acc ttt ggg gtg atg ctg gcg      6315
Val Ser Asp Leu Gln Tyr Leu Val Thr Phe Gly Val Met Leu Ala
1900                1905                1910 gtc ggg gtc att gtt ggc aac ctg acg gcc ggc gtt cgc tac cag      6360
Val Gly Val Ile Val Gly Asn Leu Thr Ala Gly Val Arg Tyr Gln
        1915                1920                1925 gcg cgg gtt gcc cgc tac cgg gag cag cgc acg cgg cag ctt tac      6405
Ala Arg Val Ala Arg Tyr Arg Glu Gln Arg Thr Arg Gln Leu Tyr
    1930                1935                1940 gaa atg gcc aag tcg ctg gga agc ggc ctg acg cct gaa gat atc      6450
Glu Met Ala Lys Ser Leu Gly Ser Gly Leu Thr Pro Glu Asp Ile
1945                1950                1955 gcc gcg acc agc cag cgg gtg ttg gag gcg acc tta cag gcg cga      6495
Ala Ala Thr Ser Gln Arg Val Leu Glu Ala Thr Leu Gln Ala Arg
        1960                1965                1970 tgc ctg ctg ctg cta ccc gat gag cag ggc gaa ctg cac acg ctg      6540
Cys Leu Leu Leu Leu Pro Asp Glu Gln Gly Glu Leu His Thr Leu
    1975                1980                1985 ggc aac gcg ctg ccg ggc aac gaa ccg gat tgg gct atc gcg aaa      6585
Gly Asn Ala Leu Pro Gly Asn Glu Pro Asp Trp Ala Ile Ala Lys
1990                1995                2000 tgg agc ttc agc aag ggc cag cca gca ggc gca ggc acg gac acc      6630
Trp Ser Phe Ser Lys Gly Gln Pro Ala Gly Ala Gly Thr Asp Thr
        2005                2010                2015 tta ccg gcg gtg ccc tat cag att ctg ccg ctg aaa gtg ggc gat      6675
Leu Pro Ala Val Pro Tyr Gln Ile Leu Pro Leu Lys Val Gly Asp
    2020                2025                2030 ctg tgt cgc gga ttg ctg gtg gtt gaa ccg cag aat gtg cgt cag      6720
Leu Cys Arg Gly Leu Leu Val Val Glu Pro Gln Asn Val Arg Gln
2035                2040                2045
```

```
ctg atg gtg ccg gaa cag caa cgg ctg ctg gaa acc ttc acc gtg      6765
Leu Met Val Pro Glu Gln Gln Arg Leu Leu Glu Thr Phe Thr Val
    2050            2055                2060 ctg att gcc aat gcc ctg gag cgg atg gcg ctg tcc cag agt gag      6810
Leu Ile Ala Asn Ala Leu Glu Arg Met Ala Leu Ser Gln Ser Glu
    2065            2070                2075 gcg gct tcc cgg ctg tca gct gaa cgt gag cag ctg cgt aat gct      6855
Ala Ala Ser Arg Leu Ser Ala Glu Arg Glu Gln Leu Arg Asn Ala
    2080            2085                2090 ttg ctg tcg gcg ctc tcc cat gat tta cgt acc ccg ctg acg gtg      6900
Leu Leu Ser Ala Leu Ser His Asp Leu Arg Thr Pro Leu Thr Val
    2095            2100                2105 ctg ttt ggt cag gca gaa atg ctg atg ctg gac ctg gcc agc gat      6945
Leu Phe Gly Gln Ala Glu Met Leu Met Leu Asp Leu Ala Ser Asp
    2110            2115                2120 aac tca aag tat gtg ccc cag gcc agc cag att cgt gaa caa acc      6990
Asn Ser Lys Tyr Val Pro Gln Ala Ser Gln Ile Arg Glu Gln Thr
    2125            2130                2135 ctg agt acc att cgt ctg gtc agc aac atg ctg gat atg gcg cgt      7035
Leu Ser Thr Ile Arg Leu Val Ser Asn Met Leu Asp Met Ala Arg
    2140            2145                2150 att cag tca ggc ggc ctg aat tta cgc gaa gag tgg ctg gcg ctg      7080
Ile Gln Ser Gly Gly Leu Asn Leu Arg Glu Glu Trp Leu Ala Leu
    2155            2160                2165 gaa gag gtg att ggt ggc gcg ctc agt agc atg gcg ccg tcg ctc      7125
Glu Glu Val Ile Gly Gly Ala Leu Ser Ser Met Ala Pro Ser Leu
    2170            2175                2180 aag gga aga gag gtc gaa ctc gat ctg cct gaa gat att gtc ctg      7170
Lys Gly Arg Glu Val Glu Leu Asp Leu Pro Glu Asp Ile Val Leu
    2185            2190                2195 atc aaa ggc gac agt acg ttg ctg gag cgg gta ttt acc aac ctg      7215
Ile Lys Gly Asp Ser Thr Leu Leu Glu Arg Val Phe Thr Asn Leu
    2200            2205                2210 att gaa aac agc ctg aag tac gct ggc aac tgt gcg ccc cgc ggc      7260
Ile Glu Asn Ser Leu Lys Tyr Ala Gly Asn Cys Ala Pro Arg Gly
    2215            2220                2225 ata cgt gcc tgg tgt gaa aat acc cgg ctg gaa atc gcc atc tgg      7305
Ile Arg Ala Trp Cys Glu Asn Thr Arg Leu Glu Ile Ala Ile Trp
    2230            2235                2240 gac ggc ggg ccg ggc atc gcc caa aac gac ctg acg cgg att ttc      7350
Asp Gly Gly Pro Gly Ile Ala Gln Asn Asp Leu Thr Arg Ile Phe
    2245            2250                2255 gac aaa ttt tca cgc ggt gat aaa gaa tcg gcc gta ccg ggc gtt      7395
Asp Lys Phe Ser Arg Gly Asp Lys Glu Ser Ala Val Pro Gly Val
    2260            2265                2270 ggg ctg gga ctg gcg att tgt aaa acg att atc gaa agc cac ggc      7440
Gly Leu Gly Leu Ala Ile Cys Lys Thr Ile Ile Glu Ser His Gly
    2275            2280                2285 ggt cag atc tgg gcg gaa aat cgt gct gaa ggc ggt gcc tgc ttt      7485
Gly Gln Ile Trp Ala Glu Asn Arg Ala Glu Gly Gly Ala Cys Phe
    2290            2295                2300 cgt ctc tct tta cca ctt cca ccc gtt cct gaa att tct cct gaa      7530
Arg Leu Ser Leu Pro Leu Pro Pro Val Pro Glu Ile Ser Pro Glu
    2305            2310                2315 ggc ttg aaa taa cttcacagat gatcggttat aatgcgcgac cttactgatt     7582
Gly Leu Lys
    2320 atgattggga aattatggaa cgttttaccg aaaacctg                       7620
```

```
<210> SEQ ID NO 8
<211> LENGTH: 560
<212> TYPE: PRT
<213> ORGANISM: Pantoea

<400> SEQUENCE: 8

Met Ala Asn Ala Phe Leu Leu Ile Ala Val Tyr Leu Leu Leu
1               5                   10                  15

Met Val Met Ala Gln Pro Leu Gly Arg Gly Leu Ala Ala Leu Val Ala
        20                  25                  30

Asp Lys Pro Leu Phe Ala Arg Ala Glu Ala Leu Leu Trp Arg Phe Ser
            35                  40                  45

Gly Val Gln Glu Gly Gly Met Arg Trp Gln His Tyr Leu Leu Ala Ile
    50                  55                  60

Leu Val Phe Asn Leu Leu Gly Phe Val Val Leu Ala Ile Leu Met
65                  70                  75                  80

Phe Gln Gly Ala Leu Pro Leu Asn Pro Gln His Leu Pro Gly Leu Ser
                85                  90                  95

Trp Asp Leu Ala Leu Asn Thr Ala Ile Ser Phe Val Thr Asn Thr Asn
            100                 105                 110

Trp Gln Ser Tyr Ala Gly Glu Ser Thr Leu Ser Tyr Phe Ser Gln Met
        115                 120                 125

Val Gly Leu Thr Val Gln Asn Phe Val Ser Ala Ala Thr Gly Ile Ala
    130                 135                 140

Val Ala Phe Ala Leu Ile Arg Gly Phe Ala Asn Arg Ser Val Ala Thr
145                 150                 155                 160

Leu Gly Asn Ala Trp Arg Asp Leu Thr Arg Ile Thr Leu Tyr Val Leu
                165                 170                 175

Leu Pro Ile Ser Leu Leu Met Ala Leu Phe Phe Val Ser Gln Gly Ser
            180                 185                 190

Ile Gln Asn Phe Leu Pro Tyr His Asn Val Thr Ser Leu Glu Gly Ala
        195                 200                 205

Gln Gln Thr Leu Ala Met Gly Pro Val Ala Ser Gln Glu Ala Ile Lys
    210                 215                 220

Met Leu Gly Thr Asn Gly Gly Phe Phe Asn Val Asn Ser Ala His
225                 230                 235                 240

Pro Phe Glu Asn Pro Thr Ala Leu Ser Asn Phe Val Gln Met Leu Ser
                245                 250                 255

Ile Phe Leu Ile Pro Ala Ala Leu Cys Phe Ala Phe Gly Glu Ser Val
            260                 265                 270

Lys Asp Arg Arg Gln Gly Ser Met Leu Leu Trp Ser Met Thr Leu Met
        275                 280                 285

Phe Val Val Ala Ala Leu Val Met Trp Ala Glu Leu Arg Gly Asn
    290                 295                 300

Pro His Phe Leu Thr Leu Gly Ala Asp Ser Ala Ile Asn Met Glu Gly
305                 310                 315                 320

Lys Glu Thr Arg Phe Gly Ile Leu Asn Ser Ser Leu Phe Ala Val Ile
                325                 330                 335

Thr Thr Ala Ala Ser Cys Gly Ala Val Asn Ala Met His Asp Ser Phe
            340                 345                 350

Thr Ala Leu Gly Gly Met Val Pro Met Leu Leu Met Gln Leu Gly Glu
        355                 360                 365

Val Val Phe Gly Gly Val Gly Ala Gly Leu Tyr Gly Met Leu Leu Phe
    370                 375                 380

Val Leu Leu Ala Val Phe Ile Ala Gly Leu Met Ile Gly Arg Thr Pro
```

```
                385                 390                 395                 400

Glu Phe Leu Gly Lys Lys Ile Asp Val Trp Glu Met Lys Met Thr Ala
                405                 410                 415

Leu Ala Ile Leu Val Thr Pro Ala Leu Val Leu Ile Gly Thr Ala Ile
                420                 425                 430

Ala Met Met Thr Asp Ala Gly Arg Ala Gly Met Ala Asn Pro Gly Thr
                435                 440                 445

His Gly Phe Ser Glu Val Leu Tyr Ala Val Ser Ala Ala Asn Asn
                450                 455                 460

Asn Gly Ser Ala Phe Ala Gly Leu Asn Ala Asn Thr Pro Phe Trp Asn
465                 470                 475                 480

Leu Leu Leu Ala Val Cys Met Phe Val Gly Arg Phe Gly Ile Ile Ile
                485                 490                 495

Pro Val Met Ala Ile Ala Gly Ala Met Ala Val Lys Lys Val Gln Pro
                500                 505                 510

Val Gly Asn Gly Thr Leu Pro Thr His Gly Pro Leu Phe Ile Ala Leu
                515                 520                 525

Leu Val Gly Thr Val Leu Leu Val Gly Ala Leu Thr Phe Ile Pro Ala
                530                 535                 540

Leu Ala Leu Gly Pro Val Ala Glu His Leu Gln Leu Ile Gln Gly Gln
545                 550                 555                 560

<210> SEQ ID NO 9
<211> LENGTH: 681
<212> TYPE: PRT
<213> ORGANISM: Pantoea

<400> SEQUENCE: 9

Met Ser Arg Gln Gln Gln Val Phe Asp Ala Ala Leu Leu Arg Thr Ser
1               5                   10                  15

Ala Ile Asp Ala Val Lys Lys Leu Asp Pro Arg Val Gln Phe Arg Asn
                20                  25                  30

Pro Val Met Phe Val Val Tyr Leu Gly Ser Ile Leu Thr Ser Ile Leu
                35                  40                  45

Ala Ile Met Met Phe Thr Gly His Gln Ser Gly Ser Ala Ser Phe Thr
        50                  55                  60

Gly Ala Ile Ala Leu Trp Leu Trp Phe Thr Val Leu Phe Ala Asn Met
65              70                  75                  80

Ala Glu Ala Leu Ala Glu Gly Arg Ser Lys Ala Gln Ala Asn Ser Leu
                85                  90                  95

Lys Gly Val Lys Lys Thr Ser Phe Ala Lys Lys Leu Ser Ala Ala His
                100                 105                 110

Tyr Gly Ala Ala Trp Gln Gln Val Ala Ala Asp Ala Leu Arg Lys Gly
                115                 120                 125

Asp Ala Val Leu Val Glu Ala Gly Asp Val Ile Pro Cys Asp Gly Glu
        130                 135                 140

Val Val Glu Gly Gly Ala Ser Val Asp Glu Ser Ala Ile Thr Gly Glu
145                 150                 155                 160

Ser Ala Pro Val Ile Arg Glu Ser Gly Gly Asp Phe Ala Ser Val Thr
                165                 170                 175

Gly Gly Thr Arg Ile Leu Ser Asp Trp Leu Val Ile Thr Cys Ser Ala
                180                 185                 190

Asn Pro Gly Glu Thr Phe Leu Asp Arg Met Ile Ala Met Val Glu Gly
                195                 200                 205

Ala Gln Arg Arg Lys Thr Pro Asn Glu Ile Ala Leu Thr Ile Leu Leu
```

-continued

```
            210                 215                 220
Val Ser Leu Thr Ile Val Phe Leu Leu Ala Thr Val Thr Leu Trp Pro
225                 230                 235                 240

Phe Ser Ala Trp Gly Gly Thr Pro Val Thr Ile Thr Val Leu Val Ala
                245                 250                 255

Leu Leu Val Cys Leu Ile Pro Thr Thr Ile Gly Gly Leu Leu Ser Ala
                260                 265                 270

Ile Gly Val Ala Gly Met Ser Arg Met Leu Gly Ala Asn Val Ile Ala
                275                 280                 285

Thr Ser Gly Arg Ala Val Glu Ala Ala Gly Asp Val Asp Val Leu Met
                290                 295                 300

Leu Asp Lys Thr Gly Thr Ile Thr Leu Gly Asn Arg Gln Ala Thr Gln
305                 310                 315                 320

Phe Leu Pro Ala Pro Gly Val Thr Glu Glu Gln Leu Ala Asp Ala Ala
                325                 330                 335

Gln Leu Ala Ser Leu Ala Asp Glu Thr Pro Glu Gly Arg Ser Ile Val
                340                 345                 350

Val Leu Ala Lys Gln Lys Phe Asn Leu Arg Glu Arg Asp Leu Ser Ser
                355                 360                 365

Met Gly Ala Ser Phe Ile Pro Phe Ser Ala Gln Thr Arg Met Ser Gly
370                 375                 380

Val Asn Val Gln Asp Arg Leu Ile Arg Lys Gly Ala Val Asp Ala Val
385                 390                 395                 400

Arg Arg His Ile Glu Ala Ser His Gly Ala Phe Pro Ala Glu Val Asn
                405                 410                 415

Ala Arg Val Glu Glu Val Ala Arg Ala Gly Gly Thr Pro Leu Val Val
                420                 425                 430

Ala Glu Gly Ala Lys Val Leu Gly Val Val Ala Leu Lys Asp Ile Val
                435                 440                 445

Lys Gly Gly Ile Lys Glu Arg Phe Ala Glu Leu Arg Lys Met Gly Ile
                450                 455                 460

Lys Thr Val Met Ile Thr Gly Asp Asn Pro Leu Thr Ala Ala Ala Ile
465                 470                 475                 480

Ala Ala Glu Ala Gly Val Asp Asp Phe Leu Ser Glu Ala Thr Pro Glu
                485                 490                 495

Ala Lys Leu Ala Leu Ile Arg Gln Tyr Gln Ala Glu Gly Arg Leu Val
                500                 505                 510

Ala Met Thr Gly Asp Gly Thr Asn Asp Ala Pro Ala Leu Ala Gln Ala
                515                 520                 525

Asp Val Ala Val Ala Met Asn Ser Gly Thr Gln Ala Ala Lys Glu Ala
530                 535                 540

Gly Asn Met Val Asp Leu Asp Ser Asn Pro Thr Lys Leu Leu Glu Val
545                 550                 555                 560

Val His Ile Gly Lys Gln Met Leu Met Thr Arg Gly Ser Leu Thr Thr
                565                 570                 575

Phe Ser Ile Ala Asn Asp Val Ala Lys Tyr Phe Ala Ile Ile Pro Ala
                580                 585                 590

Ala Phe Ala Ala Thr Tyr Pro Gln Leu Asn Met Leu Asn Val Met Gln
                595                 600                 605

Leu His Ser Pro Ala Ser Ala Ile Leu Ser Ala Val Ile Phe Asn Ala
                610                 615                 620

Leu Val Ile Val Phe Leu Ile Pro Leu Ala Leu Lys Gly Val Ser Tyr
625                 630                 635                 640
```

```
Arg Pro Leu Ser Ala Ala Ser Leu Leu Arg Arg Asn Leu Leu Ile Tyr
            645                 650                 655

Gly Leu Gly Gly Leu Leu Val Pro Phe Val Gly Ile Lys Ala Ile Asp
            660                 665                 670

Met Leu Leu Val Leu Ser Gly Met Ala
            675                 680

<210> SEQ ID NO 10
<211> LENGTH: 189
<212> TYPE: PRT
<213> ORGANISM: Pantoea

<400> SEQUENCE: 10

Met Ser Gln Leu Arg Pro Ala Ile Phe Leu Leu Leu Leu Thr Val
1               5                   10                  15

Val Cys Gly Val Val Tyr Pro Leu Leu Thr Thr Gly Leu Ser Gln Leu
                20                  25                  30

Leu Phe Pro Trp Gln Ala Asn Gly Ser Val Leu Asn Val Asp Gly Glu
            35                  40                  45

Glu Arg Gly Ser Ala Leu Ile Gly Gln Asn Phe Ser Gln Pro Gly Tyr
        50                  55                  60

Phe Trp Gly Arg Pro Ser Ala Thr Gly Asp Lys Pro Tyr Asn Pro Leu
65                  70                  75                  80

Ala Ser Ser Gly Ser Asn Leu Ala Ala Ser Asn Pro Ala Leu Asp Lys
                85                  90                  95

Ala Val Ala Glu Arg Val Ala Leu Arg Thr Ala Asn Pro Gln Ala
            100                 105                 110

Asn Gly Ala Val Pro Val Glu Leu Val Thr Thr Ser Ala Ser Gly Leu
        115                 120                 125

Asp Pro Glu Ile Ser Pro Glu Ala Ala Leu Trp Gln Ala Pro Arg Ile
    130                 135                 140

Ala Ala Ala Arg Gln Leu Pro Leu Ala Lys Val Asp Ala Leu Val Asp
145                 150                 155                 160

Ser Met Thr Gln Arg Pro Leu Leu Pro Phe Ile Gly Glu Pro Thr Val
                165                 170                 175

Asn Val Leu Gln Leu Asn Leu Ala Leu Asn Asp Leu Lys
            180                 185

<210> SEQ ID NO 11
<211> LENGTH: 891
<212> TYPE: PRT
<213> ORGANISM: Pantoea

<400> SEQUENCE: 11

Met Asn His Glu Pro Leu Arg Pro Asp Pro Asp Ala Leu Leu Gln Thr
1               5                   10                  15

Ser Ser Asp Ser His Arg Gly Lys Leu Lys Ile Tyr Phe Gly Ala Cys
                20                  25                  30

Ala Gly Val Gly Lys Thr Tyr Ala Met Leu Gln Glu Ala Gln Arg Leu
            35                  40                  45

Arg Ala Gln Gly Leu Asp Val Leu Val Gly Val Val Glu Thr His Glu
        50                  55                  60

Arg Pro Glu Thr Ala Gln Leu Leu Asn Gly Leu Val Leu Leu Pro Arg
65                  70                  75                  80

Arg Ala Thr Gly Arg Ser Arg His Ala Glu Phe Asp Leu Asp Ala Ala
                85                  90                  95

Leu Ala Arg His Pro Ala Val Ile Leu Met Asp Glu Leu Ala His Thr
```

```
                    100                 105                 110
Asn Val Lys Gly Ser Arg His Pro Lys Arg Trp Gln Asp Ile Glu Glu
            115                 120                 125

Leu Leu Glu Ala Gly Ile Asp Val Leu Thr Thr Val Asn Val Gln His
        130                 135                 140

Leu Glu Ser Leu Asn Asp Val Val Gly Gly Val Thr Gly Ile Gln Val
145                 150                 155                 160

Arg Glu Thr Val Pro Asp Pro Phe Phe Asp Ala Ala Glu Val Val
                165                 170                 175

Leu Val Asp Leu Pro Pro Asp Asp Leu Arg Gln Arg Leu Lys Glu Gly
                180                 185                 190

Lys Val Tyr Ile Gly Asp Arg Ala Glu Arg Ala Ile Glu Asn Phe Phe
            195                 200                 205

Arg Lys Gly Asn Leu Tyr Ala Leu Arg Glu Leu Ala Leu Arg Arg Thr
210                 215                 220

Ala Asp Arg Val Asp Asp Gln Met Arg Ala Trp Arg Asp Ser Gln Gly
225                 230                 235                 240

Arg Asp Arg Val Trp His Thr Arg Asp Ala Ile Leu Leu Cys Ile Gly
                245                 250                 255

Asp Asp Thr Gly Ser Glu Lys Leu Val Arg Thr Ala Ala Arg Leu Ala
                260                 265                 270

Ala Arg Leu Gly Ser Glu Trp His Ala Val Tyr Val Glu Thr Pro Arg
            275                 280                 285

Leu Asn Arg Leu Pro Glu Ala Arg Arg Arg Ala Ile Leu Arg Thr Leu
        290                 295                 300

Lys Leu Ala Gln Asp Met Gly Ala Glu Thr Ala Thr Leu Ser Asp Pro
305                 310                 315                 320

Asp Glu Ala Gln Ala Val Leu Arg Tyr Ala Arg Glu His Asn Leu Gly
                325                 330                 335

Lys Ile Val Thr Gly Arg Arg Pro Ala Arg Arg Trp Arg Arg Asp Ser
            340                 345                 350

Phe Ala Glu Arg Leu Gly Gln Leu Gly Pro Asp Leu Asp Leu Leu Val
                355                 360                 365

Val Ala Leu Asn Glu Pro Ile Gln Asp Ala Pro His Pro Leu Ala Glu
        370                 375                 380

Asp Arg Val Asn Ser Asp Lys Trp Arg Leu Gln Leu Arg Gly Val Leu
385                 390                 395                 400

Met Ala Leu Val Leu Cys Ile Val Val Thr Ala Ala Gly Gln Ser Val
                405                 410                 415

Leu Ile Ser Phe Asp Pro Ala Asn Cys Val Met Ile Tyr Leu Leu Ala
                420                 425                 430

Val Val Ile Val Ala Leu Arg Tyr Gly Arg Trp Pro Ser Val Ile Ala
        435                 440                 445

Thr Val Met Asn Ile Ile Ala Phe Asp Leu Phe Val Ala Pro Thr
        450                 455                 460

Gly Thr Val Ala Val Ser Asp Leu Gln Tyr Leu Val Thr Phe Gly Val
465                 470                 475                 480

Met Leu Ala Val Gly Val Ile Val Gly Asn Leu Thr Ala Gly Val Arg
                485                 490                 495

Tyr Gln Ala Arg Val Ala Arg Tyr Arg Glu Gln Arg Thr Arg Gln Leu
                500                 505                 510

Tyr Glu Met Ala Lys Ser Leu Gly Ser Gly Leu Thr Pro Glu Asp Ile
            515                 520                 525
```

| | | | | | | | | | | | |
|---|---|---|---|---|---|---|---|---|---|---|---|
| Ala | Ala | Thr | Ser | Gln | Arg | Val | Leu | Glu | Ala | Thr | Leu | Gln | Ala | Arg | Cys |

Ala Ala Thr Ser Gln Arg Val Leu Glu Ala Thr Leu Gln Ala Arg Cys
        530                 535                 540

Leu Leu Leu Leu Pro Asp Glu Gln Gly Glu Leu His Thr Leu Gly Asn
545                 550                 555                 560

Ala Leu Pro Gly Asn Glu Pro Asp Trp Ala Ile Ala Lys Trp Ser Phe
                565                 570                 575

Ser Lys Gly Gln Pro Ala Gly Ala Gly Thr Asp Thr Leu Pro Ala Val
            580                 585                 590

Pro Tyr Gln Ile Leu Pro Leu Lys Val Gly Asp Leu Cys Arg Gly Leu
        595                 600                 605

Leu Val Val Glu Pro Gln Asn Val Arg Gln Leu Met Val Pro Glu Gln
        610                 615                 620

Gln Arg Leu Leu Glu Thr Phe Thr Val Leu Ile Ala Asn Ala Leu Glu
625                 630                 635                 640

Arg Met Ala Leu Ser Gln Ser Glu Ala Ala Ser Arg Leu Ser Ala Glu
                645                 650                 655

Arg Glu Gln Leu Arg Asn Ala Leu Leu Ser Ala Leu Ser His Asp Leu
            660                 665                 670

Arg Thr Pro Leu Thr Val Leu Phe Gly Gln Ala Glu Met Leu Met Leu
        675                 680                 685

Asp Leu Ala Ser Asp Asn Ser Lys Tyr Val Pro Gln Ala Ser Gln Ile
        690                 695                 700

Arg Glu Gln Thr Leu Ser Thr Ile Arg Leu Val Ser Asn Met Leu Asp
705                 710                 715                 720

Met Ala Arg Ile Gln Ser Gly Gly Leu Asn Leu Arg Glu Glu Trp Leu
                725                 730                 735

Ala Leu Glu Glu Val Ile Gly Gly Ala Leu Ser Ser Met Ala Pro Ser
            740                 745                 750

Leu Lys Gly Arg Glu Val Glu Leu Asp Leu Pro Glu Asp Ile Val Leu
        755                 760                 765

Ile Lys Gly Asp Ser Thr Leu Leu Glu Arg Val Phe Thr Asn Leu Ile
770                 775                 780

Glu Asn Ser Leu Lys Tyr Ala Gly Asn Cys Ala Pro Arg Gly Ile Arg
785                 790                 795                 800

Ala Trp Cys Glu Asn Thr Arg Leu Glu Ile Ala Ile Trp Asp Gly Gly
                805                 810                 815

Pro Gly Ile Ala Gln Asn Asp Leu Thr Arg Ile Phe Asp Lys Phe Ser
            820                 825                 830

Arg Gly Asp Lys Glu Ser Ala Val Pro Gly Val Gly Leu Gly Leu Ala
        835                 840                 845

Ile Cys Lys Thr Ile Ile Glu Ser His Gly Gly Gln Ile Trp Ala Glu
    850                 855                 860

Asn Arg Ala Glu Gly Gly Ala Cys Phe Arg Leu Ser Leu Pro Leu Pro
865                 870                 875                 880

Pro Val Pro Glu Ile Ser Pro Glu Gly Leu Lys
                885                 890

<210> SEQ ID NO 12
<211> LENGTH: 1215
<212> TYPE: DNA
<213> ORGANISM: Pantoea
<220> FEATURE:
<221> NAME/KEY: CDS
<222> LOCATION: (301)..(975)

<400> SEQUENCE: 12

```
gcgtacggcg caaaatgatt ttatgacgag aataagtccg gtacatggat tcctcctgac      60
gaaaagtcgg ttaaatgtga tctgcatcca atattacgcc tgattgtgta attttactac     120
tcatctgacc actaaatttg acgcttttt gtactgttaa tgacaatctg aaaattagtt     180
acattttggt taaataatgg ttttgacgat gatctttagc gcgattcgat ggcaacacgg     240
acgaaaggct gaaaagttga tacagtgtat tttccctttt caggcaatgg caggattggc     300 gtg acc acg gtt tta atc att gaa gat gag aaa gaa att cgc cgc ttc       348
Val Thr Thr Val Leu Ile Ile Glu Asp Glu Lys Glu Ile Arg Arg Phe
1               5                   10                  15 gtg cgc atc gcg ttg gaa agc gaa ggc ctg aag gtt ttc gat gcc gaa       396
Val Arg Ile Ala Leu Glu Ser Glu Gly Leu Lys Val Phe Asp Ala Glu
            20                  25                  30 acg cta caa cgt ggg ttg att gag gcg gcg acg cga aaa ccc gat ctg       444
Thr Leu Gln Arg Gly Leu Ile Glu Ala Ala Thr Arg Lys Pro Asp Leu
        35                  40                  45 gtc att ctc gat ctc ggc ctg ccc gat ggc gat ggc aaa acc ttt att       492
Val Ile Leu Asp Leu Gly Leu Pro Asp Gly Asp Gly Lys Thr Phe Ile
    50                  55                  60 ggc gag ctg cgt cag tgg agc acg ctg ccc gtg att gtg ctg tcg gcc       540
Gly Glu Leu Arg Gln Trp Ser Thr Leu Pro Val Ile Val Leu Ser Ala
65                  70                  75                  80 cga atc gac gaa cag gat aaa att gac gcg ctg gat gca ggg gcc gac       588
Arg Ile Asp Glu Gln Asp Lys Ile Asp Ala Leu Asp Ala Gly Ala Asp
                85                  90                  95 gat tac ctg acg aaa ccc ttc ggt att ggt gaa ctg ctg gca cgc gtt       636
Asp Tyr Leu Thr Lys Pro Phe Gly Ile Gly Glu Leu Leu Ala Arg Val
            100                 105                 110 cgc gtc gcc ttg cgc cgt cat gcc gga caa cat acc gat ccc aag gtc       684
Arg Val Ala Leu Arg Arg His Ala Gly Gln His Thr Asp Pro Lys Val
        115                 120                 125 agc ttc gcc gac gtt acc gtg gat att gcg gcc cgc aga gtg ctg cgc       732
Ser Phe Ala Asp Val Thr Val Asp Ile Ala Ala Arg Arg Val Leu Arg
    130                 135                 140 gct ggc gag gaa gtg cac ctt acg ccg ata gag ttt cgt ttg ctg acg       780
Ala Gly Glu Glu Val His Leu Thr Pro Ile Glu Phe Arg Leu Leu Thr
145                 150                 155                 160 acg ctg ctg aac aac gcg ggc aaa gtg ctg acc cag cgg cag ctg ttg       828
Thr Leu Leu Asn Asn Ala Gly Lys Val Leu Thr Gln Arg Gln Leu Leu
                165                 170                 175 agc cag gtg tgg gga cca aac gcc gtt gaa cac agc cac tat ctg cgg       876
Ser Gln Val Trp Gly Pro Asn Ala Val Glu His Ser His Tyr Leu Arg
            180                 185                 190 atc tat atg ggg cac ctg cgg caa aag ctg gag gcg aat cct acc cag       924
Ile Tyr Met Gly His Leu Arg Gln Lys Leu Glu Ala Asn Pro Thr Gln
        195                 200                 205 ccg gta cat ctg ctc acg gaa acc ggc atc ggc tac cgg ttt atg cca       972
Pro Val His Leu Leu Thr Glu Thr Gly Ile Gly Tyr Arg Phe Met Pro
    210                 215                 220 taa aaaaagcgcc acttaggcgc ttttttcatt taacaggcaa atcaggcgtt           1025
tttcagcact tcgctgacaa tctctaccgc ttctttttct atctgcgcgc ggtgttctgc   1085
gcccaggaaa ctttcacaat agattttgta tgcatcttcg gtgcctgaag gacgggccgc   1145
aaaccagccg ttttccgtca tcactttcag gccgccgata gacgcgccat tgcccggcgc   1205
agcggtcaga                                                           1215

<210> SEQ ID NO 13
<211> LENGTH: 224
<212> TYPE: PRT
```

<213> ORGANISM: Pantoea

<400> SEQUENCE: 13

```
Val Thr Thr Val Leu Ile Ile Glu Asp Glu Lys Glu Ile Arg Arg Phe
1               5                   10                  15

Val Arg Ile Ala Leu Glu Ser Glu Gly Leu Lys Val Phe Asp Ala Glu
            20                  25                  30

Thr Leu Gln Arg Gly Leu Ile Glu Ala Ala Thr Arg Lys Pro Asp Leu
        35                  40                  45

Val Ile Leu Asp Leu Gly Leu Pro Asp Gly Asp Gly Lys Thr Phe Ile
    50                  55                  60

Gly Glu Leu Arg Gln Trp Ser Thr Leu Pro Val Ile Val Leu Ser Ala
65                  70                  75                  80

Arg Ile Asp Glu Gln Asp Lys Ile Asp Ala Leu Asp Ala Gly Ala Asp
                85                  90                  95

Asp Tyr Leu Thr Lys Pro Phe Gly Ile Gly Glu Leu Leu Ala Arg Val
            100                 105                 110

Arg Val Ala Leu Arg Arg His Ala Gly Gln His Thr Asp Pro Lys Val
        115                 120                 125

Ser Phe Ala Asp Val Thr Val Asp Ile Ala Ala Arg Arg Val Leu Arg
    130                 135                 140

Ala Gly Glu Glu Val His Leu Thr Pro Ile Glu Phe Arg Leu Leu Thr
145                 150                 155                 160

Thr Leu Leu Asn Asn Ala Gly Lys Val Leu Thr Gln Arg Gln Leu Leu
                165                 170                 175

Ser Gln Val Trp Gly Pro Asn Ala Val Glu His Ser His Tyr Leu Arg
            180                 185                 190

Ile Tyr Met Gly His Leu Arg Gln Lys Leu Glu Ala Asn Pro Thr Gln
        195                 200                 205

Pro Val His Leu Leu Thr Glu Thr Gly Ile Gly Tyr Arg Phe Met Pro
    210                 215                 220
```

<210> SEQ ID NO 14
<211> LENGTH: 1308
<212> TYPE: DNA
<213> ORGANISM: Pantoea

<400> SEQUENCE: 14

```
atgagcagaa tcatgacgcc cgtgaactgg gaagcctgca gcagcgaggc gcagcaggcg      60
ctgttggcac gccctgcgct cgcctcgtct gacagcatca gccagatcgt gcgcgatgtg     120
ttggtcagag tgaaagagga aggcgatgcg gctttacgag aattcagcgc gcgctttgac     180
aaggttgaaa cagacgacct cgcgcgttac gccacagcag atgcaggcgg cagcgatcgc     240
cttggtgacg agctgaaaca ggcgatggcc gtggccattg gcaatattga aacctttcac     300
cgtgcgcaga tcctgccgcc ggtggatgtg gaaacgcagc ccggcgtgcg ctgtcagcaa     360
attacgcgcc cgatgaaatc ggtgggcttg tatattccgg gcggttctgc cccgctgttt     420
tctaccgttc tgatgctggc taccccggcg cggattgcgg gctgtggtcg cgtggtgctg     480
tgctcgcccc cgccgattgc tgatgaaatt ctctacgcgg ccaaactttg cggtgtggaa     540
gaagtgttcc aggtgggtgg atcacaggcg attgccgccc tggcttttgg caccgaaagc     600
atccctaagg tagataaaat ttttggtccg ggcaacgcgt gggttaccga agccaaacgt     660
caggtcagcc agcgcttga tggcgcggc attgatatgc ccgctggccc gtcggaagtg     720
ctggtgattg ccgatgaagg tgccacaccg gccttcgttg cctctgatct gctgtcgcag     780
```

```
gcggaacacg gccctgactc gcaggtgatt ttactgacgc cttcgctggc gctggccgag    840
cgcgtcgccg aggcggtgga ggatcagctg gcccagttgc cacgtgcggc gacagcccgc    900
caggcactgg aaagcagccg cctgatcgtc gcccgggata tgcagcaatg cattgcgatc    960
tccaaccgct atggtccgga gcacctgatt ctgcaaaccc gcacgccacg ggatctggtg   1020
gaacagatta ccagcgccgg ttcggttttc ctgggcgact ggtcaccgga atccgcagga   1080
gattatgctt cgggcaccaa ccacgtgctg ccgacctacg gctataccgc gacatgctcc   1140
agcctgggcc tggccgactt tcagaaacgc atgacggtac aggagctgac gccgcagggc   1200
ttcctgaacc tggcggcgac catcgaaacc ctggcggccg ctgaacagct gcacgcccac   1260
aaaaatgccg tcacgttgcg cgttgccgca ctcaaggagc aagcatga              1308
```

```
<210> SEQ ID NO 15
<211> LENGTH: 68
<212> TYPE: DNA
<213> ORGANISM: Artificial
<220> FEATURE:
<223> OTHER INFORMATION: Synthetic

<400> SEQUENCE: 15
ccatagcggt tggagatcgc aatgcattgc tgcatatccc tgaagcctgc ttttttatac     60
taagttgg                                                              68

<210> SEQ ID NO 16
<211> LENGTH: 68
<212> TYPE: DNA
<213> ORGANISM: Artificial
<220> FEATURE:
<223> OTHER INFORMATION: Synthetic

<400> SEQUENCE: 16
gcccgccagg cactggaaag cagccgcctg atcgtcgccc cgctcaagtt agtataaaaa     60
agctgaac                                                              68

<210> SEQ ID NO 17
<211> LENGTH: 33
<212> TYPE: DNA
<213> ORGANISM: Artificial
<220> FEATURE:
<223> OTHER INFORMATION: Synthetic

<400> SEQUENCE: 17
tagcgagatc tctgatgtcc ggcggtgctt ttg                                  33

<210> SEQ ID NO 18
<211> LENGTH: 32
<212> TYPE: DNA
<213> ORGANISM: Artificial
<220> FEATURE:
<223> OTHER INFORMATION: Synthetic

<400> SEQUENCE: 18
aaaaagagct cttacgcccc gccctgccac tc                                   32

<210> SEQ ID NO 19
<211> LENGTH: 34
<212> TYPE: DNA
<213> ORGANISM: Artificial
<220> FEATURE:
<223> OTHER INFORMATION: Synthetic

<400> SEQUENCE: 19
```

```
caggatctag aaggagacat gaacgatgaa catc                                   34
```

<210> SEQ ID NO 20
<211> LENGTH: 36
<212> TYPE: DNA
<213> ORGANISM: Artificial
<220> FEATURE:
<223> OTHER INFORMATION: Synthetic

<400> SEQUENCE: 20

```
gataaggatc cgaaataaaa gaaaatgcca atagga                                 36
```

<210> SEQ ID NO 21
<211> LENGTH: 31
<212> TYPE: DNA
<213> ORGANISM: Artificial
<220> FEATURE:
<223> OTHER INFORMATION: Synthetic

<400> SEQUENCE: 21

```
cctttgagct cgcgggcagt gagcgcaacg c                                      31
```

<210> SEQ ID NO 22
<211> LENGTH: 48
<212> TYPE: DNA
<213> ORGANISM: Artificial
<220> FEATURE:
<223> OTHER INFORMATION: Synthetic

<400> SEQUENCE: 22

```
ctagagcggc cgccgatcgg gatcctcctg tgtgaaattg ttatccgc                    48
```

<210> SEQ ID NO 23
<211> LENGTH: 42
<212> TYPE: DNA
<213> ORGANISM: Artificial
<220> FEATURE:
<223> OTHER INFORMATION: Synthetic

<400> SEQUENCE: 23

```
ctctacgatc gaggaggtta taaaaaatgg atattaatac tg                          42
```

<210> SEQ ID NO 24
<211> LENGTH: 36
<212> TYPE: DNA
<213> ORGANISM: Artificial
<220> FEATURE:
<223> OTHER INFORMATION: Synthetic

<400> SEQUENCE: 24

```
tcaaagcggc cgcttcttcg tctgtttcta ctggta                                 36
```

<210> SEQ ID NO 25
<211> LENGTH: 31
<212> TYPE: DNA
<213> ORGANISM: Artificial
<220> FEATURE:
<223> OTHER INFORMATION: Synthetic

<400> SEQUENCE: 25

```
cctttggtac cgcgggcagt gagcgcaacg c                                      31
```

<210> SEQ ID NO 26
<211> LENGTH: 34
<212> TYPE: DNA
<213> ORGANISM: Artificial
<220> FEATURE:

```
<223> OTHER INFORMATION: Synthetic

<400> SEQUENCE: 26
aacaggaatt ctttgcctgg cggcagtagc gcgg                                   34

<210> SEQ ID NO 27
<211> LENGTH: 40
<212> TYPE: DNA
<213> ORGANISM: Artificial
<220> FEATURE:
<223> OTHER INFORMATION: Synthetic

<400> SEQUENCE: 27
ctagtaagat cttgaagcct gcttttttat actaagttgg                             40

<210> SEQ ID NO 28
<211> LENGTH: 41
<212> TYPE: DNA
<213> ORGANISM: Artificial
<220> FEATURE:
<223> OTHER INFORMATION: Synthetic

<400> SEQUENCE: 28
atgatcgaat tcgaaatcaa ataatgattt tattttgact g                           41

<210> SEQ ID NO 29
<211> LENGTH: 120
<212> TYPE: DNA
<213> ORGANISM: Artificial
<220> FEATURE:
<223> OTHER INFORMATION: DNA fragment containing attL

<400> SEQUENCE: 29
agatcttgaa gcctgctttt ttatactaag ttggcattat aaaaaagcat tgcttatcaa       60
tttgttgcaa cgaacaggtc actatcagtc aaaataaaat cattatttga tttcgaattc      120

<210> SEQ ID NO 30
<211> LENGTH: 41
<212> TYPE: DNA
<213> ORGANISM: Artificial
<220> FEATURE:
<223> OTHER INFORMATION: Synthetic

<400> SEQUENCE: 30
atgccactgc agtctgttac aggtcactaa taccatctaa g                           41

<210> SEQ ID NO 31
<211> LENGTH: 46
<212> TYPE: DNA
<213> ORGANISM: Artificial
<220> FEATURE:
<223> OTHER INFORMATION: Synthetic

<400> SEQUENCE: 31
accgttaagc tttctagacg ctcaagttag tataaaaaag ctgaac                      46

<210> SEQ ID NO 32
<211> LENGTH: 184
<212> TYPE: DNA
<213> ORGANISM: Artificial
<220> FEATURE:
<223> OTHER INFORMATION: DNA fragment containing attR

<400> SEQUENCE: 32
ctgcagtctg ttacaggtca ctaataccat ctaagtagtt gattcatagt gactgcatat       60
```

```
gttgtgtttt acagtattat gtagtctgtt ttttatgcaa atctaatttt aatatattga    120
tatttatatc atttacgtt tctcgttcag ctttttata ctaacttgag cgtctagaaa     180
gctt                                                                 184
```

<210> SEQ ID NO 33
<211> LENGTH: 38
<212> TYPE: DNA
<213> ORGANISM: Artificial
<220> FEATURE:
<223> OTHER INFORMATION: Synthetic

<400> SEQUENCE: 33

```
ttcttagacg tcaggtggca cttttcgggg aaatgtgc                            38
```

<210> SEQ ID NO 34
<211> LENGTH: 37
<212> TYPE: DNA
<213> ORGANISM: Artificial
<220> FEATURE:
<223> OTHER INFORMATION: Synthetic

<400> SEQUENCE: 34

```
taacagagat ctcgcgcaga aaaaaggat ctcaaga                              37
```

<210> SEQ ID NO 35
<211> LENGTH: 46
<212> TYPE: DNA
<213> ORGANISM: Artificial
<220> FEATURE:
<223> OTHER INFORMATION: Synthetic

<400> SEQUENCE: 35

```
aacagagatc taagcttaga tcctttgcct ggcggcagta gcgcgg                   46
```

<210> SEQ ID NO 36
<211> LENGTH: 35
<212> TYPE: DNA
<213> ORGANISM: Artificial
<220> FEATURE:
<223> OTHER INFORMATION: Synthetic

<400> SEQUENCE: 36

```
ataaactgca gcaaaagag tttgtagaaa cgcaa                                35
```

<210> SEQ ID NO 37
<211> LENGTH: 1388
<212> TYPE: DNA
<213> ORGANISM: Artificial
<220> FEATURE:
<223> OTHER INFORMATION: DNA fragment containing Tc gene and ter_thrL

<400> SEQUENCE: 37

```
gaattctcat gtttgacagc ttatcatcga taagctttaa tgcggtagtt tatcacagtt    60
aaattgctaa cgcagtcagg caccgtgtat gaaatctaac aatgcgctca tcgtcatcct   120
cggcaccgtc accctggatg ctgtaggcat aggcttggtt atgccggtac tgccgggcct   180
cttgcgggat atcgtccatt ccgacagcat cgccagtcac tatggcgtgc tgctagcgct   240
atatgcgttg atgcaatttc tatgcgcacc cgttctcgga gcactgtccg accgctttgg   300
ccgccgccca gtcctgctcg cttcgctact tggagccact atcgactacg cgatcatggc   360
gaccacaccc gtcctgtgga tcctctacgc cggacgcatc gtggccggca tcaccggcgc   420
cacaggtgcg gttgctggcg cctatatcgc cgacatcacc gatggggaag atcgggctcg   480
```

```
ccacttcggg ctcatgagcg cttgtttcgg cgtgggtatg gtggcaggcc ccgtggccgg      540
gggactgttg ggcgccatct ccttgcatgc accattcctt gcggcggcgg tgctcaacgg      600
cctcaaccta ctactgggct gcttcctaat gcaggagtcg cataagggag agcgtcgacc      660
gatgcccttg agagcttca acccagtcag ctccttccgg tgggcgcggg gcatgactat       720
cgtcgccgca cttatgactg tcttctttat catgcaactc gtaggacagg tgccggcagc      780
gctctgggtc attttcggcg aggaccgctt tcgctggagc gcgacgatga tcggcctgtc      840
gcttgcggta ttcggaatct tgcacgccct cgctcaagcc ttcgtcactg gtcccgccac      900
caaacgtttc ggcgagaagc aggccattat cgccggcatg gcggccgacg cgctgggcta      960
cgtcttgctg gcgttcgcga cgcgaggctg gatggccttc cccattatga ttcttctcgc     1020
ttccggcggc atcgggatgc ccgcgttgca ggccatgctg tccaggcagg tagatgacga     1080
ccatcaggga cagcttcaag gatcgctcgc ggctcttacc agcctaactt cgatcactgg     1140
accgctgatc gtcacggcga tttatgccgc ctcggcgagc acatggaacg ggttggcatg     1200
gattgtaggc gccgccctat accttgtctg cctccccgcg ttgcgtcgcg gtgcatggag     1260
ccgggccacc tcgacctgaa tggaagccgg cggcacctcg ctaacggatt caccactcca     1320
actagaaagc ttaacacaga aaaaagcccg cacctgacag tgcgggcttt ttttttcgac     1380
cactgcag                                                              1388
```

<210> SEQ ID NO 38
<211> LENGTH: 36
<212> TYPE: DNA
<213> ORGANISM: Artificial
<220> FEATURE:
<223> OTHER INFORMATION: Synthetic

<400> SEQUENCE: 38
agtaattcta gaaagcttaa cacagaaaaa agcccg                                36

<210> SEQ ID NO 39
<211> LENGTH: 43
<212> TYPE: DNA
<213> ORGANISM: Artificial
<220> FEATURE:
<223> OTHER INFORMATION: Synthetic

<400> SEQUENCE: 39
ctagtaggat ccctgcagtg gtcgaaaaaa aaagcccgca ctg                         43

<210> SEQ ID NO 40
<211> LENGTH: 33
<212> TYPE: DNA
<213> ORGANISM: Artificial
<220> FEATURE:
<223> OTHER INFORMATION: Synthetic

<400> SEQUENCE: 40
ggaagatcta tttgccttcg cacatcaacc tgg                                    33

<210> SEQ ID NO 41
<211> LENGTH: 30
<212> TYPE: DNA
<213> ORGANISM: Artificial
<220> FEATURE:
<223> OTHER INFORMATION: Synthetic

<400> SEQUENCE: 41
cggggtacct tgtaaatatt ttaacccgcc                                        30

<210> SEQ ID NO 42
<211> LENGTH: 56
<212> TYPE: DNA
<213> ORGANISM: Artificial
<220> FEATURE:
<223> OTHER INFORMATION: Synthetic

<400> SEQUENCE: 42
ggaagatcta aggagacctt aaatgagcga cacaacgatc ctgcaaaaca gtaccc         56

<210> SEQ ID NO 43
<211> LENGTH: 39
<212> TYPE: DNA
<213> ORGANISM: Artificial
<220> FEATURE:
<223> OTHER INFORMATION: Synthetic

<400> SEQUENCE: 43
cggggtacct cgtagaggtt tactggcgct tatccagcg                             39

<210> SEQ ID NO 44
<211> LENGTH: 864
<212> TYPE: DNA
<213> ORGANISM: Pantoea

<400> SEQUENCE: 44
atgtctgaac aacactatca gcccgctaaa gtctggaagt gggacccgga agcgaaaggt      60
aatggtgcca aaactaaccg ccctaccgct ggcccaaccc atgaaaaagc cctgccggtt     120
ggtaagcatc cgctgcagct ctactctctg gcacgcccta acggcagaa agtcactatt      180 ctgctggaag agttgctggc gctgaacgtg aacgatgcag agtacgatgc ctggttaatc    240
aatattggtg aaggcgacca gttcagcagc ggttttgttg agatcaaccc caactccaaa    300
atcccggcac tgtgcgatca ttcagccaca ccaccgattc gcgtatttga atccggtaac    360
atcctgctct atctggcgga aaaatacggt tatttcctgc cgaaagatcc ggccaaacgc    420
accgaaacgc tgaactggct gttctggctg caaggctcag ccccttacct tggcggcggc    480
tttggtcact tctatcatta cgcgccagaa aagattgaat acgccatcaa ccgcttctca    540
ctggaagcca acgtcagtt tgacgtgctg gaccgtcagc ttgccgataa ccgttatctg    600
gcgggtgacg attacaccat cgccgatatc gccacctggc cgtggtacgg cagcatggtg    660
ctgtataacc agtacaatgc ggcagaattc ctcgaccttc agtcctacaa aaatgtggtg    720
cgctgggccg aagagatcgc tctgcgtccg gccgttatgc gcggccgcaa ggtgaaccgt    780
gtgatgggcg aacccgccga tcagctgcgc gagcgccatg acgcatcgga ctttgatacg    840
caaacccaag acaagcaagc ctga                                           864

<210> SEQ ID NO 45
<211> LENGTH: 918
<212> TYPE: DNA
<213> ORGANISM: Pantoea

<400> SEQUENCE: 45
atgtcagcac gagtctggtg tctgggtgat gccgtggtgg acctgcttcc ggacgggccg      60
gggcatttaa tacagtgtgc aggcggggcg cccgccaatg tggcgtgggg cattgcccgc     120
ttacagggcc gcagcgggtt tattggccgg gttggggacg atccttttgg tcacttatg    180 cagcacacgc tggcgactga acaggttgat acccgctata tgacgctgga cagcgcccag    240
cgcacctcaa cggtggtggt ggcgctggat caggaaggtg agcggacttt tacctttatg    300

| | |
|---|---|
| gtgcgcccca gtgcagatct gttctggaa caaggcgatc tccccaggtt tgagcaaggt | 360 |
| gaatggcttc actgctgctc aattgccctg gcggcagaac cttcgcgctc caccaccttt | 420 |
| tctgccatgc agcagatcag cgatgccggt ggctttgtga gctttgatcc caatattcgt | 480 |
| cacgatctgt ggcacgacga tgcccaactg cgggactgtg tgaaccgggc gttacagctg | 540 |
| gccgatgtgg tcaagctgtc tgaggaagag ctggcttttc tgactccggg ggcgcaacac | 600 |
| gctgacagca tgcaggcgct ggcggaacgc tttgcgatta gcctgctgat ggtcacccag | 660 |
| ggcaaggcag gagtgaaagt ctggcatcag ggtaaacatt atcactatcc cacgctgcct | 720 |
| gtggtgagcg tggacaccac cggcgcaggg gatgcgtttg tcgccgggct gctatggggg | 780 |
| ctggcggaaa aggggatgcc cgctaatgag gccgagctgg cggcacgact cagcagcgca | 840 |
| cagcagtgtg gggcgctggc gacgacggca aaggggcca tgaccgcgtt gccttatcgt | 900 |
| caccaaattg aaggatga | 918 |

<210> SEQ ID NO 46
<211> LENGTH: 3095
<212> TYPE: DNA
<213> ORGANISM: Pantoea

<400> SEQUENCE: 46

| | |
|---|---|
| agactgccat gaccctggac agagattcat tagcggccgt actcgcccgg cgcgactggg | 60 |
| aaaaccccgg cgtcagcgaa cataaccggc tggaagccca tccgccgttt tacagctggc | 120 |
| gcagcgctga gcggccccat aacaacgcgc catcggcgca cgaaaaagc ctgagcggcg | 180 |
| aatggacgtt tgccttttc cctgcgcccg aggcggtgcc ggatagctgg cgcacccagg | 240 |
| atttgcaggc ggcagcgacg attaccgtgc cgtcagtctg gcaaatgcag gctatgatg | 300 |
| ttccgattta caccaatgtt acctatccca ttccggttga tccccgcgc gttccggctg | 360 |
| aaaatcctac gggatgttat tcgctcacat ttaatgtgga tgcagactgg ctgcaacatg | 420 |
| gacaaacccg aattatttt gacggcgtga attcagcctt ctatctctgg tgcaacggac | 480 |
| gctgggtggg ctacgggcag acagccgct tgccgtctga atttgatctg agcgaatttc | 540 |
| tgcgcgaagg tgaaaatcgc ctggcggtga tggtgttgcg ctggagcgat ggcagctatc | 600 |
| tggaagatca ggatatgtgg cgcatgagtg gtattttccg cgatgtttcc ctgctgcata | 660 |
| agcctgccag ccatcttcgc gatctgcgca ttcgtacgca tttcaatgac gatttcagtc | 720 |
| gtgcgcggct ggaagctgag gtgcgggttg ccggagcact ggatgacgat ttacgggtca | 780 |
| gcgtgcagct cttcgcgggt gacacgctaa ccggagaagc gacgtcgccc ttgggcagcg | 840 |
| cgattattga cgagcgcggc gcgtggagcg atcggacaac gctgtgcatc aacgttgcta | 900 |
| accctgcgct gtggagtgcg gaaacgccgc atctctaccg ggcggttgtg cagttacacc | 960 |
| ggacggacgg tacgctgatt gaggcggagg cctgcgacgt gggattccgg cacgtcagca | 1020 |
| tcgaaaatgg cctgctgctg ctcaacggtc agccactgct catccgcggc accaaccgcc | 1080 |
| acgagcatca tcctgaacgc ggtcaggtga tgatcgtga cactatggtg caggatattt | 1140 |
| tgctgatgaa gcagaataac ttcaacgcgg tgcgctgctc ccattaccct aacgatcccc | 1200 |
| tgtggtatag cctgtgtgac cactacggct tgtacgtcgt ggatgaagcc aacatcgaaa | 1260 |
| cgcatggcat ggtgccgatg aatcgcctga gcgacgatcc cgtctggctt cccgccatga | 1320 |
| gccagcgcgt cacgcgcatg gtgcagcgcg atcgtaatca cccctgcatt attatctggt | 1380 |
| cactgggtaa cgaatcgggc cacggtgcta accatgatgc gctctaccgc tggctgaaaa | 1440 |
| gtgaagatcc ttcccgcccg gtccagtacg aaggtggcgg ggccaatacc gcagcgaccg | 1500 |

-continued

```
atattatctg tccgatgtat gcgcgggtcg atgaggatca acctttcccg gccgtgccga      1560
aatggtccat taaaaaatgg ctgtctatgc caggcgagca gcgtccgctt attctctgtg      1620
aatatgctca tgccatggga aacagccttg gtggctacgc aaaatactgg caggcatttc      1680
gtcagtatcc tcgcctgcag ggcggttttg tctgggactg ggtcgatcag tcgctcataa      1740
aatatgacga taacggcgaa ccctgggctg cctacggtgg cgactttggt gatacgccta      1800
atgatcgcca gttctgcatg aacggctgg tctttgccga ccggacgccc catccctcgc      1860
tctacgaagc ccgccatgcg cagcagttct tccagttcag gctgctaccg ggcagcgagc      1920
gcacgctgga agtgaccagc gaatacctgt tccgccacag tgataatgaa atcctgcact      1980
ggtcggtggc tcaggatggc aacctgctgg ccgccggtga agtcacgctg gatatcgcgc      2040
cacagggccg ccagcagatc gcactcccgg aggtgccgct gcctcaatct gcgggccagc      2100
tctggctgac ggtgcgggtg aacagcctc agccgacggc ctggtcagaa gccggtcata      2160
tcagcgcctg gcagcagtgg ccactggagg cgatcctgaa tgtggccctg ccgcctcagg      2220
cggcgagtgc gccacagctc agccgcggcg aagacaccttt cagcgtggcg gtgaacaacc      2280
agcgctgggc attcagccgt cagcaggcg tgctcacgca gtactggatc gacgatcagc      2340
cgcagctcct gtcgccgctg cgcgatcagt ttacccgtgc gccgctggat aacgatatcg      2400
gcgtcagcga agtcacgcgc atcgacccta atgcctgggt cgagcgctgg aaagcggcgg      2460
ggcactatca gtctgaggtc accaccctgc agtgcaccgc cgaagcgctc tccgacgccg      2520
tcgtgatcaa caccgttcat gcctggcagt tccagggcaa aacgctgttt attagccgta      2580
aagtgtaccg tattgatgga tttggcgaga tggcggtgac ggtgaacgta gagatcgcga      2640
gcggcacgcc ttatccggca cgcatcggta tgagctgtca gctcacccag atcgtcgagc      2700
gagtgaactg gctaggcctg gggccgcatg aaaattaccc ggatcgcctg acctcggcct      2760
gctttgaccg ctgggattta ccgctgagtg aaatgtacac cccgtatgtt ttccccaccg      2820
aaaacggcct gcgctgcggc acgcgtgaac tcaactatgg tgcgcaccag tggcgtggcg      2880
atttccagtt caacatcagt cgctacagcc agacacagct gatggaaacc tgccatcgcc      2940
acctgttacg gcctgaggcg ggcacgtggc tcaatattga tggcttccac atgggcgtcg      3000
gcggtgacga ttcctggagc ccgtcggtat caccggaatt cctgctcagt gcaggacgtt      3060
acagctacca gtttatctgg gggcaacaaa aataa                                 3095
```

<210> SEQ ID NO 47
<211> LENGTH: 34
<212> TYPE: DNA
<213> ORGANISM: Artificial
<220> FEATURE:
<223> OTHER INFORMATION: Synthetic

<400> SEQUENCE: 47

```
gcttaagatc tccctgttga caattaatca tcgg                                    34
```

<210> SEQ ID NO 48
<211> LENGTH: 70
<212> TYPE: DNA
<213> ORGANISM: Artificial
<220> FEATURE:
<223> OTHER INFORMATION: Synthetic

<400> SEQUENCE: 48

```
agtacggccg ctaatgaatc tctgtccagg gtcatggcag tctccttgtg tgaaattgtt       60
atccgctcac                                                               70
```

```
<210> SEQ ID NO 49
<211> LENGTH: 39
<212> TYPE: DNA
<213> ORGANISM: Artificial
<220> FEATURE:
<223> OTHER INFORMATION: Synthetic

<400> SEQUENCE: 49
ccgttagatc tcgctcaagt tagtataaaa aagctgaac                              39

<210> SEQ ID NO 50
<211> LENGTH: 70
<212> TYPE: DNA
<213> ORGANISM: Artificial
<220> FEATURE:
<223> OTHER INFORMATION: Synthetic

<400> SEQUENCE: 50
tagcgggctg atagtgttgt tcagacatga tgaggttcgc cttgaagcct gcttttttat      60
actaagttgg                                                              70

<210> SEQ ID NO 51
<211> LENGTH: 78
<212> TYPE: DNA
<213> ORGANISM: Artificial
<220> FEATURE:
<223> OTHER INFORMATION: Synthetic

<400> SEQUENCE: 51
cgttgggaca acgtcgatct gcgccgaatc tggttgctgg acgccgcctg tgaagcctgc      60 tttttttatac taagttgg                                                    78

<210> SEQ ID NO 52
<211> LENGTH: 80
<212> TYPE: DNA
<213> ORGANISM: Artificial
<220> FEATURE:
<223> OTHER INFORMATION: Synthetic

<400> SEQUENCE: 52
caacagcaga taaaccgcga tcagtaaaaa cgcattggcc gccatggcag tctccttgtg      60
tgaaattgtt atccgctcac                                                   80

<210> SEQ ID NO 53
<211> LENGTH: 17
<212> TYPE: DNA
<213> ORGANISM: Artificial
<220> FEATURE:
<223> OTHER INFORMATION: Synthetic

<400> SEQUENCE: 53
catgtcttct ggtcact                                                      17

<210> SEQ ID NO 54
<211> LENGTH: 16
<212> TYPE: DNA
<213> ORGANISM: Artificial
<220> FEATURE:
<223> OTHER INFORMATION: Synthetic

<400> SEQUENCE: 54
caagcaggtt gaacac                                                       16

<210> SEQ ID NO 55
```

```
<211> LENGTH: 32
<212> TYPE: DNA
<213> ORGANISM: Artificial
<220> FEATURE:
<223> OTHER INFORMATION: Synthetic

<400> SEQUENCE: 55
cccaagcttc cctgatcaat gaggaggcgt tc                                    32

<210> SEQ ID NO 56
<211> LENGTH: 33
<212> TYPE: DNA
<213> ORGANISM: Artificial
<220> FEATURE:
<223> OTHER INFORMATION: Synthetic

<400> SEQUENCE: 56
cgggatccga cgatcggggt cgggacgtaa ggg                                   33

<210> SEQ ID NO 57
<211> LENGTH: 557
<212> TYPE: PRT
<213> ORGANISM: Artificial
<220> FEATURE:
<223> OTHER INFORMATION: Xaa is any naturally occurring amino acid 4,
      5, 11, 12, 15, 19, 21, 25. 29, 31, 32, 34, 37, 38, 39, 40, 41,
      42, 44, 45, 47, 49, 50, 53, 54, 55, 56, 58, 60, 61, 64,
      68, 69, 71, 74, 75, 78, 79, 80, 82, 83, 85, 86, 93, 107,
      119, 122, 131, 139, 143, 148, 154, 156, 157, 158, 160,
      161, 168, 171, 176, 179, 181, 182, 185, 190, 191, 194,
      195, 202, 203, 205, 206, 207, 213, 215, 238, 241, 251,
      258, 264, 273, 274, 275, 281, 286, 288, 289, 290, 293,
      294, 295, 296, 297, 303, 304, 309, 311, 314, 317, 325,
      329, 331, 338, 348, 364, 368, 378, 384, 404, 412, 416,
      426, 430, 432, 434, 443, 444, 446, 450, 475, 478, 483,
      487, 496, 506, 507, 508, 509, 512, 514, 515, 516, 517,
      528, 529, 532, 555, 557
<220> FEATURE:
<221> NAME/KEY: variation
<222> LOCATION: (1)..(557)

<400> SEQUENCE: 57

Met Ala Ala Xaa Xaa Phe Leu Leu Ile Ala Xaa Xaa Leu Leu Xaa Leu
1               5                   10                  15

Met Val Xaa Ala Xaa Pro Leu Gly Xaa Gly Leu Ala Xaa Leu Xaa Xaa
            20                  25                  30

Asp Xaa Pro Leu Xaa Xaa Xaa Xaa Xaa Glu Xaa Xaa Leu Xaa Arg
        35                  40                  45

Xaa Xaa Gly Val Xaa Xaa Xaa Xaa Met Xaa Trp Xaa Xaa Tyr Leu Xaa
    50                  55                  60

Ala Ile Leu Xaa Xaa Asn Xaa Leu Gly Xaa Xaa Val Leu Xaa Xaa Xaa
65                  70                  75                  80

Leu Xaa Xaa Gln Xaa Xaa Leu Pro Leu Asn Pro Gln Xaa Leu Pro Gly
            85                  90                  95

Leu Ser Trp Asp Leu Ala Leu Asn Thr Ala Xaa Ser Phe Val Thr Asn
                100                 105                 110

Thr Asn Trp Gln Ser Tyr Xaa Gly Glu Xaa Thr Leu Ser Tyr Phe Ser
            115                 120                 125

Gln Met Xaa Gly Leu Thr Val Gln Asn Phe Xaa Ser Ala Ala Xaa Gly
        130                 135                 140

Ile Ala Val Xaa Phe Ala Leu Ile Arg Xaa Phe Xaa Xaa Ser Xaa
145                 150                 155                 160

Xaa Thr Leu Gly Asn Ala Trp Xaa Asp Leu Xaa Arg Ile Thr Leu Xaa
                165                 170                 175
```

```
Val Leu Xaa Pro Xaa Xaa Leu Leu Xaa Ala Leu Phe Phe Xaa Xaa Gln
            180                 185                 190

Gly Xaa Xaa Gln Asn Phe Leu Pro Tyr Xaa Xaa Val Xaa Xaa Xaa Glu
        195                 200                 205

Gly Ala Gln Gln Xaa Leu Xaa Met Gly Pro Val Ala Ser Gln Glu Ala
    210                 215                 220

Ile Lys Met Leu Gly Thr Asn Gly Gly Phe Phe Asn Xaa Asn Ser
225                 230                 235                 240

Xaa His Pro Phe Glu Asn Pro Thr Ala Leu Xaa Asn Phe Val Gln Met
                245                 250                 255

Leu Xaa Ile Phe Leu Ile Pro Xaa Ala Leu Cys Phe Ala Phe Gly Glu
        260                 265                 270

Xaa Xaa Xaa Asp Arg Arg Gln Gly Xaa Met Leu Leu Trp Xaa Met Xaa
        275                 280                 285

Xaa Phe Val Xaa Xaa Xaa Xaa Val Met Trp Ala Glu Xaa Xaa
        290                 295                 300

Gly Asn Pro His Xaa Leu Xaa Leu Gly Xaa Asp Ser Xaa Ile Asn Met
305                 310                 315                 320

Glu Gly Lys Glu Xaa Arg Phe Gly Xaa Leu Xaa Ser Ser Leu Phe Ala
                325                 330                 335

Val Xaa Thr Thr Ala Ala Ser Cys Gly Ala Val Xaa Ala Met His Asp
        340                 345                 350

Ser Phe Thr Ala Leu Gly Gly Met Val Pro Met Xaa Leu Met Gln Xaa
        355                 360                 365

Gly Glu Val Val Phe Gly Val Gly Xaa Gly Leu Tyr Gly Met Xaa
        370                 375                 380

Leu Phe Val Leu Leu Ala Val Phe Ile Ala Gly Leu Met Ile Gly Arg
385                 390                 395                 400

Thr Pro Glu Xaa Leu Gly Lys Lys Ile Asp Val Xaa Glu Met Lys Xaa
                405                 410                 415

Thr Ala Leu Ala Ile Leu Val Thr Pro Xaa Leu Val Leu Xaa Gly Xaa
        420                 425                 430

Ala Xaa Ala Met Met Thr Asp Ala Gly Arg Xaa Xaa Met Xaa Asn Pro
        435                 440                 445

Gly Xaa His Gly Phe Ser Glu Val Leu Tyr Ala Val Ser Ser Ala Ala
    450                 455                 460

Asn Asn Asn Gly Ser Ala Phe Ala Gly Leu Xaa Ala Asn Xaa Pro Phe
465                 470                 475                 480

Trp Asn Xaa Leu Leu Ala Xaa Cys Met Phe Val Gly Arg Phe Gly Xaa
            485                 490                 495

Ile Ile Pro Val Met Ala Ile Ala Gly Xaa Xaa Xaa Xaa Lys Lys Xaa
                500                 505                 510

Gln Xaa Xaa Xaa Xaa Gly Thr Leu Pro Thr His Gly Pro Leu Phe Xaa
        515                 520                 525

Xaa Leu Leu Xaa Gly Thr Val Leu Leu Val Gly Ala Leu Thr Phe Ile
        530                 535                 540

Pro Ala Leu Ala Leu Gly Pro Val Ala Glu Xaa Leu Xaa
545                 550                 555

<210> SEQ ID NO 58
<211> LENGTH: 681
<212> TYPE: PRT
<213> ORGANISM: Artificial
<220> FEATURE:
<223> OTHER INFORMATION: Xaa is any naturally occurring amino acid 4,
      6, 7, 8, 10, 11, 12, 14, 15, 16, 17, 18, 19, 20, 26, 28, 29, 31,
```

-continued

```
         38, 40, 41, 44, 47, 48, 49, 50, 52, 54, 55, 57, 58, 59,
         61, 63, 65, 66, 69, 70, 74, 81, 104, 107, 110, 111, 112,
         113, 118, 119, 120, 122, 125, 131, 139, 147, 190, 193,
         226, 227, 237, 248, 249, 251, 252, 305, 320, 321, 323,
         326, 329, 331, 332, 354, 359, 367, 368, 370, 371, 373,
         375, 378, 381, 386, 388, 389, 390, 392, 397, 401, 405,
         408, 409, 411, 414, 415, 417, 418, 419, 421, 422, 426,
         426, 428, 434, 437, 438, 443, 459, 475, 492, 559, 604,
         607, 609, 614, 627, 642, 645, 647, 648, 649, 655, 667,
         671, 674, 677, 678, 679, 681
<220> FEATURE:
<221> NAME/KEY: variation
<222> LOCATION: (1)..(681)

<400> SEQUENCE: 58

Met Ser Arg Xaa Gln Xaa Xaa Xaa Phe Xaa Xaa Xaa Leu Xaa Xaa Xaa
1               5                   10                  15

Xaa Xaa Xaa Xaa Ala Val Lys Lys Leu Xaa Pro Xaa Xaa Gln Xaa Arg
            20                  25                  30

Asn Pro Val Met Phe Xaa Val Xaa Xaa Gly Ser Xaa Leu Thr Xaa Xaa
        35                  40                  45

Xaa Xaa Ile Xaa Met Xaa Xaa Gly Xaa Xaa Gly Xaa Ala Xaa Phe
    50                  55                  60

Xaa Xaa Ala Ile Xaa Xaa Trp Leu Trp Xaa Thr Val Leu Phe Ala Asn
65                  70                  75                  80

Xaa Ala Glu Ala Leu Ala Glu Gly Arg Ser Lys Ala Gln Ala Asn Ser
                85                  90                  95

Leu Lys Gly Val Lys Lys Thr Xaa Phe Ala Xaa Lys Leu Xaa Xaa Xaa
            100                 105                 110

Xaa Tyr Gly Ala Ala Xaa Xaa Xaa Val Xaa Ala Asp Xaa Leu Arg Lys
        115                 120                 125

Gly Asp Xaa Val Leu Val Glu Ala Gly Asp Xaa Ile Pro Cys Asp Gly
    130                 135                 140

Glu Val Xaa Glu Gly Gly Ala Ser Val Asp Glu Ser Ala Ile Thr Gly
145                 150                 155                 160

Glu Ser Ala Pro Val Ile Arg Glu Ser Gly Gly Asp Phe Ala Ser Val
                165                 170                 175

Thr Gly Gly Thr Arg Ile Leu Ser Asp Trp Leu Val Ile Xaa Cys Ser
            180                 185                 190

Xaa Asn Pro Gly Glu Thr Phe Leu Asp Arg Met Ile Ala Met Val Glu
        195                 200                 205

Gly Ala Gln Arg Arg Lys Thr Pro Asn Glu Ile Ala Leu Thr Ile Leu
    210                 215                 220

Leu Xaa Xaa Leu Thr Ile Val Phe Leu Leu Ala Thr Xaa Thr Leu Trp
225                 230                 235                 240

Pro Phe Ser Ala Trp Gly Gly Xaa Xaa Val Xaa Xaa Thr Val Leu Val
                245                 250                 255

Ala Leu Leu Val Cys Leu Ile Pro Thr Thr Ile Gly Gly Leu Leu Ser
            260                 265                 270

Ala Ile Gly Val Ala Gly Met Ser Arg Met Leu Gly Ala Asn Val Ile
        275                 280                 285

Ala Thr Ser Gly Arg Ala Val Glu Ala Ala Gly Asp Val Asp Val Leu
    290                 295                 300

Xaa Leu Asp Lys Thr Gly Thr Ile Thr Leu Gly Asn Arg Gln Ala Xaa
305                 310                 315                 320

Xaa Phe Xaa Pro Ala Xaa Gly Val Xaa Glu Xaa Xaa Leu Ala Asp Ala
                325                 330                 335

Ala Gln Leu Ala Ser Leu Ala Asp Glu Thr Pro Glu Gly Arg Ser Ile
```

```
                    340                 345                 350
Val Xaa Leu Ala Lys Gln Xaa Phe Asn Leu Arg Glu Arg Asp Xaa Xaa
                355                 360                 365

Ser Xaa Xaa Ala Xaa Phe Xaa Pro Phe Xaa Ala Gln Xaa Arg Met Ser
370                 375                 380

Gly Xaa Asn Xaa Xaa Xaa Arg Xaa Ile Arg Lys Gly Xaa Val Asp Ala
385                 390                 395                 400

Xaa Arg Arg His Xaa Glu Ala Xaa Xaa Gly Xaa Phe Pro Xaa Xaa Val
                405                 410                 415

Xaa Xaa Xaa Val Xaa Xaa Val Ala Arg Xaa Gly Xaa Thr Pro Leu Val
                420                 425                 430

Val Xaa Glu Gly Xaa Xaa Val Leu Gly Val Xaa Ala Leu Lys Asp Ile
                435                 440                 445

Val Lys Gly Gly Ile Lys Glu Arg Phe Ala Xaa Leu Arg Lys Met Gly
                450                 455                 460

Ile Lys Thr Val Met Ile Thr Gly Asp Asn Xaa Leu Thr Ala Ala Ala
465                 470                 475                 480

Ile Ala Ala Glu Ala Gly Val Asp Asp Phe Leu Xaa Glu Ala Thr Pro
                485                 490                 495

Glu Ala Lys Leu Ala Leu Ile Arg Gln Tyr Gln Ala Glu Gly Arg Leu
                500                 505                 510

Val Ala Met Thr Gly Asp Gly Thr Asn Asp Ala Pro Ala Leu Ala Gln
                515                 520                 525

Ala Asp Val Ala Val Ala Met Asn Ser Gly Thr Gln Ala Ala Lys Glu
                530                 535                 540

Ala Gly Asn Met Val Asp Leu Asp Ser Asn Pro Thr Lys Leu Xaa Glu
545                 550                 555                 560

Val Val His Ile Gly Lys Gln Met Leu Met Thr Arg Gly Ser Leu Thr
                565                 570                 575

Thr Phe Ser Ile Ala Asn Asp Val Ala Lys Tyr Phe Ala Ile Ile Pro
                580                 585                 590

Ala Ala Phe Ala Ala Thr Tyr Pro Gln Leu Asn Xaa Leu Asn Xaa Met
                595                 600                 605

Xaa Leu His Ser Pro Xaa Ser Ala Ile Leu Ser Ala Val Ile Phe Asn
                610                 615                 620

Ala Leu Xaa Ile Val Phe Leu Ile Pro Leu Ala Leu Lys Gly Val Ser
625                 630                 635                 640

Tyr Xaa Pro Leu Xaa Ala Xaa Xaa Leu Arg Arg Asn Leu Xaa Ile
                645                 650                 655

Tyr Gly Leu Gly Gly Leu Leu Val Pro Phe Xaa Gly Ile Lys Xaa Ile
                660                 665                 670

Asp Xaa Leu Leu Xaa Xaa Xaa Gly Xaa
                675                 680

<210> SEQ ID NO 59
<211> LENGTH: 189
<212> TYPE: PRT
<213> ORGANISM: Artificial
<220> FEATURE:
<223> OTHER INFORMATION: Xaa is any naturally occurring amino acid 3,
      8, 9, 10, 11, 12, 13, 15, 16, 17, 18, 20, 28, 30, 32, 33, 42,
      43, 44, 45, 46, 47, 48, 49, 60, 61, 62, 66, 73, 74, 75, 80,
      83, 89, 93, 97, 98, 100, 107, 111, 113, 114, 115, 123,
      130, 131, 133, 135, 138, 141, 144, 146, 149, 151, 152,
      153, 154, 155, 156, 157, 159, 160, 161, 162, 163, 165,
      168, 169, 170, 173, 175, 178, 178, 179, 180, 186, 187,
      188, 189
<220> FEATURE:
```

```
<221> NAME/KEY: variation
<222> LOCATION: (1)..(189)

<400> SEQUENCE: 59

Met Ser Xaa Leu Arg Pro Ala Xaa Xaa Xaa Xaa Xaa Leu Xaa Xaa
1               5                   10                  15

Xaa Xaa Gly Xaa Val Tyr Pro Leu Leu Thr Thr Xaa Leu Xaa Gln Xaa
            20                  25                  30

Xaa Phe Pro Trp Gln Ala Asn Gly Ser Xaa Xaa Xaa Xaa Xaa Xaa
        35                  40                  45

Xaa Arg Gly Ser Ala Leu Ile Gly Gln Asn Phe Xaa Xaa Xaa Gly Tyr
    50                  55                  60

Phe Xaa Gly Arg Pro Ser Ala Thr Xaa Xaa Xaa Pro Tyr Asn Pro Xaa
65                  70                  75                  80

Ala Ser Xaa Gly Ser Asn Leu Ala Xaa Ser Asn Pro Xaa Leu Asp Lys
            85                  90                  95

Xaa Xaa Ala Xaa Arg Val Ala Ala Leu Arg Xaa Ala Asn Pro Xaa Ala
            100                 105                 110

Xaa Xaa Xaa Val Pro Val Glu Leu Val Thr Xaa Ser Ala Ser Gly Leu
            115                 120                 125

Asp Xaa Xaa Ile Xaa Pro Xaa Ala Ala Xaa Trp Gln Xaa Pro Arg Xaa
    130                 135                 140

Ala Xaa Ala Arg Xaa Leu Xaa Xaa Xaa Xaa Xaa Xaa Leu Xaa Xaa
145                 150                 155                 160

Xaa Xaa Xaa Gln Xaa Pro Leu Xaa Xaa Xaa Ile Gly Xaa Pro Xaa Val
            165                 170                 175

Asn Xaa Xaa Xaa Leu Asn Leu Ala Leu Xaa Xaa Leu Xaa
            180                 185
```